US007858848B2

(12) United States Patent
Reuber et al.

(10) Patent No.: US 7,858,848 B2
(45) Date of Patent: *Dec. 28, 2010

(54) TRANSCRIPTION FACTORS FOR INCREASING YIELD

(75) Inventors: T. Lynne Reuber, San Mateo, CA (US); Oliver Ratcliffe, Oakland, CA (US); Jacqueline Heard, Webster Groves, MO (US); Jose Luis Riechmann, Barcelona (ES); Omaira Pineda, Vero Beach, FL (US); Luc Adam, Hayward, CA (US)

(73) Assignee: Mendel Biotechnology Inc., Hayward, CA (US)

( * ) Notice: Subject to any disclaimer, the term of this patent is extended or adjusted under 35 U.S.C. 154(b) by 242 days.

This patent is subject to a terminal disclaimer.

(21) Appl. No.: 11/479,226

(22) Filed: Jun. 30, 2006

(65) Prior Publication Data

US 2007/0022495 A1 Jan. 25, 2007

Related U.S. Application Data

(63) Continuation-in-part of application No. 09/713,994, filed on Nov. 16, 2000, now abandoned.

(60) Provisional application No. 60/166,228, filed on Nov. 17, 1999, provisional application No. 60/197,899, filed on Apr. 17, 2000, provisional application No. 60/227,439, filed on Aug. 22, 2000.

(51) Int. Cl.
C12N 15/82 (2006.01)
A01H 5/00 (2006.01)
A01H 5/10 (2006.01)

(52) U.S. Cl. .................. 800/298; 800/278; 800/279; 800/287

(58) Field of Classification Search ................ None
See application file for complete search history.

(56) References Cited

U.S. PATENT DOCUMENTS

| 5,891,859 | A | 4/1999 | Thomashow et al. |
| 5,892,009 | A | 4/1999 | Thomashow et al. |
| 5,939,601 | A | 8/1999 | Klessig et al. |
| 6,077,994 | A | 6/2000 | Coupland et al. |
| 6,093,874 | A | 7/2000 | Jofuku et al. |
| 6,121,513 | A | 9/2000 | Zhang et al. |
| 6,329,567 | B1 | 12/2001 | Jofuku et al. |
| 6,417,428 | B1 | 7/2002 | Thomashow et al. |
| 6,664,446 | B2 * | 12/2003 | Heard et al. ............... 800/301 |
| 7,238,860 | B2 | 12/2003 | Ratcliffe et al. |
| 6,706,866 | B1 | 3/2004 | Thomashow et al. |
| 6,717,034 | B2 | 4/2004 | Jiang |
| 6,835,540 | B2 | 12/2004 | Broun |
| 6,846,669 | B1 | 1/2005 | Jofuku et al. |
| 6,946,586 | B1 | 9/2005 | Fromm et al. |
| 7,109,393 | B2 | 9/2006 | Gutterson et al. |
| 7,135,616 | B2 | 11/2006 | Heard et al. |
| 7,196,245 | B2 | 2/2007 | Jiang et al. |
| 7,223,904 | B2 | 5/2007 | Heard et al. |
| 7,345,217 | B2 | 3/2008 | Zhang et al. |
| 2002/0023281 | A1 | 2/2002 | Gorlach et al. |
| 2002/0088022 | A1 | 7/2002 | Harris et al. |
| 2002/0138882 | A1 | 9/2002 | Cahoon et al. |
| 2003/0093837 | A1 | 5/2003 | Keddie et al. |
| 2003/0121070 | A1 | 6/2003 | Adam et al. |
| 2003/0217383 | A1 | 11/2003 | Reuber et al. |
| 2003/0233670 | A1 | 12/2003 | Edgerton et al. |
| 2003/0233680 | A1 | 12/2003 | Thomashow et al. |
| 2004/0019927 | A1 | 1/2004 | Sherman et al. |
| 2004/0031072 | A1 | 2/2004 | La Rosa et al. |
| 2004/0034888 | A1 | 2/2004 | Liu et al. |
| 2004/0123343 | A1 | 6/2004 | La Rosa et al. |
| 2004/0128712 | A1 | 7/2004 | Jiang et al. |
| 2004/0214272 | A1 | 10/2004 | La Rosa et al. |
| 2004/0216190 | A1 | 10/2004 | Kovalic et al. |
| 2005/0086718 | A1 | 4/2005 | Heard et al. |
| 2005/0097638 | A1 | 5/2005 | Jiang et al. |
| 2005/0155117 | A1 | 7/2005 | Century et al. |
| 2005/0172364 | A1 | 8/2005 | Heard |
| 2006/0008874 | A1 | 1/2006 | Creelman et al. |
| 2006/0015972 | A1 | 1/2006 | Heard et al. |
| 2006/0162018 | A1 | 7/2006 | Gutterson et al. |
| 2006/0195944 | A1 | 8/2006 | Heard et al. |
| 2006/0242738 | A1 | 10/2006 | Sherman et al. |
| 2006/0272060 | A1 | 11/2006 | Heard et al. |

(Continued)

FOREIGN PATENT DOCUMENTS

| DE | 19503359 | 2/1996 |
| EP | 0803572 | 10/1997 |
| EP | 0969092 | 5/2000 |
| EP | 1033405 | 9/2000 |

(Continued)

OTHER PUBLICATIONS

Yang et al (2001, PNAS 98(20):11438-11443).*
Riechmann et al (2000, Current Opinion in Plant Biology 3:423-434).*
Bowie et al, Science 247:1306-1310, 1990.*
McConnell et al, Nature 411 (6838):709-713, 2001.*
Lai et al (2008, BMC Plant Biology 8, Article No. 8, pp. 1-13).*
U.S. Appl. No. 12/064,961, Gutterson, N. et al. SEQ 221, 222, entire document.
U.S. Appl. No. 12/077,535, Repetti, P. et al. SEQ 401, 402, entire document.

(Continued)

Primary Examiner—Stuart F. Baum
(74) Attorney, Agent, or Firm—Jeffery M. Libby; Yifan Mao

(57) ABSTRACT

The invention is directed to transgenic plants transformed with nucleic acids that encode a plant transcription factor that increases the transgenic plant's size and yield and/or delays flowering in the plant, and methods of using and producing the transgenic plants.

25 Claims, 4 Drawing Sheets

U.S. PATENT DOCUMENTS

Figure 1:
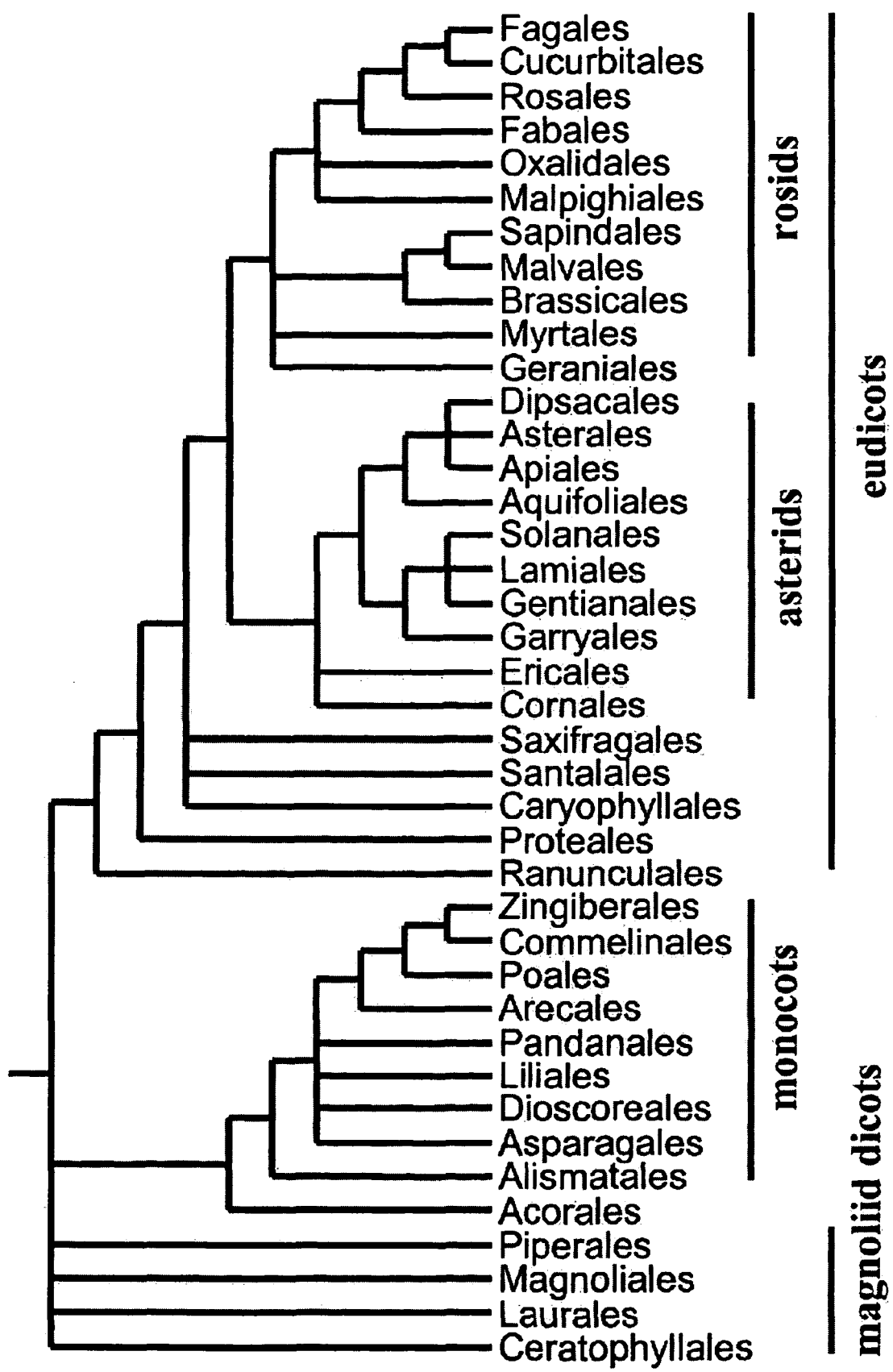

| | | | |
|---|---|---|---|
| 2007/0022495 | A1 | 1/2007 | Reuber et al. |
| 2007/0101454 | A1 | 5/2007 | Jiang et al. |
| 2007/0186308 | A1 | 8/2007 | Reuber et al. |
| 2007/0199107 | A1 | 8/2007 | Ratcliffe et al. |
| 2007/0209086 | A1 | 9/2007 | Ratcliffe et al. |
| 2007/0226839 | A1 | 9/2007 | Gutterson et al. |
| 2008/0010703 | A1 | 1/2008 | Creelman et al. |
| 2008/0155706 | A1 | 6/2008 | Riechmann et al. |
| 2008/0163397 | A1 | 7/2008 | Ratcliffe et al. |
| 2008/0229448 | A1 | 9/2008 | Libby et al. |

FOREIGN PATENT DOCUMENTS

| | | |
|---|---|---|
| JP | 2005-013214 | 1/2005 |
| WO | WO9632007 | 10/1996 |
| WO | WO9724449 | 7/1997 |
| WO | WO9747183 | 12/1997 |
| WO | WO9807842 | 2/1998 |
| WO | WO9837184 | 8/1998 |
| WO | WO9837755 | 9/1998 |
| WO | WO98048007 | 10/1998 |
| WO | WO98/58069 | 12/1998 |
| WO | WO9924573 | 5/1999 |
| WO | WO9938977 | 8/1999 |
| WO | WO9941974 | 8/1999 |
| WO | WO9953016 | 10/1999 |
| WO | WO9955840 | 11/1999 |
| WO | WO0032761 | 6/2000 |
| WO | WO0046383 | 8/2000 |
| WO | WO0053724 | 9/2000 |
| WO | WO0070059 | 11/2000 |
| WO | WO0125458 | 4/2001 |
| WO | WO0149840 | 7/2001 |
| WO | WO0208410 | 1/2002 |
| WO | WO0208411 | 1/2002 |
| WO | WO0215675 A1 | 2/2002 |
| WO | WO0216655 | 2/2002 |
| WO | WO0222675 | 3/2002 |
| WO | WO02079245 A | 10/2002 |
| WO | WO03000898 | 1/2003 |
| WO | WO03008540 | 1/2003 |
| WO | WO03013227 A2 | 2/2003 |
| WO | WO03014327 A2 | 2/2003 |
| WO | WO03020936 | 3/2003 |
| WO | WO03044190 | 5/2003 |
| WO | WO03048319 | 6/2003 |
| WO | WO03081978 | 10/2003 |
| WO | WO03097790 | 11/2003 |
| WO | WO2004029222 | 4/2004 |
| WO | WO2004031349 | 4/2004 |
| WO | WO2004035798 | 4/2004 |
| WO | WO2004076638 | 9/2004 |
| WO | WO2004087878 | 10/2004 |
| WO | WO2005001050 | 1/2005 |
| WO | WO2005047516 A2 | 5/2005 |
| WO | WO2006033708 A2 | 3/2006 |
| WO | WO2006069201 A2 | 6/2006 |
| WO | WO2006130156 A2 | 12/2006 |
| WO | WO2007028165 A2 | 3/2007 |
| WO | WO2007127186 A2 | 11/2007 |

OTHER PUBLICATIONS

U.S. Appl. No. 11/981,576, Gutterson, N. et al. SEQ 1, 2, entire document.

U.S. Appl. No. 11/632,390, Zhang, James et al. SEQ 249, 250, entire document.

NCBI acc. No. AAB38748 (gi: 1732406) (Dec. 16, 1996); Xu,P., et al. "Direct Submission" (Submitted(Dec. 6, 1996) Biotechnology Institute, Zhejiang Agriculture Unversity, Hangzhou, Zhejiang 310029, P.R.China).

NCBI acc. No. AAC14323 (gi: 3065895) (Apr. 21, 1998); Park,J.M., et al. "TSI1 [*Nicotiana tabacum*]"; source:*Nicotiana tabacum* (common tobacco); Title: "Direct Submission" (Submitted (Apr. 10, 1998) Graduate School of Biotechnology, Korea University, 1,5-Ka Anamdong, Sungbuk-ku, Seoul 136-701, Korea).

NCBI acc. No. AAC24587 (gi: 3264767) (Jun. 28, 1998); Mbeguie-A-Mbeguie.D., et al. "AP2 domain containing protein [*Prunus armeniaca*]"; source: *Prunus armeniaca* (apricot); Title: "Molecular cloning and partial nucleotide sequence of an AP2 domain containing protein from apricot" (Unpublished).

NCBI acc. No. AAC29516 (gi: 1688233) (Nov. 28, 1996); Stidd,J.E., et al. "DNA binding protein homolog [*Solanum tuberosum*]"; source: *Solanum tuberosum* (potato); Title: "cDNA sequence from a logphase cell suspension culture with similarity to DNA binding proteins" (Unpublished).

NCBI acc. No. AAC49740(gi: 2213783) (Jun. 25, 1997); Zhou,J., et al. "Pti5 [*Lycopersicon esculentum*]"; source: *Lycopersicon esculentum* (tomato).

NCBI acc. No. AAC49741 (gi: 2213785) (Jun. 25, 1997); Zhou,J., et al. "Pti6 [*Lycopersicon esculentum*]"; source: *Lycopersicon esculentum* (tomato).

NCBI acc. No. AAC50047 (gi: 2213781) (Jun. 25, 1997); Zhou,J., et al. "Pti4 [*Lycopersicon esculentum*]"; source: *Lycopersicon esculentum* (tomato).

NCBI acc. No. AAC62619 (gi: 3695034) (Oct. 6, 1998); Horvath,D. M., et al. "ethylene response element binding protein 1 [*Nicotiana tabacum*]"; source: *Nicotiana tabacum* (common tobacco); Title: "Four classes of salicylate-induced tobacco genes" (Mol. Plant Microbe Interact. 11 (9), 895-905 (1998)).

NCBI acc. No. AAD00708 (gi: 4099914) (Jan. 5, 1999); Gardner,R. C., et al. "ethylene-responsive element binding protein homolog [*Stylosanthes hamata*]"; source: *Stylosanthes hamata*; Title: "Aluminium Tolerance in Yeast Conferred by Over-expression of Stylosanthes genes" (Unpublished).

NCBI acc. No. AAD09248 (gi: 4099921) (Jan, 5, 1999); Gardner,R. C., et al. "EREBP-3 homolog [*Stylosanthes hamata*]"; source: *Stylosanthes hamata*; Title: "Aluminium Tolerance in Yeast Conferred by Over-expression of Stylosanthes Genes" (Unpublished).

NCBI acc. No. AAF05606 (gi: 6176534) (Nov. 2, 1999); Cao,Z.F., et al. "EREBP-like protein [*Oryza sativa*]"; source: *Oryza sativa* (japonica cultivar-group); Title: "Characterization of a rice cDNA encoding an EREBP-like protein induced by ethylene" (Unpublished).

NCBI acc. No. AAF23899 (gi: 6689918) (Jan. 11, 2000); Cheong,Y. H., et al. "transcription factor EREBP1 [*Oryza sativa*]"; source: *Oryza sativa*; Title: "A plant novel MAP kinase, RMAPK1, phosphorylates defense-related transcription factor" (Unpublished).

NCBI acc. No. AAF63205 (gi: 7528276) (Apr. 9, 2000); Scharte,J., et al. "AP2-related transcription factor [*Mesembryanthemum crystallinum*]"; source: *Mesembryanthemum crystallinum* (common iceplant).

NCBI acc. No. AAF76898 (gi: 8571476) (Jun. 18, 2000); Shen,Y., et al. "apetala2 domain-containing protein [*Atriplex hortensis*]"; source: *Atriplex hortensis*.

NCBI acc. No. AAG43545 (gi: 12003376) (Jan. 2, 2001); Durrant,W. E., et al. "Avr9/Cf-9 rapidly elicited protein 1 [*Nicotiana tabacum*]"; source: *Nicotiana tabacum* (common tobacco).

NCBI acc. No. AAG49031 (gi: 12231294) (Jan. 16, 2001); Giovannoni,J.J., et al. "ripening regulated protein DDTFR 10/A [*Lycopersicon esculentum*]"; source: *Lycopersicon esculentum* (*Solanum lycopersicum*).

NCBI acc. No. AAG60182 (gi: 12597874) (Jan. 30, 2001); Buell,C. R., et al. "putative ethylene-responsive element binding protein [*Oryza sativa*]"; source: *Oryza sativa*.

NCBI acc. No. AAK31279 (gi: 13569995) (Apr. 10, 2001); Buell,C. R., et al. "putative ethylene-responsive element binding protein [*Oryza sativa*]"; source: *Oryza sativa*.

NCBI acc. No. AAK52110 (gi: 14018047) (May 11, 2001); Nascimento,L.U., et al. "Putative protein containing AP2 DNA binding domain [*Oryza sativa*]"; source: *Oryza sativa*; Title: "Genomic Sequence for *Oryza sativa*, Nipponbare Strain, Chromosome X, Clone OSJNBb0061118, Complete Sequence" (Unpublished).

NCBI acc. No. AAK92632 (gi: 15217288) (Aug. 21, 2001); Spiegel,L., et al. "Putative EREBP-like protein [*Oryza sativa*]"; source: *Oryza sativa* (japonica cultivar-group); Title: "Genomic Sequence for *Oryza sativa*, Nipponbare strain, clone OSJNBa0032G08, from Chromosome 3, complete sequence" (Unpublished).

NCBI acc. No. AAK92633 (gi: 15217289) (Aug. 21, 2001); Spiegel,L., et al. "Putative AP2 domain containing transcription factor [*Oryza sativa*]"; source: *Oryza sativa* (japonica cultivar-group); Title: "Genomic Sequence for Oryza sativa, Nipponbare strain, clone OSJNBa0032G08, from Chromosome 3, complete sequence".

NCBI acc. No. AAK92635 (gi: 15217291) (Aug. 21, 2001); Spiegel,L., et al. "Putative AP2 domain containing protein [*Oryza sativa*]"; source: *Oryza sativa* (japonica cultivar-group); Title: "Genomic Sequence for *Oryza sativa*, Nipponbare strain, clone OSJNBa0032G08, from Chromosome 3, complete sequence" (Unpublished).

NCBI acc. No. AAK92636 (gi: 15217292) (Aug. 21, 2001); Spiegel,L., et al. "Putative AP2 domain containing protein [*Oryza sativa*]"; source: *Oryza sativa* (japonica cultivar-group); Title: "Genomic Sequence for *Oryza sativa*, Nipponbare strain, clone OSJNBa0032G08, from Chromosome 3, complete sequence" (Unpublished).

NCBI acc. No. AB016264 (gi: 8809570) (Jun. 28, 2000); Kitajima,S., et al. "*Nicotiana sylvestris* nserf2 gene for ethylene-responsive element binding factor, complete cds"; source: *Nicotiana sylvestris* (wood tobacco).

NCBI acc. No. AB016266 (gi: 8809574) (Jun. 28, 2000); Kitajima,S., et al. "*Nicotiana sylvestris* nserf4 gene for ethylene-responsive element binding factor, complete cds"; source: *Nicotiana sylvestris* (wood tobacco).

NCBI acc. No. AB018117 (gi: 3702735) (Oct. 6, 1998); Nakamura,Y., et al. "*Arabidopsis thaliana* strain Columbia chromosome 5 clone MQL5, * Sequencing in Progress *"; source: *Arabidopsis thaliana* (thale cress); Title: "Structural Analysis of *Arabidopsis thaliana* Chromosome 5. IX" (Unpublished (1998)).

NCBI acc. No. AB025608 (gi: 4589414) (Apr. 20, 1999); Nakamura,Y., et al. "*Arabidopsis thaliana* genomic DNA, chromosome 3, TAC clone: K13B15, complete sequence"; source: *Arabidopsis thaliana* (thale cress); Title: "Structural Analysis of *Arabidopsis thaliana* Chromosome 3. II" (Unpublished (1999)).

NCBI accession. No. AB025628 (gi:4589434) (pos. 69357-69929) (Apr. 20, 1999); Nakamura,Y., "*Arabidopsis thaliana* genomic DNA, chromosome 5, P1 clone: MNJ7, complete sequence".

NCBI acc. No. AB035270 (gi: 6478844) (Nov. 30, 1999); Ashida,Y., et al. "*Matricaria chamomilla* McEREBP1 mRNA for ethylene-responsive element binding protein1 homolog, partial cds"; source: *Matricaria chamomilla*.

NCBI acc. No. AC025907 (gi: 7249444) (Mar. 16, 2000); Llaca,V., et al. "*Oryza sativa* chromosome 10 clone nbxb0094K20, * Sequencing in Progress *, 2 ordered pieces"; source: *Oryza sativa*; Title: "Rice Chromosome 10" (Unpublished).

NCBI acc. No. AC079890 (gi: 10179366) (Sep. 16, 2000); Buell,R., et al. "*Oryza sativa* chromosome 10 clone OSJNBb0089A17, * Sequencing in Progress *, 12 unordered pieces"; source: *Oryza sativa*; Title: "*Oryza sativa* ssp. japonica cv. Nipponbare OSJNBb0089A17 BAC genomic sequence" (Unpublished).

NCBI acc. No. AC084763 (gi: 11178087) (Nov. 15, 2000); Buell,R., et al. "*Oryza sativa* chromosome 10 clone OSJNBa0027P10, * Sequencing in Progress *, 9 unordered pieces"; source: *Oryza sativa*; Title: "*Oryza sativa* ssp. japonica cv. Nipponbare OSJNBa0027P10 BAC genomic sequence" (Unpublished).

NCBI acc. No. AF057373 (gi: 3695033) (Oct. 6, 1998); Horvath,D. M., et al. "*Nicotiana tabacum* ethylene response element binding protein 1 (EREBP1) mRNA, EREBP1-2 allele, partial cds"; source: *Nicotiana tabacum* (common tobacco).

NCBI acc. No. AF204784 (gi: 12231293) (Jan. 16, 2001); Giovannoni,J.J., et al. "*Lycopersicon esculentum* ripening regulated protein DDTFR10/A (DDTFR10/A) mRNA, partial cds"; source: *Lycopersicon esculentum* (Solanum lycopersicum).

NCBI acc. No. AF211527 (gi: 12003375) (Jan. 2, 2001); Durrant,W. E., et al. "*Nicotiana tabacum* Avr9/Cf-9 rapidly elicited protein 1 (ACRE1) mRNA, complete cds"; source: *Nicotiana tabacum* (common tobacco).

NCBI acc. No. AF245119 (gi: 7528275) (Apr. 9, 2000); Scharte,J., et al. "*Mesembryanthemum crystallinum* AP2 -related transcription factor (CDBP) mRNA, complete cds"; source: *Mesembryanthemum crystallinum* (common iceplant).

NCBI acc. No. AI440657 (gi: 4283446) (Feb. 19, 1999); Shoemaker,R., et al. "sa63d09.y1 Gm-c1004 Glycine max cDNA clone Genome Systems Clone Id: Gm-c1004-3978 5' similar to TR:Q40476 Q40476 EREBP-1. ; , mRNA sequence"; source: *Glycine max* (soybean).

NCBI acc. No. AI442716 (gi: 4298124) (Feb. 19, 1999); Shoemaker,R., et al. "sa85d10.y1 Gm-c1004 Glycine max cDNA clone Genome Systems Clone Id: Gm-c1004-6092 5' similar to TR:O04680 O04680 PTI4. ;, mRNA sequence"; source: *Glycine max* (soybean); Title: "Public Soybean EST Project" (Unpublished (1999)).

NCBI acc. No. AI483782 (gi: 4387706) (Mar. 9, 1999); Alcala,J., et al. "EST249653 tomato ovary, TAMU *Lycopersicon esculentum* cDNA clone cLED23P13, mRNA sequence"; source: *Lycopersicon esculentum* (Solanum lycopersicum); Title: "Generation of ESTs from tomato carpel tissue" (Unpublished (1999)).

NCBI acc. No. AI483900 (gi: 4387824) (Mar. 9, 1999); Alcala,J., et al. "EST249771 tomato ovary, TAMU *Lycopersicon esculentum* cDNA clone cLED24L7, mRNA sequence"; source: *Lycopersicon esculentum* (Solanum lycopersicum); Title: "Generation of ESTs from tomato carpel tissue" (Unpublished (1999)).

NCBI acc. No. AI484961 (gi: 4380332) (Mar. 9, 1999); Alcala.J., et al. "EST243224 tomato ovary, TAMU *Lycopersicon esculentum* cDNA clone cLED2F21, mRNA sequence"; source: *Lycopersicon esculentum* (Solanum lycopersicum); Title: "Generation of ESTs from tomato carpel tissue" (Unpublished (1999)).

NCBI acc. No. AI485175 (gi: 4380546) (Mar. 9, 1999); Alcala.J., et al. "EST243479 tomato ovary, TAMU *Lycopersicon esculentum* cDNA clone cLED6D8, mRNA sequence"; source: *Lycopersicon esculentum* (Solanum lycopersicum); Title: "Generation of ESTs from tomato carpel tissue" (Unpublished (1999)).

NCBI acc. No. AI486689 (gi: 4382060) (Mar. 9, 1999); Alcala.J., et al. "EST245011 tomato ovary, TAMU *Lycopersicon esculentum* cDNA clone cLED11H4, mRNA sequence"; source: *Lycopersicon esculentum* (Solanum lycopersicum); Title: "Generation of ESTs from tomato carpel tissue" (Unpublished (1999)).

NCBI acc. No. AI487067 (gi: 4382438) (Mar. 9, 1999); Alcala.J., et al. "EST245389 tomato ovary, TAMU *Lycopersicon esculentum* cDNA clone cLED9C13, mRNA sequence"; source: *Lycopersicon esculentum* (Solanum lycopersicum); Title: "Generation of ESTs from tomato carpel tissue" (Unpublished (1999)).

NCBI acc. No. AI489709 (gi: 4385080) (Mar. 9, 1999); Alcala.J., et al. "EST248048 tomato ovary, TAMU *Lycopersicon esculentum* cDNA clone cLED14L13, mRNA sequence"; source: *Lycopersicon esculentum* (Solanum lycopersicum); Title: "Generation of ESTs from tomato carpel tissue" (Unpublished (1999)).

NCBI acc. No. AI495036 (gi: 4396039) (Mar. 11, 1999); Shoemaker,R., et al. "sa90a09.y1 Gm-c1004 *Glycine max* cDNA clone Genome Systems Clone Id: Gm-c1004-6545 5' similar to Tr:O22167 O22167 EREBP Isolog. ;, mRNA sequence"; source: *Glycine max* (soybean).

NCBI acc. No. AI496139 (gi: 4397142) (Mar. 11, 1999); Shoemaker,R., et al. "sa95h06.y1 Gm-c1004 *Glycine max* cDNA Clone Genome Systems Clone Id: Gm-c1004-7092 5' similar to SW:CDI3_ARATH P42736 Cadmium-Induced Protein AS30. ;, mRNA sequence"; source: *Glycine max* (soybean).

NCBI acc. No. AI771213 (gi: 5269350) (Jun. 29, 1999); Alcala.J., et al. "EST252409 tomato ovary, TAMU *Lycopersicon esculentum* cDNA clone cLED29K9, mRNA sequence"; source: *Lycopersicon esculentum* (Solanum lycopersicum); Title: "Generation of ESTs from tomato carpel tissue" (Unpublished (1999)).

NCBI acc. No. AI776626 (gi: 5274667) (Jun. 29, 1999); D Ascenzo,M., et al. "EST257726 tomato resistant, Cornell *Lycopersicon esculentum* cDNA clone cLER19A14, mRNA sequence"; source: *Lycopersicon esculentum* (*Solanum lycopersicum*).

NCBI acc. No. AI778693 (gi: 5276734) (Jun. 29, 1999); D Ascenzo,M., et al. "EST259572 tomato susceptible, Cornell *Lycopersicon esculentum* cDNA clone cLES6I9, mRNA sequence"; source: *Lycopersicon esculentum* (*Solanum lycopersicum*).

NCBI acc. No. AI781904 (gi: 5279945) (Jun. 29, 1999); D Ascenzo,M., et al. Title: "Generation of ESTs from *Pseudomonas* susceptible tomato" (Unpublished (1999)).

NCBI acc. No. AI782381 (gi: 5280422) (Jun. 29, 1999); D Ascenzo,M., et al. "EST263260 tomato susceptible, Cornell *Lycopersicon esculentum* cDNA clone cLES18P16, mRNA sequence"; source: *Lycopersicon esculentum* (*Solanum lycopersicum*).

NCBI acc. No. AI794657 (gi: 5342373) (Jul. 2, 1999); Shoemaker,R., et al. "sb67b03.y1 Gm-c1019 *Glycine max* cDNA clone Genome Systems Clone Id: Gm-c1019-6 5' similar to TR:Q40478 Q40478 EREBP-4. ;, mRNA sequence"; source: *Glycine max* (soybean); Title: "Public Soybean EST Project" (Unpublished (1999)).

NCBI acc. No. AI894873 (gi: 5600775) (Jul. 27, 1999); Alcala,J., et al. "EST264316 tomato callus, TAMU *Lycopersicon esculentum* cDNA clone cLEC6K7, mRNA sequence"; source: *Lycopersicon esculentum* (*Solanum lycopersicum*); Title: "Generation of ESTs from tomato callus tissue" (Unpublished (1999)).

NCBI acc. No. AI896308 (gi: 5602210) (Jul. 27, 1999); Alcala,J., et al. "EST265751 tomato callus, TAMU *Lycopersicon esculentum* cDNA clone cLEC14N19, mRNA sequence"; source: *Lycopersicon esculentum* (*Solanum lycopersicum*); Title: "Generation of ESTs from tomato callus tissue" (Unpublished (1999)).

NCBI acc. No. AI897797 (gi: 5603699) (Jul. 27, 1999); Alcala,J., et al. "EST267240 tomato ovary, TAMU *Lycopersicon esculentum* cDNA clone cLED30P1, mRNA sequence"; source: *Lycopersicon esculentum* (*Solanum lycopersicum*); Title: "Generation of ESTs from tomato carpel tissue" (Unpublished (1999)).

NCBI acc. No. AI897834 (gi: 5603736) (Jul. 27, 1999); Alcala,J., et al. "EST267277 tomato ovary, TAMU *Lycopersicon esculentum* cDNA clone cLED30F18, mRNA sequence"; source: *Lycopersicon esculentum* (*Solanum lycopersicum*); Title: "Generation of ESTs from tomato carpel tissue" (Unpublished (1999)).

NCBI acc. No. AI899000 (gi: 5604902) (Jul. 27, 1999); Alcala,J., et al. "EST268443 tomato ovary, TAMU *Lycopersicon esculentum* cDNA clone cLED36J9, mRNA sequence"; source: *Lycopersicon esculentum* (*Solanum lycopersicum*); Title: "Generation of ESTs from tomato carpel tissue" (Unpublished (1999)).

NCBI acc. No. AI899889 (gi: 5605791) (Jul. 27, 1999); Shoemaker,R., et al. "sb94g05.y1 Gm-c1017 Glycine max cDNA clone Genome Systems Clone Id: Gm-c1017-1137 5' similar to TR:Q40478 Q40478 EREBP-4. ; , mRNA sequence"; source: *Glycine max* (soybean).

NCBI acc. No. AI965917 (gi: 5760554) (Aug. 23, 1999); Shoemaker,R., et al. Title: "Public Soybean EST Project" (Unpublished (1999)).

NCBI acc. No. AI967551 (gi: 5762854) (Aug. 24, 1999); Poulsen,C., et al. Title: "Expressed sequence tags from *Mesorhizobium loti* infected roots of *Lotus japonicus*" (Unpublished (1999)).

NCBI acc. No. AI973653 (gi: 5770479) (Aug. 25, 1999); Shoemaker,R., et al. "sd07h05.y1 Gm-c1020 Glycine max cDNA clone Genome Systems Clone Id: Gm-c1020-1042 5' similar to TR:O22167 O22167 EREBP ISOLOG. ;, mRNA sequence"; source: *Glycine max* (soybean).

NCBI acc. No. AI997809 (gi: 5844714) (Sep. 8, 1999); Chen,J., et al. "701670827 A. thaliana, Columbia Col-0,rosette-1 *Arabidopsis thaliana* cDNA clone 701670827, mRNA sequence"; source: *Arabidopsis thaliana* (thale cress).

NCBI acc. No. AJ238740 (gi: 8346774) (Jun. 7, 2000); Menke,F.L. H., et al. "A jasmonate- and elicitor-responsive element in the periwinkle secondary metabolite biosynthetic gene Str interacts with a jasmonate- and elicitor-inducible AP2-domain transcription factor, ORCA2" (Unpublished).

NCBI acc. No. AJ251249 (gi: 8980312) (Jul. 8, 2000); van der Fits,L., et al. "Catharanthus roseus mRNA for AP2-domain DNA-binding protein (orca3 gene)"; source: *Catharanthus roseus* (*Madagascar periwinkle*).

NCBI acc. No. AJ251250 (gi: 8980314) (Jul. 8, 2000); van der Fits,L., et al. "*Catharanthus roseus* orca3 gene for AP2-domain DNA-binding protein"; source: *Catharanthus roseus* (*Madagascar periwinkle*).

NCBI acc. No. AJ299252 (gi: 10798643) (Oct. 11, 2000); Shen,W. H., et al. "*Nicotiana tabacum* partial mRNA for AP2 domain-containing transcription factor (ap2 gene)"; source: *Nicotiana tabacum* (common tobacco).

NCBI acc. No. AJ307662 (gi: 14140112) (May 17, 2001); Mayer,K., et al. "*Oryza sativa* genomic DNA fragment, chromosome 2"; source: *Oryza sativa*.

NCBI acc. No. AL374803 (gi: 9674555) (Aug. 3, 2000); Journet,E.P., et al. "MtBB09D02F1 MtBB *Medicago truncatula* cDNA clone MtBB09D02 T3, mRNA sequence"; source: *Medicago truncatula* (barrel medic).

NCBI acc. No. AL378570 (gi: 9678322) (Aug. 3, 2000); Journet,E.P., et al. "MtBB39B01F1 MtBB *Medicago truncatula* cDNA clone MtBB39B01 T3, mRNA sequence"; source: *Medicago truncatula* (barrel medic).

NCBI acc. No. AL381730 (gi: 9681481) (Aug. 3, 2000); Journet,E.P., et al. "MtBC02F03F3 MtBC *Medicago truncatula* cDNA clone MtBC02F03 T3, mRNA sequence"; source: *Medicago truncatula* (barrel medic); Title: "*Medicago truncatula* ESTs from endomycorrhizal roots" (Unpublished (2000)).

NCBI acc. No. AL387924 (gi: 9687675) (Aug. 3, 2000); Journet,E.P., et al. "MtBC45F03F1 MtBC *Medicago truncatula* cDNA clone MtBC45F03 T3, mRNA sequence"; source: *Medicago truncatula* (barrel medic); Title: "*Medicago truncatula* ESTs from endomycorrhizal roots" (Unpublished (2000)).

NCBI acc. No. AL388234 (gi: 9687985) (Aug. 3, 2000); Journet,E.P., et al. "MtBC47D08F1 MtBC Medicago truncatula cDNA clone MtBC47D08 T3, mRNA sequence"; source: *Medicago truncatula* (barrel medic); Title: "*Medicago truncatula* ESTs from endomycorrhizal roots" (Unpublished (2000)).

NCBI acc. No. AL513404 (gi: 12711302) (Feb. 7, 2001); Salse,J., et al. "*Oryza sativa* chromosome 12 clone OSJNBa0041K23, * Sequencing in Progress *"; source: *Oryza sativa*; Title: "*Oryza sativa* chromosome 12 sequencing" (Unpublished).

NCBI acc. No. AL607006 (gi: 15799247) (Sep. 27, 2001); Han,B., et al. "*Oryza sativa* chromosome 4 clone OSJNBA0079A21, * Sequencing in Progress *"; source: *Oryza sativa*; Title: "Direct Submission" (Submitted (Jul. 28, 2000) Han Bin, National Center for Gene Research, Chinese Academy of.

NCBI acc. No. AP003237 (gi: 13027267) (Feb. 21, 2001); Sasaki,T., et al. "*Oryza sativa* chromosome 1 clone P0046E05, * Sequencing in Progress *"; source: *Oryza sativa*; Title: "*Oryza sativa* nipponbare(GA3) genomic DNA, chromosome 1, PAC clone:P0046E05" (Published Only in DataBase (2001) in press).

NCBI acc. No. AP004676 (gi: 18447935) (Jan. 30, 2002); Sasaki,T., et al. "*Oryza sativa* chromosome 2 cloneOJ1003_B06, * Sequencing in Progress *"; source: *Oryza sativa*; Title: "*Oryza sativa* nipponbare(GA3) genomic DNA, chromosome 2, BAC clone:OJ1003_B06" (Published Only in Database (2002)).

NCBI acc. No. AC000106 (gi:1785951) (Jan. 21, 1997); Osborne, B.I., et al., "*Arabidopsis thaliana* chromosome 1" (note: two versions are presented for review, gi:1785951 submitted Jan. 21, 1997; and, gi:2342673 submitted Sep. 17, 1997).

NCBI acc. No. AU057740 (gi: 4716624) (Apr. 29, 1999); Yamamoto,K., et al. "AU057740 *Oryza sativa* mature leaf Nipponbare *Oryza sativa* japonica cultivar-group) cDNA clone S21744_1A, mRNA sequence"; source: *Oryza sativa* (japonica cultivar-group); Title: "Rice cDNA from mature leaf" (Unpublished (1999)).

NCBI acc. No. AU083387 (gi: 7273843) (Mar. 21, 2000); Sasaki,T., et al. "AU083387 Rice callus *Oryza sativa* (japonica cultivar-group) cDNA clone C52828, mRNA sequence"; source: *Oryza sativa* (japonica cultivar-group); Title: "Rice cDNA from callus (2000)" (Unpublished (2000)).

NCBI acc. No. AU083389 (gi: 7273845) (Mar. 21, 2000); Sasaki,T., et al. "AU083389 Rice callus *Oryza sativa* (japonica cultivar-group) cDNA clone C52843, mRNA sequence"; source: *Oryza sativa* (japonica cultivar-group); Title: "Rice cDNA from callus (2000)" (Unpublished (2000)).

NCBI acc. No. AU083516 (gi: 7273972) (Mar. 21, 2000); Sasaki,T., et al. "AU083516 Rice mature leaf *Oryza sativa* (japonica cultivar-group) cDNA clone S21744, mRNA sequence"; source: *Oryza sativa* (japonica cultivar-group); Title: "Rice cDNA from mature leaf (2000)" (Unpublished (2000)).

NCBI acc. No. AV422393 (gi: 7777209) (May 12, 2000); Asamizu,E., et al. Title: "Generation of 7137 non-redundant expressed sequence tags from a legume, *Lotus japonicus*" (DNA Res. 7 (2), 127-130 (2000)).

NCBI acc. No. AV422968 (gi: 7778405) (May 12, 2000); Asamizu,E., et al. Title: "Generation of 7137 non-redundant expressed sequence tags from a legume, *Lotus japonicus*" (DNA Res. 7 (2), 127-130 (2000)).

NCBI acc. No. AV423260 (gi: 7778996) (May 12 2000); Asamizu,E., et al. Title: "Generation of 7137 non-redundant expressed sequence tags from a legume, *Lotus japonicus*" (DNA Res. 7 (2), 127-130 (2000)).

NCBI acc. No. AV425560 (gi: 7783624) (May 12 2000); Asamizu,E., et al. Title: "Generation of 7137 non-redundant expressed sequence tags from a legume, *Lotus japonicus*" (DNA Res. 7 (2), 127-130 (2000)).

NCBI acc. No. AV552445 (gi: 8723858) (Jun. 26, 2000); Asamizu,E., et al. "A large scale analysis of cDNA in *Arabidopsis thaliana*: Generation of 12,028 non-redundant expressed sequence tags from normalized and size-selected cDNA libraries" (DNA Res. 7 (3), 175-180 (2000)).

NCBI acc. No. AW030009 (gi: 5888765) (Sep. 15, 1999); Alcala,J., et al. "EST273264 tomato callus, TAMU *Lycopersicon esculentum* cDNA clone cLEC11J16, mRNA sequence"; source: *Lycopersicon esculentum* (*Solanum lycopersicum*).

NCBI acc. No. AW030386 (gi: 5889142) (Sep. 15, 1999); Alcala,J., et al. "EST273641 tomato callus, TAMU *Lycopersicon esculentum* cDNA clone cLEC20I12, mRNA sequence"; source: *Lycopersicon esculentum* (*Solanum lycopersicum*).

NCBI acc. No. AW034216 (gi: 5892972) (Sep. 15, 1999); Alcala,J., et al. "EST277787 tomato callus, TAMU *Lycopersicon esculentum* cDNA clone cLEC32P18 similar to Pti4, mRNA sequence"; source: *Lycopersicon esculentum* (*Solanum lycopersicum*).

NCBI acc. No. AW093577 (gi: 6059172) (Oct. 18 ,1999); D'Ascenzo,M., et al. "EST286757 tomato mixed elicitor, BTI *Lycopersicon esculentum* cDNA clone cLET25E20, mRNA sequence"; source: *Lycopersicon esculentum* (*Solanum lycopersicum*).

NCBI acc. No. AW185128 (gi: 6454445) (Nov. 19, 1999); Shoemaker,R., et al. Title: "Public Soybean EST Project" (Unpublished (1999)).

NCBI acc. No. AW200919 (gi: 6481648) (Nov. 30, 1999); Shoemaker,R., et al. Title: "Public Soybean EST Project" (Unpublished (1999)).

NCBI acc. No. AW203601 (gi: 6502228) (Dec. 1, 1999); Shoemaker,R., et al. "sf36b02.y1 Gm-c1028 *Glycine max* cDNA clone Genome Systems Clone Id: Gm-c1028-2020 5' similar to TR:O23113 O23113 AP2 Domain Containing Protein RAP2.12 ;, mRNA sequence"; source: *Glycine max* (soybean).

NCBI acc. No. AW219198 (gi: 6530072) (Dec. 6, 1999); van der Hoeven,R.S., et al. "EST301680 tomato root during/after fruit set, Cornell University *Lycopersicon esculentum* cDNA clone cLEX3G6, mRNA sequence"; source: *Lycopersicon esculentum* (*Solanum lycopersicum*).

NCBI acc. No. AW220395 (gi: 6531269) (Dec. 6, 1999); van der Hoeven,R.S., et al. "EST302878 tomato root during/after fruit set, Cornell University *Lycopersicon esculentum* cDNA clone cLEX10F20, mRNA sequence"; source: *Lycopersicon esculentum* (*Solanum lycopersicum*).

NCBI acc. No. AW221854 (gi: 6533538) (Dec. 7, 1999); Alcala,J., et al. "EST298665 tomato fruit red ripe, TAMU *Lycopersicon esculentum* cDNA clone cLEN4I21, mRNA sequence"; source: *Lycopersicon esculentum* (*Solanum lycopersicum*); Title: "Generation of ESTs from tomato fruit tissue" (Unpublished (1999)).

NCBI acc. No. AW233956 (gi: 6566281) (Dec. 13, 1999); Shoemaker,R., et al. Title: "Public Soybean EST Project" (Unpublished (1999)).

NCBI acc. No. AW267820 (gi: 6654776) (Jan. 3, 2000); Fedorova,M., et al. Title: "ESTs from roots of *Medicago truncatula* after inoculation with *Phytophthora medicaginis*" (Unpublished (1999)).

NCBI acc. No. AW267914 (gi: 6654934) (Jan. 3, 2000); Fedorova,M., et al. Title: "ESTs from roots of *Medicago truncatula* after inoculation with *Phytophthora medicaginis*" (Unpublished (1999)).

NCBI acc. No. AW278190 (gi: 6666731) (Jan. 4, 2000); Shoemaker,R., et al. Title: "Public Soybean EST Project" (Unpublished (1999)).

NCBI acc. No. AW308784 (gi: 6724385) (Jan. 21, 2000); Shoemaker,R., et al. Title: "Public Soybean EST Project" (Unpublished (1999)).

NCBI acc. No. AW329209 (gi: 7675608) (Jan. 28, 2000); Harrison,M.J., et al. Title: "ESTs from phosphate starved roots" (Unpublished (1999)).

NCBI acc. No. AW348322 (gi: 6846032) (Feb. 1, 2000); Vodkin,L, et al. "GM210001B23F6 Gm-r1021 *Glycine max* cDNA clone Gm-r1021-276 3, mRNA sequence"; source: *Glycine max* (soybean); Title: "A FunctionalGenomics Program for Soybean (NSF 9872565)" (Unpublished (1999)).

NCBI acc. No. AW349516 (gi: 6847226) (Feb. 1, 2000); Vodkin,L, et al. Title: "A Functional Genomics Program for Soybean (NSF 9872565)" (Unpublished (1999)).

NCBI acc. No. AW349638 (gi: 6847348) (Feb. 1, 2000); Vodkin,L, et al. "GM210005B21A4 Gm-r1021 *Glycine max* cDNA clone Gm-r1021-1568 3', mRNA sequence"; source: *Glycine max* (soybean).

NCBI acc. No. AW396250 (gi: 6914720) (Feb. 7, 2000); Shoemaker,R., et al. Title: "Public Soybean EST Project" (Unpublished (1999)).

NCBI acc. No. AW441715 (gi: 6976966) (Feb. 14, 2000); Alcala,J., et al. Title: "Generation of ESTs from tomato fruit tissue" (Unpublished (1999)).

NCBI acc. No. AW443265 (gi: 6985447) (Feb. 17, 2000); D'Ascenzo,M., et al. Title: "Generation of ESTs from tomato callus (mixed elicitor)" (Unpublished (1999)).

NCBI acc. No. AW507898 (gi: 7145976) (Mar. 3, 2000); Shoemaker,R., et al. Title: "Public Soybean EST Project" (Unpublished (1999)).

NCBI acc. No. AW507860 (gi: 7145938) (Mar. 3, 2000); Shoemaker,R., et al. Title: "Public Soybean EST Project" (Unpublished (1999)).

NCBI acc. No. AW559315 (gi: 7204741) (Mar. 7, 2000); Fedorova,M., et al. "EST306358 DSIR *Medicago truncatula* cDNA clone pDSIR-2515, mRNA sequence"; source: *Medicago truncatula* (barrel medic); Title: "ESTs from roots of *Medicago truncatula* after inoculation with *Phytophthora medicaginis*" (Unpublished (1999)).

NCBI acc. No. AW559329 (gi: 7204755) (Mar. 7, 2000); Fedorova,M., et al. "EST306372 DSIR *Medicago truncatula*cDNA clone pDSIR-25K15, mRNA sequence"; source: *Medicago truncatula* (barrel medic); Title: "ESTs from roots of *Medicago truncatula* after inoculation with *Phytophthora medicaginis*" (Unpublished (1999)).

NCBI acc. No. AW559374 (gi: 7204800) (Mar. 7, 2000); Fedorova,M., et al. "EST314422 DSIR *Medicago truncatula* cDNA clone pDSIR-7J9, mRNA sequence"; source: *Medicago truncatula* (barrel medic); Title: "ESTs from roots of *Medicago truncatula* after inoculation with *Phytophthora medicaginis*" (Unpublished (1999)).

NCBI acc. No. AW560196 (gi: 7205622) (Mar. 7, 2000); Fedorova,M., et al. "EST315244 DSIR *Medicago truncatula* cDNA clone pDSIR-26K12, mRNA sequence"; source: *Medicago truncatula* (barrel medic); Title: "ESTs from roots of *Medicago truncatula* after inoculation with *Phytophthora medicaginis*" (Unpublished (1999)).

NCBI acc. No. AW560968 (gi: 7206394) (Mar. 7, 2000); Fedorova,M., et al. "EST316016 DSIR *Medicago truncatula* cDNA clone pDSIR-30N21, mRNA sequence"; source: *Medicago truncatula* (barrel medic); Title: "ESTs from roots of *Medicago truncatula* after inoculation with *Phytophthora medicaginis*" (Unpublished (1999)).

NCBI acc. No. AW574222 (gi: 7238955) (Mar. 13, 2000); Fedorova,M., et al. "EST316813 GVN *Medicago truncatula* cDNA clone pGVN-52B10, mRNA sequence"; source: *Medicago truncatula* (barrel medic); Title: "ESTs from one month old nitrogen-fixing root nodules of *Medicago truncatula*" (Unpublished (2000)).

NCBI acc. No. AW596384 (gi: 7283781) (Mar. 22, 2000); Shoemaker,R., et al. "sj02f12.y1 Gm-c1032 *Glycine max* cDNA clone Genome Systems Clone Id: Gm-c1032-744 5' similar to Tr:Q40478 Q40478 EREBP-4. ;,mRNA sequence"; source: *Glycine max* (soybean); Title: "Public Soybean EST Project" (Unpublished (1999)).

NCBI acc. No. AW618245 (gi: 7324479) (Mar. 24, 2000); Alcala,J., et al. Title: "Generation of ESTs from wild tomato (*Lycopersicon pennellii*) trichomes" (Unpublished (1999)).

NCBI acc. No. AW618246 (gi: 7324480) (Mar. 24, 2000); Alcala,J., et al. Title: "Generation of ESTs from wild tomato (*Lycopersicon pennellii*) trichomes" (Unpublished (1999)).

NCBI acc. No. AW620490 (gi: 7326692) (Mar. 24, 2000); Shoemaker,R., et al. Title: "Public Soybean EST Project" (Unpublished (1999)).

NCBI acc. No. AW685799 (gi: 7560535) (Apr. 14, 2000); Watson,B. S., et al. Title: "Expressed Sequence Tags from the Samuel Roberts Noble Foundation *Medicago truncatula* nodulated root library" (Unpublished (2000)).

NCBI acc. No. AW686013 (gi: 11930899) (Apr. 14, 2000); Watson,B.S., et al. Title: "Expressed Sequence Tags from the Samuel Roberts Noble Foundation *Medicago truncatula* nodulated root library" (Unpublished (2000)).

NCBI acc. No. AW759181 (gi: 7691047) (May 4, 2000); Shoemaker,R., et al. Title: "Public Soybean EST Project" (Unpublished (1999)).

NCBI acc. No. AW760204 (gi: 7692089) (May 4, 2000); Shoemaker,R., et al. Title: "Public Soybean EST Project" (Unpublished (1999)).

NCBI acc. No. AW774176 (gi: 7718021) (May 8, 2000); VandenBosch,K., et al. Title: "ESTs from roots of *Medicago truncatula* after *Rhizobium* inoculation" (Unpublished (1999)).

NCBI acc. No. AW775590 (gi: 7765403) (May 9, 2000); Fedorova,M., et al. "EST334655 DSIL *Medicago truncatula* cDNA clone pDSIL-2C16, mRNA sequence"; source: *Medicago truncatula* (barrel medic); Title: "ESTs from leaves of *Medicago truncatula* after inoculation with *Colletotrichum trifolii*" (Unpublished (2000)).

NCBI acc. No. AW776668 (gi: 7766481) (May 9, 2000); Fedorova,M., et al. "EST335733 DSIL *Medicago truncatula* cDNA clone pDSIL-13B14, mRNA sequence"; source: *Medicago truncatula* (barrel medic); Title: "ESTs from leaves of *Medicago truncatula* after inoculation with *Colletotrichum trifolii*" (Unpublished (2000)).

NCBI acc. No. AW776671 (gi: 7766484) (May 9, 2000); Fedorova,M., et al. "EST335736 DSIL *Medicago truncatula* cDNA clone pDSIL-13B22, mRNA sequence"; source: *Medicago truncatula* (barrel medic); Title: "ESTs from leaves of *Medicago truncatula* after inoculation with *Colletotrichum trifolii*" (Unpublished (2000)).

NCBI acc. No. AW781602 (gi: 7796205) (May 12, 2000); Shoemaker,R., et al. Title: "Public Soybean EST Project" (Unpublished (1999)).

NCBI acc. No. AW782252 (gi: 7796858) (May 12, 2000); Shoemaker,R., et al. "sm03d11.y1 Gm-c1027 *Glycine max* cDNA clone Genome Systems Clone Id: Gm-c1027-7822 5' similar to TR:P93007 P93007 Cadmium-Induced Protein Isolog. ;, mRNA sequence"; source: *Glycine max* (soybean).

NCBI acc. No. AW840611 (gi: 7934594) (May 18, 2000); Anderson,J.V., et al. Title: "Identification of mRNAs expressed in underground adventitious buds of *Euphorbia esula* (leafy spurge)" (Unpublished (2000)).

NCBI acc. No. AW980481 (gi: 8172016) (Jun. 2, 2000); Fedorova,M., et al. "EST391634 GVN *Medicago truncatula* cDNA clone pGVN-30P6, mRNA sequence"; source: *Medicago truncatula* (barrel medic); Title: "ESTs from one month old nitrogen-fixing root nodules of *Medicago truncatula*" (Unpublished (2000)).

NCBI acc. No. AW980654 (gi: 8172193) (Jun. 2, 2000); Fedorova,M., et al. "EST391807 GVN *Medicago truncatula* cDNA clone pGVN-55D7, mRNA sequence"; source: *Medicago truncatula* (barrel medic); Title: "ESTs from one month old nitrogen-fixing root nodules of *Medicago truncatula*" (Unpublished (2000)).

NCBI acc. No. AW981151 (gi: 8172743) (Jun. 2, 2000); Fedorova,M., et al. "EST392345 DSIL *Medicago truncatula* cDNA clone pDSIL-12I11, mRNA sequence"; source: *Medicago truncatula* (barrel medic); Title: "ESTs from leaves of *Medicago truncatula* after inoculation with *Colletotrichum trifolii*" (Unpublished (2000)).

NCBI acc. No. AW981228 (gi: 8172715) (Jun. 2, 2000); Fedorova,M., et al. "EST392318 DSIL *Medicago truncatula* cDNA clone pDSIL-12C23, mRNA sequence"; source: *Medicago truncatula* (barrel medic); Title: "ESTs from leaves of *Medicago truncatula* after inoculation with *Colletotrichum trifolii*" (Unpublished (2000)).

NCBI acc. No. AW981323 (gi: 8172882) (Jun. 2, 2000); Fedorova,M., et al. "EST392476 DSIL *Medicago truncatula* cDNA clone pDSIL-12B14, mRNA sequence"; source: *Medicago truncatula* (barrel medic); Title: "ESTs from leaves of *Medicago truncatula* after inoculation with *Colletotrichum trifolii*" (Unpublished (2000)).

NCBI acc. No. AX033191 (gi: 10280046) (Sep. 22, 2000); Memelink,J., et al. "Sequence 2 from Patent WO0046383"; source: *Catharanthus roseus* (Madagascar periwinkle); Title: "Method of modulating metabolite biosynthesis in recombinant cells".

NCBI acc. No. AX033192 (gi: 10280047) (Sep. 22, 2000); Memelink,J., et al. "Sequence 3 from Patent WO0046383"; source: *Catharanthus roseus* (Madagascar periwinkle); Title: "Method of modulating metabolite biosynthesis in recombinant cells".

NCBI acc. No. AY192367 (gi: 28274827) (Feb. 9, 2003); Tournier,B., et al. "*Lycopersicon esculentum* ethylene response factor 1 (ERF1) mRNA, complete cds"; source: *Lycopersicon esculentum* (tomato); Title: LeERF2 defines a novel class of ethylene response factors and confers enhanced tolerance to cold stress when . . . .

NCBI acc. No. BAA07321 (gi: 1208495) (Feb. 28, 1996); Ohme-Takagi,M., et al. "EREBP-1"; source: *Nicotiana tabacum* (common tobacco).

NCBI acc. No. BAA07322 (gi: 1208496) (Feb. 28, 1996); Ohme-Takagi,M., et al. "EREBP-3"; source: *Nicotiana tabacum* (common tobacco).

NCBI acc. No. BAA07323 (gi: 1208497) (Feb. 28, 1996); Ohme-Takagi,M., et al. "EREBP-4"; source: *Nicotiana tabacum* (common tobacco); Title: "Direct Submission" (Submitted (Sep 1, 1994).

NCBI acc. No. BAA07324 (gi: 1208498) (Feb. 28, 1996); Ohme-Takagi et al. "EREBP-2"; source: *Nicotiana tabacum* (common tobacco); Title: "Direct Submission" (Submitted (Sep. 1, 1994).

NCBI acc. No. BAA76734 (gi: 4587373) (Apr. 17, 1999); Hirata,T., et al. "ethylene responsive element binding factor [*Nicotiana tabacum*]"; source: *Nicotiana tabacum* (common tobacco); Title: "Probable ethylene responsive element binding factor".

NCBI acc. No. BAA78738 (gi: 5091503) (Jun. 17, 1999); Sasaki,T., et al. "EST AU055776(S20048) corresponds to a region of the predicted gene.; Similar to *Arabidopsis thaliana* AP2 domain containing protein RAP2.10 mRNA, partial cds.(AF003103) [*Oryza sativa*]"; source: *Oryza sativa*.

NCBI acc. No. BAA81845 (gi: 5295944) (Jun. 30, 1999); Sasaki,T., et al. "Similar to *Nicotiana tabacum* mRNA for ERF1, complete cds.(D38123) [*Oryza sativa*]"; source: *Oryza sativa*.

NCBI acc. No. BAA87068 (gi: 6478845) (Nov. 30, 1999); Ashida,Y., et al. "ethylene-responsive element binding protein1 homolog [*Matricaria chamomilla*]"; source: *Matricaria chamomilla*.

NCBI acc. No. BAA94514 (gi: 7573605) (Apr. 14, 2000); Sasaki,T., et al. "Similar to *Arabidopsis thaliana* chromosome 4, BAC clone F9D16; putative Ap2 domain protein (AL035394) [*Oryza sativa*]"; source: *Oryza sativa*; Title: "*Oryza sativa* nipponbare(GA3) genomic DNA, chromosome 1, PAC clone:P0443E05".

NCBI acc. No. BAA97122 (gi: 8809571) (Jun. 28, 2000); Kitajima et al. "ethylene-responsive element binding factor [*Nicotiana sylvestris*]"; source: *Nicotiana sylvestris* (wood tobacco); Title: "Characterization of gene expression of NsERFs, transcription factors of basic PR genes from *Nicotiana sylvestris*" (Plant Cell Physiol. 41, 817-824).

NCBI acc. No. BAA97123 (gi: 8809573) (Jun. 28, 2000); Kitajima et al. "ethylene-responsive element binding factor [*Nicotiana sylvestris*]"; source: *Nicotiana sylvestris* (wood tobacco); Title: "Characterization of gene expression of NsERFs, transcription factors of basic PR genes from *Nicotiana sylvestris*" (Plant Cell Physiol. 41, 817-824).

NCBI acc. No. BAA97124 (gi: 8809575) (Jun. 28, 2000); Kitajima et al. "ethylene-responsive element binding factor [*Nicotiana sylvestris*]"; source: *Nicotiana sylvestris* (wood tobacco); Title: "Characterization of gene expression of NsERFs, transcription factors of basic PR genes from *Nicotiana sylvestris*" (Plant Cell Physiol. 41, 817-824).

NCBI acc. No. BAB03248 (gi: 9309342) (Jul. 20, 2000); Ohta,M., et al. "ethylene responsive element binding factor3 [*Oryza sativa*]"; source: *Oryza sativa*; Title: "Novel transcriptional repression in plants" (Unpublished (2000)).

NCBI acc. No. BAB07908 (gi: 9711804) (Aug. 6, 2000); Sasaki,T., et al. "hypothetical protein [*Oryza sativa*]"; source: *Oryza sativa*; Title: "*Oryza sativa* nipponbare(GA3) genomic DNA, chromosome 1, PAC clone:P0417G05" (Published Only in DataBase (2000) in press).

NCBI acc. No. BAB16083 (gi: 10567106) (Oct. 3, 2000); Ohta,M., et al. "osERF3 [*Oryza sativa*]"; source: *Oryza sativa*; Title: "A nobel repression domain of class II ERF transcriptional repressors" (Unpublished (2000)).

NCBI acc. No. BAB63735 (gi: 15290041) (Aug. 24, 2001); Sasaki,T., et al. "hypothetical protein [*Oryza sativa*]"; source: *Oryza sativa*; Title: "*Oryza sativa* nipponbare(GA3) genomic DNA, chromosome 1, PAC clone: P0694A04" (Published Only in Database (2001) in press).

NCBI acc. No. BE022152 (gi: 8284584) (Jun. 6, 2000); Shoemaker,R., et al. "sm68b06.y1 Gm-c1028 *Glycine max* cDNA clone Genome Systems Clone Id: Gm-c1028-9036 5&apos similar to TR:O23105 O23105 AP2 DOMAIN Containing Protein RAP2.3. ;, mRNA sequence"; source: *Glycine max* (soybean).

NCBI acc. No. BE024062 (gi: 8286503) (Jun. 6, 2000); Shoemaker,R., et al. "sm96c01.y1 Gm-c1015 *Glycine max* cDNA clone Genome Systems Clone Id: Gm-c1015-7897 5' similar to TR:O23105 O23105 AP2 Domain Containing Protein RAP2.3. ;, mRNA sequence"; source: *Glycine max* (soybean).

NCBI acc. No. BE203165 (gi: 8746436) (Jun. 27, 2000); VandenBosch,K., et al. "EST403187 KV1 *Medicago truncatula* cDNA clone pKV1-4L15, mRNA sequence"; source: *Medicago truncatula* (barrel medic); Title: "ESTs from roots of *Medicago truncatula* 24 hours after inoculation with *Sinorhizobium meliloti*" (Unpublished (1999)).

NCBI acc. No. BE203296 (gi: 8746567) (Jun. 27, 2000); VandenBosch,K., et al. "EST403318 KV1 *Medicago truncatula* cDNA clone pKV1-5G15, mRNA sequence"; source: *Medicago truncatula* (barrel medic); Title: "ESTs from roots of *Medicago truncatula* 24 hours after inoculation with *Sinorhizobium meliloti* " (Unpublished (1999)).

NCBI acc. No. BE318516 (gi: 11960607) (Jul. 14, 2000); Torres-Jerez,I., et al. "NF071G07LF1F1053 Developing leaf *Medicago truncatula* cDNA clone NF071G07LF 5', mRNA sequence"; source: *Medicago truncatula* (barrel medic).

NCBI acc. No. BE325359 (gi: 11935917) (Jul. 14, 2000); He,X.-Z., et al. "NF087B10ST1F1077 Developing stem *Medicago truncatula* cDNA clone NF087B10ST 5', mRNA sequence"; source: *Medicago truncatula* (barrel medic).

NCBI acc. No. BE326131 (gi: 11934119) (Jul. 14, 2000); He,X.-Z., et al. "NF085C08ST1F1055 Developing stem *Medicago truncatula* cDNA clone NF085C08ST 5', mRNA sequence"; source: *Medicago truncatula* (barrel medic).

NCBI acc. No. BE414448 (gi: 9412294) (Jul. 24, 2000); Anderson,O. A., et al. "International Triticeae EST Cooperative (ITEC): Production of Expressed Sequence Tags for Species of the Triticeae" (Unpublished (2000)).

NCBI acc. No. BE419451 (gi: 9417297) (Jul. 24, 2000); Anderson,O. A., et al. "WWS012.C2R000101 ITEC WWS Wheat Scutellum Library *Triticum aestivum* cDNA clone WWS012.C2, mRNA sequence"; source: *Triticum aestivum* (bread wheat).

NCBI acc. No. BE419533 (gi: 9417379) (Jul. 24, 2000); Anderson,O. A., et al. "WWS014.C1 R000101 ITEC WWS Wheat Scutellum Library *Triticum aestivum* cDNA clone WWS014.C1, mRNA sequence"; source: *Triticum aestivum* (bread wheat).

NCBI acc. No. BE421461 (gi: 9419304) (Jul. 24, 2000); Anderson,O. A., et al. "HWM009.E10 ITEC HWM Barley Leaf Library *Hordeum vulgare* subsp. vulgare cDNA clone HWM009.E10, mRNA sequence"; source: *Hordeum vulgare* subsp. vulgare.

NCBI acc. No. BE427272 (gi: 9425115) (Jul. 24, 2000); Anderson,O. A, et al. "PSR6192 ITEC PSR Wheat Pericarp/Testa Library *Triticum aestivum* cDNA clone PSR6192, mRNA sequence"; source: *Triticum aestivum* (bread wheat).

NCBI acc. No. BE427520 (gi: 9425363) (Jul. 24, 2000); Anderson,O. A., et al. "PSR7136 ITEC PSR Wheat Pericarp/Testa Library *Triticum aestivum* cDNA clone PSR7136, mRNA sequence"; source: *Triticum aestivum* (bread wheat).

NCBI acc. No. BE429439 (gi: 9427282) (Jul. 24, 2000); Anderson,O. A., et al. "TAS000.B08R990618 ITEC TAS Wheat cDNA Library Triticum aestivum cDNA clone TAS000.B08, mRNA sequence"; source: *Triticum aestivum* (bread wheat).

NCBI acc. No. BE429874 (gi: 9427717) (Jul. 24, 2000); Anderson,O. A., et al. "TAS004.F11R990617 ITEC TAS Wheat cDNA Library Triticum aestivum cDNA clone TAS004.F11, mRNA sequence"; source: *Triticum aestivum* (bread wheat).

NCBI acc. No. BE432465 (gi: 9430308) (Jul. 24, 2000); Alcala,J., et al. "EST398994 tomato breaker fruit, TIGR *Lycopersicon esculentum* cDNA clone cLEG8I18, mRNA sequence"; source: *Lycopersicon esculentum* (*Solanum lycopersicum*); Title: "Generation of ESTs from tomato fruit tissue, breaker stage" (Unpublished (2000)).

NCBI acc. No. BE433462 (gi: 9431305) (Jul. 24, 2000); Alcala,J., et al. "EST399991 tomato breaker fruit, TIGR *Lycopersicon esculentum* cDNA clone cLEG14M13, mRNA sequence"; source: *Lycopersicon esculentum* (*Solanum lycopersicum*); Title: "Generation of ESTs from tomato fruit tissue, breaker stage" (Unpublished (2000)).

NCBI acc. No. BE435827 (gi: 9433670) (Jul. 24, 2000); Alcala,J., et al. "EST406905 tomato breaker fruit, TIGR *Lycopersicon esculentum* cDNA clone cLEG29O9, mRNA sequence"; source: *Lycopersicon esculentum* (*Solanum lycopersicum*); Title: "Generation of ESTs from tomato fruit tissue, breaker stage" (Unpublished (2000)).

NCBI acc. No. BE436333 (gi: 9434176) (Jul. 24, 2000); Alcala,J., et al. "EST407411 tomato breaker fruit, TIGR *Lycopersicon esculentum* cDNA clone cLEG32E7, mRNA sequence"; source: *Lycopersicon esculentum* (*Solanum lycopersicum*); Title: "Generation of ESTs from tomato fruit tissue, breaker stage" (Unpublished (2000)).

NCBI acc. No. BE436391 (gi: 9434234) (Jul. 24, 2000); Alcala,J., et al. "EST407469 tomato breaker fruit, TIGR *Lycopersicon esculentum* cDNA clone cLEG32A16, mRNA sequence"; source: *Lycopersicon esculentum* (*Solanum lycopersicum*); Title: "Generation of ESTs from tomato fruit tissue, breaker stage" (Unpublished (2000)).

NCBI acc. No. BE436556 (gi: 9434399) (Jul. 24, 2000); Alcala,J., et al. "EST407634 tomato breaker fruit, TIGR *Lycopersicon esculentum* cDNA clone CLEG33I3, mRNA sequence"; source: *Lycopersicon esculentum* (*Solanum lycopersicum*); Title: "Generation of ESTs from tomato fruit tissue, breaker stage" (Unpublished (2000)).

NCBI acc. No. BE449351 (gi: 9454770) (Jul. 26, 2000); van der Hoeven,R.S., et al. "EST340367 L. hirsutum trichome, Cornell University *Lycopersicon hirsutum* cDNA clone cLHT28N22, mRNA sequence"; source: *Lycopersicon hirsutum* (*Solanum habrochaites*).

NCBI acc. No. BE449392 (gi: 9454895) (Jul. 26, 2000); van der Hoeven,R.S., et al. "EST356151 L. hirsutumtrichome, Cornell University *Lycopersicon hirsutum* cDNA clone cLHT31 K6, mRNA sequence"; source: *Lycopersicon hirsutum* (*Solanum habrochaites*).

NCBI acc. No. BE454507 (gi: 13189310) (Jul. 26, 2000); Wing,R., et al. Title: "Development of a genetically and physically anchored EST resource for barley genomics: Morex 5-45 DAP spike cDNA library" (Unpublished(2001)).

NCBI acc. No. BE459781 (gi: 9504083) (Jul. 27, 2000); Alcala,J., et al. "Generation of ESTs from tomato fruit tissue, immature green" (Unpublished (2000)).

NCBI acc. No. BE492864 (gi: 9659457) (Aug. 2, 2000); Anderson,O.D., et al. "The structure and function of the expressed portion of the wheat genomes—Vegetative apex cDNA library from *Triticum monococcum*" (Unpublished (2001)).

NCBI acc. No. BE522812 (gi: 9780790) (Aug. 9, 2000); White,J.A., et al. "A new set of *Arabidopsis* expressed sequence tags from developing seeds. The metabolic pathway from carbohydrates to seed oil" (Plant Physiol. 124(4), 1582-1594 (2000)).

NCBI acc. No. BE554847 (gi: 9819334) (Aug. 15, 2000); Shoemaker,R., et al."Public Soybean EST Project" (Unpublished (1999)).

NCBI acc. No. BE554898 (gi: 9819385) (Aug. 15, 2000); Shoemaker,R., et al. "Public Soybean EST Project" (Unpublished (1999)).

NCBI acc. No. BE610114 (gi: 9901146) (Aug. 24, 2000); Shoemaker,R., et al. "sp80h02.y1 Gm-c1044 *Glycine max* cDNA clone Genome Systems Clone Id: Gm-c1044-2284 5' similar to TR:Q40478 Q40478 EREBP-4. ;, mRNA sequence"; source: *Glycine max* (soybean).

NCBI acc. No. BE637157 (gi: 9920268) (Aug. 25, 2000); Anderson,O.D., et al. "WHE1806_H12_O24ZS *Secale cereale* anther cDNA library *Secale cereale* cDNA clone WHE1806_H12_O24, mRNA sequence"; source: *Secale cereale* (rye).

NCBI acc. No. BE642320 (gi: 9959995) (Sep. 1, 2000); Salmi,M.L., et al. Title: "Profile and analysis of gene expression changes during early development in germinating spores of *Ceratopteris richardii*" (Plant Physiol. 138(3), 1734-1745 (2005)).

NCBI acc. No. BE661059 (gi: 9986951) (Sep. 6, 2000); Harris,N., et al. "1263 GmaxSC *Glycine max* cDNA, mRNA sequence"; source: *Glycine max* (soybean); Title: "Gene expression in developing soybean seed coats" (Unpublished (2000)).

NCBI acc. No. BE804185 (gi: 10235238) (Sep. 20, 2000); Shoemaker,R., et al. "Public Soybean EST Project" (Unpublished (1999)).

NCBI acc. No. BE804368 (gi: 10235480) (Sep. 20, 2000); Shoemaker,R., et al. "sr78h05.y1 Gm-c1052 *Glycine max* cDNA clone Genome Systems Clone Id: Gm-d052-1906 5' similar to TR:Q40478 Q40478 EREBP-4. ;, mRNA sequence"; source: *Glycine max* (soybean).

NCBI acc. No. BE805304 (gi: 10236416) (Sep. 20, 2000); Shoemaker,R., et al. "ss40h06.y1 Gm-c1061 *Glycine max* cDNA clone Genome Systems Clone Id: Gm-c1061-1236 5' similar to TR:Q40478 Q40478 EREBP-4.;, mRNA sequence"; source: *Glycine max* (soybean).

NCBI acc. No. BE820195 (gi: 10252429) (Sep. 21, 2000); Vodkin,L., et al. "GM700006A11G12 Gm-r1070 *Glycine max* cDNA clone Gm-r1070-2231 3', mRNA sequence"; source: *Glycine max* (soybean); Title: "A Functional Genomics Program for Soybean (NSF 9872565)" (Unpublished (1999)).

NCBI acc. No. BE917882 (gi: 10420430) (Sep. 29, 2000); Cordonnier-Pratt,M.-M., et al. "OV1_7_C07.b1_A002 Ovary 1 (OV1) *Sorghum bicolor* cDNA, mRNA sequence"; source: *Sorghum bicolor* (sorghum); Title: "An EST database from Sorghum: ovaries of varying immature stages" (Unpublished (2000)).

NCBI acc. No. BE942996 (gi: 10520755) (Oct. 3, 2000); Cote,F., et al. Title: "ESTs from seedling roots of *Medicago truncatula* after treatment with beta glucan elicitor preparation from *Phytophthora sojae*" (Unpublished (2000)).

NCBI acc. No. BF006068 (gi: 10706343) (Oct. 6, 2000); Fedorova,M., et al. "EST434566 DSLC *Medicago truncatula* cDNA clone pDSLC-39F7, mRNA sequence"; source: *Medicago truncatula* (barrel medic); Title: "ESTs from *Medicago truncatula* leaves and cotyledons" (Unpublished (2000)).

NCBI acc. No. BF006539 (gi: 10706814) (Oct. 6, 2000); Fedorova,M., et al. "EST435037 DSLC *Medicago truncatula* cDNA clone pDSLC-41 L18, mRNA sequence"; source: *Medicago truncatula* (barrel medic); Title: "ESTs from *Medicago truncatula* leaves and cotyledons" (Unpublished (2000)).

NCBI acc. No. BF096818 (gi: 10902528) (Oct. 19, 2000); van der Hoeven,R.S., et al. "EST360845 tomato nutrient deficient roots *Lycopersicon esculentum* cDNA clone cLEW17I10 5' sequence, mRNA sequence"; source: *Lycopersicon esculentum* (*Solanum lycopersicum*).

NCBI acc. No. BF112878 (gi: 10942568) (Oct. 20, 2000); Alcala,J., et al. "EST440468 tomato breaker fruit *Lycopersicon esculentum* cDNA clone cLEG42N7 5' sequence, mRNA sequence"; source: *Lycopersicon esculentum* (*Solanum lycopersicum*).

NCBI acc. No. BF113172 (gi: 10942862) (Oct. 20, 2000); Alcala,J., et al. "EST440762 tomato breaker fruit *Lycopersicon esculentum* cDNA clone cLEG43D8 5' sequence, mRNA sequence"; source: *Lycopersicon esculentum* (*Solanum lycopersicum*).

NCBI acc. No. BF263411 (gi: 13260800) (Nov. 17, 2000); Wing,R., et al. "Development of a genetically and physically anchored EST resource for barley genomics: Blumeria infected incompatible (Mla13) seedling leaf cDNA library" (Unpublished (2001)).

NCBI acc. No. BF275458 (gi: 11206528) (Nov. 17, 2000); Wing,R.A., et al. Title: "An integrated analysis of the genetics, development, and evolution of the cotton fiber" (Unpublished (2000)).

NCBI acc. No. BF275652 (gi: 11206722) (Nov. 17, 2000); Wing,R.A., et al. Title: "An integrated analysis of the genetics, development, and evolution of the cotton fiber" (Unpublished (2000)).

NCBI acc. No. BF277659 (gi: 11208729) (Nov. 17, 2000); Wing,R.A., et al. Title: "An integrated analysis of the genetics, development, and evolution of the cotton fiber" (Unpublished (2000)).

NCBI acc. No. BF324075 (gi: 11273699) (Nov. 21, 2000); Shoemaker,R., et al. "su22c11.y1 Gm-c1068 *Glycine max* cDNA clone Genome Systems Clone Id: Gm-c1068-117 5' similar to TR:P93589 P93589 DNA binding Protein Homolog. ;, mRNA sequence"; source: *Glycine max* (soybean); Title: Public Soybean EST.

NCBI acc. no. BF425796 (gi: 11413785) (Nov. 28, 2000); Shoemaker,R., et al. Title: "Public Soybean EST Project" (Unpublished (1999)).

NCBI acc. No. BF518896 (gi: 11607651) (Dec. 8, 2000); Fedorova,M., et al. Title: "ESTs from leaves of *Medicago truncatula* after inoculation with *Colletotrichum trifolii*" (Unpublished (2000)).

NCBI acc. No. BF520727 (gi: 11609410) (Dec. 8, 2000); Fedorova,M., et al. Title: "ESTs from leaves of *Medicago truncatula* after inoculation with *Colletotrichum trifolii*" (Unpublished (2000)).

NCBI acc. No. BF588055 (gi: 11680379) (Dec. 12, 2000); Cordonnier-Pratt,M.-M., et al. Title: "An EST database from *Sorghum*: floral-induced meristems" (Unpublished (2000)).

NCBI acc. No. BF621655 (gi: 13083645) (Dec. 18, 2000); Wing,R., et al. Title: "Development of a genetically and physically anchored EST resource for barley genomics: Morex cold-stressed seedling shoot cDNA library" (Unpublished (2001)).

NCBI acc. No. BF634482 (gi: 11898640) (Dec. 19, 2000); Torrez-Jerez,I., et al. Title: "Expressed Sequence Tags from the Samuel Roberts Noble Foundation *Medicago truncatula* drought library" (Unpublished (2000)).

NCBI acc. No. BF637755 (gi: 11901913) (Dec. 19, 2000); Liu,J., et al. Title: "Expressed Sequence Tags from the Samuel Roberts Noble Foundation *Medicago truncatula* phosphate-starved leaf library" (Unpublished (2000)).

NCBI acc. No. BF644995 (gi: 11910124) (Dec. 20, 2000); Torres-Jerez,I., et al. Title: "Expressed Sequence Tags from the Samuel Roberts Noble Foundation—Center for Medicago Genomics Research" (Unpublished (2000)).

NCBI acc. No. BF646324 (gi: 11911454) (Dec. 20, 2000); Torres-Jerez, I., et al. Title: "Expressed Sequence Tags from the Samuel Roberts Noble Foundation—Center for Medicago Genomics Research" (Unpublished (2000)).

NCBI acc. No. BF647222 (gi: 11912352) (Dec. 20, 2000); Torres-Jerez,I., et al. Title: "Expressed Sequence Tags from the Samuel Roberts Noble Foundation—Center for Medicago Genomics Research" (Unpublished (2000)).

NCBI acc. No. BF647376 (gi: 11912506) (Dec. 20, 2000); Torres-Jerez,I., et al. Title: "Expressed Sequence Tags from the Samuel Roberts Noble Foundation—Center for Medicago Genomics Research" (Unpublished (2000)).

NCBI acc. No. BF647437 (gi: 11912567) (Dec. 20, 2000); Torres-Jerez,I., et al. Title: "Expressed Sequence Tags from the Samuel Roberts Noble Foundation—Center for Medicago Genomics Research" (Unpublished (2000)).

NCBI acc. No. BF648429 (gi: 11913559) (Dec. 20, 2000); Torres-Jerez,I., et al. Title: "Expressed Sequence Tags from the Samuel Roberts Noble Foundation—Center for Medicago Genomics Research" (Unpublished (2000)).

NCBI acc. No. BF649047 (gi: 11914093) (Dec. 20, 2000); Torres-Jerez,I., et al. Title: "Expressed Sequence Tags from the Samuel Roberts Noble Foundation—Center for Medicago Genomics Research" (Unpublished (2000)).

NCBI acc. No. BF649790 (gi: 11914920) (Dec. 20, 2000); Torres-Jerez,I., et al. Title: "Expressed Sequence Tags from the Samuel Roberts Noble Foundation—Center for Medicago Genomics Research" (Unpublished (2000)).

NCBI acc. No. BF649879 (gi: 11915009) (Dec. 20, 2000); Torres-Jerez,I., et al. Title: "Expressed Sequence Tags from the Samuel Roberts Noble Foundation—Center for Medicago Genomics Research" (Unpublished (2000)).

NCBI acc. No. BF650178 (gi: 11915308) (Dec. 20, 2000); Torres-Jerez,I., et al. Title: "Expressed Sequence Tags from the Samuel Roberts Noble Foundation—Center for Medicago Genomics Research" (Unpublished (2000)).

NCBI acc. No. BF650547 (gi: 11915677) (Dec. 20, 2000); Torres-Jerez, I ., et al. Title: "Expressed Sequence Tags from the Samuel Roberts Noble Foundation—Center for Medicago Genomics Research" (Unpublished (2000)).

NCBI acc. No. BF715904 (gi: 12015176) (Jan. 2, 2001); Shoemaker,R., et al. Title: "Public Soybean EST Project" (Unpublished (1999)).

NCBI acc. No. BG046680 (gi: 12495682) (Jan. 25, 2001); Shoemaker,R., et al. Title: "Public Soybean EST Project" (Unpublished (1999)).

NCBI acc. No. BG128566 (gi: 12628754) (Jan. 31, 2001); van der Hoeven,R., et al. Title: "Generation of ESTs from tomato shoot/meristem tissue" (Unpublished (2001)).

NCBI acc. No. BG129573 (gi: 12629761) (Jan. 31, 2001); van der Hoeven,R., et al. Title: "Generation of ESTs from tomato shoot/meristem tissue" (Unpublished (2001)).

NCBI acc. No. BG155935 (gi: 12689599) (Feb. 6, 2001); Shoemaker,R., et al. Title: "Public Soybean EST Project" (Unpublished (1999)).

NCBI acc. No. BG239157 (gi: 12774230) (Feb. 13, 2001); Shoemaker,R., et al. Title: "Public Soybean EST Project" (Unpublished (1999)).

NCBI acc. No. BG240408 (gi: 12775495) (Feb. 13, 2001); Cordonnier-Pratt,M.-M., et al. Title: "An Est database from *Sorghum*: ovaries of varying immature stages" (Unpublished (2000)).

NCBI acc. No. BG309153 (gi: 13110000) (Feb. 22, 2001); Wing,R., et al. Title: "Development of a genetically and physically anchored EST resource for barley genomics: *Morex* unstressed seedling shoot cDNA library" (Unpublished (2001)).

NCBI acc. No. BG309155 (gi: 13110002) (Feb. 22, 2001); Wing,R., et al. Title: "Development of a genetically and physically anchored EST resource for barley genomics: *Morex* unstressed seedling shoot cDNA library" (Unpublished (2001)).

NCBI acc. No. BG321358 (gi: 13151036) (Feb. 27, 2001); Singh,J. A., et al. Title: "Expressed Sequence Tags from Cold-Stressed *Descurainia sophia* Seedlings" (Unpublished (2001)).

NCBI acc. No. BG343807 (gi: 13156136) (Feb. 27, 2001); Wing,R., et al. Title: "Development of a genetically and physically anchored EST resource for barley genomics: *Morex* pre-anthesis spike cDNA library" (Unpublished(2001)).

NCBI acc. No. BG381764 (gi: 13306236) (Mar. 12, 2001); Anderson,J.V., et al. Title: "Identification of mRNAs expressed in underground adventitious buds of *Euphorbia esula* (leafy spurge)" (Unpublished (2000)).

NCBI acc. No. BG405293 (gi: 13311642) (Mar. 13, 2001); Shoemaker,R., et al. Title: "Public Soybean EST Project" (Unpublished (1999)).

NCBI acc. No. BG406120 (gi: 13312469) (Mar. 13, 2001); Shoemaker,R., et al. Title: "Public Soybean EST Project" (Unpublished (1999)).

NCBI acc. No. BG444654 (gi: 13354306) (Mar. 15, 2001); Wing,R. A., et al. Title: "An integrated analysis of the genetics, development, and evolution of the cotton fiber" (Unpublished (2000)).

NCBI acc. No. BG449954 (gi: 13368736) (Mar. 16, 2001); Torrez-Jerez,I., et al. Title: "Expressed Sequence Tags from the Samuel Roberts Noble Foundation *Medicago truncatula* drought library" (Unpublished (2000)).

NCBI acc. No. BG450588 (gi: 13369358) (Mar. 16, 2001); Torrez-Jerez,I., et al. Title: "Expressed Sequence Tags from the Samuel Roberts Noble Foundation *Medicago truncatula* drought library" (Unpublished (2000)).

NCBI acc. No. BG451892 (Gi: 13370674) (Mar. 16, 2001); Torrez-Jerez,I., et al. Title: "Expressed Sequence Tags from the Samuel Roberts Noble Foundation *Medicago truncatula* drought library" (Unpublished (2000)).

NCBI acc. No. BG455325 (gi: 13378650) (Mar. 19, 2001); Liu,J., et al. Title: "Expressed Sequence Tags from the Samuel Roberts Noble Foundation *Medicago truncatula* phosphate-starved leaf library" (Unpublished (2000)).

NCBI acc. No. BG459073 (gi: 13382398) Mar. 19, 2001); Anderson,J.V., et al. Title: "Identification from mRNAs expressed in underground adventitious buds of *Euphorbia esula* (leafy spurge)" (Unpublished (2000)).

NCBI acc. No. BG508757 (gi: 13479414) (Mar. 28, 2001); Shoemaker,R., et al. Title: "Public Soybean EST Project" (Unpublished (1999)).

NCBI acc. No. BG510218 (gi: 13480875) (Mar. 28, 2001); Shoemaker,R., et al. Title: "Public Soybean EST Project" (Unpublished (1999)).

NCBI acc. No. BG581520 (gi: 13596584) (Apr. 11, 2001); Fedorova,M., et al. Title: "ESTs from one month old nitrogen-fixing root nodules of *Medicago truncatula*, 2001" (Unpublished (2001)).

NCBI acc. No. BG582281 (gi: 13597345) (Apr. 11, 2001); Fedorova,M., et al. Title: "ESTs from one month old nitrogen-fixing root nodules of *Medicago truncatula*, 2001" (Unpublished (2001)).

NCBI acc. No. BG582854 (gi: 13597918) (Apr. 11, 2001); Fedorova,M., et al. Title: "ESTs from one month old nitgrogen-fixing root nodules of *Medicago truncatula*, 2001" (Unpublished (2001)).

NCBI acc. No. BG583042 (gi: 13598098) (Apr. 11, 2001); Fedorova,M., et al. Title: "ESTs from one month old nitrogen-fixing root nodules of *Medicago truncatula*, 2001" (Unpublished (2001)).

NCBI acc. No. BG583745 (gi: 13598809) (Apr. 11, 2001); Fedorova,M., et al. Title: "ESTs from one month old nitrogen-fixing root nodules of *Medicago truncatula*, 2001" (Unpublished (2001)).

NCBI acc. No. BG583761 (gi: 13598825) (Apr. 11, 2001); Fedorova,M., et al. Title: "ESTs from one month old nitrogen-fixing root nodules of *Medicago truncatula*, 2001" (Unpublished (2001)).

NCBI acc. No. BG591632 (gi: 13609772) (Apr. 12, 2001); Zhang,P., et al. Title: "Generation of ESTs from Potato Leaves Challenged with *Phytophthora infestans*, Incompatible Reaction" (Unpublished (2000)).

NCBI acc. No. BG592132 (gi: 13610272) (Apr. 12, 2001); Zhang,P., et al. Title: "Generation of ESTs from Potato Leaves Challenged with *Phytophthora infestans*, Incompatible Reaction" (Unpublished (2000)).

NCBI acc. No. BG596765 (gi: 13614905) (Apr. 12, 2001); van der Hoeven,R., et al. Title: "Generations of ESTs from sprouting potato eyes" (Unpublished (2000)).

NCBI acc. No. BG607048 (gi: 13657031) (Apr. 17, 2001); Anderson,O.D., et al. Title: "The structure and function of the expressed portion of the wheat genomes—Early reproductive apex cDNA library from *Triticum monococcum*" (Unpublished (2001)).

NCBI acc. No. BG643340 (gi: 13778565) (Apr. 24, 2001); van der Hoeven,R., et al. Title: "Generation of ESTs from tomato shoot/meristem tissue" (Unpublished (2001)).

NCBI acc. No. BG646774 (gi: 13781886) (Apr. 24, 2001); Hahn,M. G., et al. Title: "ESTs from roots of *Medicago truncatula* treated with oligogalacturonides of DP 6-20" (Unpublished (2001)).
NCBI acc. No. BG647771 (gi: 13782883) (Apr. 24, 2001); Hahn,M. G., et al. Title: "ESTs from roots of *Medicago truncatula* treated with oligogalacturonides of DP 6-20" (Unpublished (2001)).
NCBI acc. No. BG647799 (gi: 13782911) (Apr. 24, 2001); Hahn,M. G., et al. Title: "ESTs from roots of *Medicago truncatula* treated with oligogalacturonides of DP 6-20" (Unpublished (2001)).
NCBI acc. No. BG647917 (gi: 13783029) (Apr. 24, 2001); Hahn,M. G., et al. Title: "ESTs from roots of *Medicago truncatula* treated with oligogalacturonides of DP 6-20" (Unpublished (2001)).
NCBI acc. No. BG650102 (gi: 13787510) (Apr. 25, 2001); Shoemaker,R., et al. Title: "Public Soybean EST Project" (Unpublished (1999)).
NCBI acc. No. BG726262 (gi: 14011340) (May 9, 2001); Shoemaker,R., et al. Title: "Public Soybean EST Project" (Unpublished (1999)).
NCBI acc. No. BG790094 (gi: 14125656) (May 16, 2001); Shoemaker,R., et al. Title: "Public Soybean EST Project" (Unpublished (1999)).
NCBI acc. No. BG840869 (gi: 14207191) (May 25, 2001); Qiu,F., et al. Title: "Expressed Sequence Tags from B73 Maize Seedlings and Silks" (Unpublished (2001)).
NCBI acc. No. BG841174 (gi: 14207496) (May 25, 2001); Qiu,F., et al. Title: "Expressed Sequence Tags from B73 Maize Seedlings and Silks" (Unpublished (2001)).
NCBI acc. No. BG886550 (gi: 14263636) (May 30, 2001); van der Hoeven,R., et al. Title: "Generations of ESTs from dormant potato tubers" (Unpublished (2001)).
NCBI acc. No. BH454277 (gi: 17639988) (Dec. 12, 2001); Ayele,M., et al. Title: "Whole genome shotgun sequencing of *Brassica oleracea* and its application to gene discovery and annotation in *Arabidopsis*" (Genome Res. 15 (4), 487-495 (2005)).
NCBI acc. No. BH594074 (gi: 17846526) (Dec. 15, 2001); Ayele,M., et al. Title: "Whole genome shotgun sequencing of *Brassica oleracea* and its application to gene discovery and annotation in *Arabidopsis*" (Genome Res. 15 (4), 487-495 (2005)).
NCBI acc. No. BI265685 (gi: 14869141) (Jul. 18, 2001); Korth,K., et al. Title: "Expressed Sequence Tags from the Samuel Roberts Noble Foundation *Medicago truncatula* insect herbivory library" (Unpublished (2000)).
NCBI acc. No. BI271853 (gi: 14880681) (Jul. 18, 2001); Torres-Jerez,I., et al. Title: "Expressed Sequence Tags from the Samuel Roberts Noble Foundation *Medicago truncatula* flower library" (Unpublished (2001)).
NCBI acc. No. BI308635 (gi: 14982962) (Jul. 20, 2001); Grusak,M. A., et al. Title: "ESTs from developing reproductive tissues of *Medicago truncatula*" (Unpublished (2001)).
NCBI acc. No. BI308895 (gi: 14983222) (Jul. 20, 2001); Grusak,M. A., et al. Title: "ESTs from developing reproductive tissues of *Medicago truncatula*" (Unpublished (2001)).
NCBI acc. No. BI309617 (gi: 14983944) (Jul. 20, 2001); Grusak,M. A., et al. Title: "ESTs from developing reproductive tissues of *Medicago truncatula*" (Unpublished (2001)).
NCBI acc. No. BI310543 (gi: 14984870) (Jul. 20, 2001); Grusak,M. A., et al. Title: "ESTs from developing reproductive tissues of *Medicago truncatula*" (Unpublished (2001)).
NCBI acc. No. BI321594 (gi: 15000780) (Jul. 23, 2001); Shoemaker,R., et al. Title: "Public Soybean EST Project" (Unpublished (1999)).
NCBI acc. No. BI322080 (gi: 15001266) (Jul. 23, 2001); Shoemaker,R., et al. Title: "Public Soybean EST Project" (Unpublished (1999)).
NCBI acc. No. BI406379 (gi: 15185777) (Aug. 14, 2001); Crookshanks,M., et al. Title: "The potato tuber transcriptome: analysis of 6077 expressed sequence tags" (FEBS Lett. 506 (2), 123-126 (2001)).
NCBI acc. No. BI418371 (gi: 15189394) (Aug. 15, 2001); Colebatch,G., et al. Title: "*Lotus japonicus* root nodule ESTs: tools for functional genomics" (Unpublished (2000)).
NCBI acc. No. BI418604 (gi: 15189627) (Aug. 15, 2001); Colebatch,G., et al. Title: "*Lotus japonicus* root nodule ESTs: tools for functional genomics" (Unpublished (2000)).
NCBI acc. No. BI420305 (gi: 15191328) (Aug. 15, 2001); Colebatch,G., et al. Title: "*Lotus japonicus* root nodule ESTs: tools for functional genomics" (Unpublished (2000)).
NCBI acc. No. BI421270 (gi: 15194638) (Aug. 16, 2001); Alcala,J., et al. Title: "Generation of ESTs from tomato callus tissue" (Unpublished (1999)).
NCBI acc. No. BI421507 (gi: 15195085) (Aug. 16, 2001); Alcala,J., et al. Title: "Generation of ESTs from tomato callus tissue" (Unpublished (1999)).
NCBI acc. No. BI421558 (gi: 15195182) (Aug. 16, 2001); Alcala,J., et al. Title: "Generation of ESTs from tomato callus tissue" (Unpublished (1999)).
NCBI acc. No. BI421722 (gi: 15195509) (Aug. 16, 2001); Alcala,J., et al. Title: "Generation of ESTs from tomato callus tissue" (Unpublished (1999)).
NCBI acc. No. BI421895 (gi: 15195839) (Aug. 16, 2001); Alcala,J., et al. Title: "Generation of ESTs from tomato callus tissue" (Unpublished (1999)).
NCBI acc. No. BI426037 (gi: 15203269) (Aug. 16, 2001); Shoemaker,R., et al. Title: "Public Soybean EST Project" (Unpublished (1999)).
NCBI acc. No. BI427468 (gi: 15204700) (Aug. 16, 2001); Shoemaker,R., et al. Title: "Public Soybean EST Project" (Unpublished (1999)).
NCBI acc. No. BI436183 (gi: 15260873) (Aug. 21, 2001); van der Hoeven,R., et al. Title: "Generation of ESTs from in vitro grown microtubers" (Unpublished (2001)).
NCBI acc. No. BI468669 (gi: 15284778) (Aug. 24, 2001); Shoemaker,R., et al. Title: "Public Soybean EST Project" (Unpublished (1999)).
NCBI acc. No. BI469284 (gi: 15285393) (Aug. 24, 2001); Shoemaker,R., et al. Title: "Public Soybean EST Project" (Unpublished (1999)).
NCBI acc. No. BI470707 (gi: 15286816) (Aug. 24, 2001); Shoemaker,R., et al. Title: "Public Soybean EST Project" (Unpublished (1999)).
NCBI acc. No. BQ165291 (gi: 20307557) (Apr. 25, 2002); VandenBosch,K., et al. Title: "The *Medicago truncatula* 'kiloclone' set; ESTs selected and re-arrayed from various libraries" (Unpublished (2002)).
NCBI acc. No. CAB93939 (gi: 8346773) (Jun. 7, 2000); Menke,F.L. H., et al. Title: "A jasmonate- and elicitor-responsive element in the periwinkle secondary metabolite biosynthetic gene Str interacts with a jasmonate- and elicitor-inducible AP2-domain transcription factor, ORCA2" (Unpublished).
NCBI acc. No. CAB93940 (gi: 8346775) (Jun. 7, 2000); Menke,F.L. H., et al. Title: "A jasmonate- and elicitor-responsive element in the periwinkle secondary metabolite biosynthetic gene Str interacts with a jasmonate- and elicitor-inducible AP2-domain transcription factor, ORCA2" (Unpublished).
NCBI acc. No. CAB96899 (gi: 8980313) (Jul. 8, 2000); van der Fits,L., et al. Title: "ORCA3, a jasmonate-responsive master regulator of multiple genes in plant primary and secondary metabolism" (Unpublished).
NCBI acc. No. CAB96900 (gi: 8980315) (Jul. 8, 2000); van der Fits,L., et al. "AP2-domain DNA-binding protein [*Catharanthus roseus*]"; source: *Catharanthus roseus* (Madagascar periwinkle); Title: ORCA3, a jasmonate-responsive master regulator of multiple genes in plant primary and secondary.
NCBI acc. No. CAC12822 (gi: 10798644) (Oct. 11, 2000); Shen,W. H., et al. Title: "*Nicotiana tabacum* cDNA (partial) encoding AP2 domain-containing protein" (Unpublished).
NCBI acc. No. CAC21763 (gi: 12225884) (Jan. 14, 2001); Helentjaris,T.G., et al. Title: "Signal transduction genes and methods of use" (Patent: WO 0070059-A Nov. 23, 2000; Pioneer HI-Bred International, Inc. (US)).
NCBI acc. No. CAC21771 (gi: 12225916) (Jan. 14, 2001); Helentjaris,T.G., et al. Title: "Signal transduction genes and methods of use" (Patent: WO 0070059-A Nov. 23, 2000; Pioneer HI-Bred International, Inc. (US)).

NCBI acc. No. CAC39058 (gi: 14140141) (May 17, 2001); Mayer,K., et al. Title: "Conservation of microstructure bewtween a sequenced region of the genome of rice and multiple segments of the genome of *Arabidopsis thaliana*" (Unpublished).

NCBI acc. No. CAC39060 (gi: 14140143) (May 17, 2001); Mayer,K., et al. Title: "Conservation of microstructure bewtween a sequenced region of the genome of rice and multiple segments of the genome of *Arabidopsis thaliana*" (Unpublished).

NCBI acc. No. CG333070 (gi: 34250336) (Aug. 26, 2003); Whitelaw,C.A., et al. Title: "Consortium for Maize Genomics" (Unpublished (2002)).

NCBI acc. No. CK260302 (gi: 39817280) (Dec. 12, 2003); Rensink,W., et al. Title: "Analyzing the potato abiotic stress transcriptome using expressed sequence tags" (Genome 48 (4), 598-605 (2005)).

NCBI acc. No. CK277725 (gi: 39834703) (Dec. 12, 2003); Rensink,W., et al. Title: "Analyzing the potato abiotic stress transcriptome using expressed sequence tags" (Genome 48 (4), 598-605 (2005)).

NCBI acc. No. D38123 (gi: 790359) (May 1, 1995); Ohme-Takagi,M., et al. "Tobacco mRNA"; source: Unknown.; Title: "Etylene-inducible DNA binding proteins that interact with an ethylene responsive element" (The Plant Cell 7, 173-182 (1995)).

NCBI acc. No. D38125 (gi: 790361) (May 1, 1995); Ohme-Takagi,M., et al. "Tobacco mRNA"; source: Unknown.; Title: "Etylene-inducible DNA binding proteins that interact with an ethylene responsive element" (The Plant Cell 7, 173-182 (1995)).

NCBI acc. No. D38126 (gi: 790362) (May 1, 1995); Ohme-Takagi,M., et al. "Tobacco mRNA"; source: Unknown.; Title: "Etylene-inducible DNA binding proteins that interact with an ethylene responsive element" (The Plant Cell 7, 173-182 (1995)).

NCBI acc. No. N97133 (gi: 1269500) (Aug. 16, 1995); Newman,T., et al. Title: "Genes galore: a summary of methods for accessing results from large-scale partial sequencing of anonymous *Arabidopsis* cDNA clones" (Plant Physiol. 106, 1241-1255 (1994)).

NCBI acc. No. O04681 (gi: 7531180) (Apr. 10, 2000); Zhou,J., et al. Title: "The Pto kinase conferring resistance to tomato bacterial speck disease interacts with proteins that bind a cis-element of pathogenesis-related genes" (EMBO J. 16 (11), 3207-3218 (1997)).

NCBI acc. No. O04682 (gi: 7531181) (Apr. 10, 2000); Zhou,J., et al. Title: "The Pto kinase conferring resistance tomato bacterial speck disease interacts with proteins that bind a cis-element of pathogenesis-related genes" (EMBO J. 16 (11), 3207-3218 (1997)).

NCBI acc. No. T01986 (gi: 7489208) (Apr. 6, 2000); Park,J.M., et al. "Tsi1 protein—common tobacco"; source: *Nicotiana tabacum* (common tobacco); Title: "Direct Submission" (Submitted (??-Apr. 1998) to the EMBL Data Library).

NCBI acc. No. T02432 (gi: 7489123) (Apr. 6, 2000); Ohme-Takagi,M., et al. Title: "Ethylene-inducible DNA binding proteins that interact with an ethylene-responsive element" (Plant Cell 7 (2), 173-182 (1995)).

NCBI acc. No. T02433 (gi: 7489114) (Apr. 6, 2000); Ohme-Takagi,M., et al. Title: "Ethylene-inducible DNA binding proteins that interact with an ethylene-responsive element" (Plant Cell 7 (2), 173-182 (1995)).

NCBI acc. No. T02434 (gi: 7489115) (Apr. 6, 2000); Ohme-Takagi,M., et al. Title: "Ethylene-inducible DNA binding proteins that interact with an ethylene-responsive element" (Plant Cell 7 (2), 173-182 (1995)).

NCBI acc. No. T02590 (gi: 7489113) (Apr. 6, 2000); Ohme-Takagi,M., et al. Title: "Ethylene-inducible DNA binding proteins that interact with an ethylene-responsive element" (Plant Cell 7 (2), 173-182 (1995)).

NCBI acc. No. T03927 (gi: 7489116) (Apr. 6, 2000); Xu,P., et al. "DNA binding protein S25-XP1—common tobacco"; source: *Nicotiana tabacum* (common tobacco); Title: "Direct Submission" (Submitted (??-Dec. 1996) to the EMBL Data Library).

NCBI acc. No. T07686 (gi: 7489077) (Apr. 6, 2000); Zhou, J., et al. "transcription factor Pti4—tomato (fragment)"; source: *Lycopersicon esculentum* (tomato); Title: "Direct Submission" (Submitted (??-Jul. 1998) to the EMBL Data Library).

NCBI acc. No. T07689 (gi: 7489078) (Apr. 6, 2000); Zhou,J., et al. Title: "The Pto kinase conferring resistance to tomato bacterial speck disease interacts with proteins that bind a cis-element of pathogenesis-related genes" (EMBO J. 16 (11), 3207-3218 (1997)).

NCBI acc. No. T07728 (gi: 7489079) (Apr. 6, 2000); Zhou,J., et al. Title: "The Pto kinase conferring resistance to tomato bacterial speck disease interacts with proteins that bind a cis-element of pathogenesis-related genes" (EMBO J. 16 (11), 3207-3218 (1997)).

NCBI acc. No. T07784 (gi: 7489226) (Apr. 6, 2000); Leggewie,G., et al. "A cDNA from potato with homology to DnaJ is identical to a hitherto unidentified gene that is induced upon tuberization in potato and upon flowering in tobacco" (Plant Physiol. 117, 1127 (1998)).

NCBI acc. No. U81157 (gi: 1732405) (Dec. 16, 1996); Xu,P., et al. "Direct Submission" (Submitted (Dec. 6, 1996) Biotechnology Institute, Zhejiang Agriculture Unversity, Hangzhou, Zhejiang 310029, P.R.China).

NCBI acc. No. U89255 (gi: 2213780) (Jun. 25, 1997); Zhou,J., et al. "The Pto Kinase Conferring Resistance to Tomato Bacterial Speck Disease Interacts with Proteins that Bind a Cis-Element of Pathogenesis-Related Genes" (EMBO J. 16, 3207-3218 (1997)).

NCBI acc. No. U89256 (gi: 2213782) (Jun. 25, 1997); Zhou,J., et al. "The Pto Kinase Conferring Resistance to Tomato Bacterial Speck Disease Interacts with Proteins that Bind a Cis-Element of Pathogenesis-Related Genes" (EMBO J. 16, 3207-3218 (1997)).

NCBI acc. No. U91857 (gi: 4099913) (Jan. 5, 1999); Gardner,R.C., et al. "*Stylosanthes hamata* ethylene-responsive element binding protein homolog gene, complete cds"; source: *Stylosanthes hamata*; Title: "Aluminium Tolerance in Yeast Conferred by Over-expression of *Stylosanthes* genes" (Unpublished).

NCBI acc. No. U91982 (gi: 4099920) (Jan. 5, 1999); Gardner,R.C., et al. "*Stylosanthes hamata* EREBP-3 homolog mRNA, complete cds"; source: *Stylosanthes hamata*; Title: "Aluminium Tolerance in Yeast Conferred by Over-expression of *Stylosanthes* Genes" (Unpublished).

NCBI accession No. X59714 (gi:22379) (Apr. 21, 1993); Benoist, C, "*Z.mays* mRNA for CAAT-box DNA binding protein subunit B (NF-YB)"; (*Zea mays*) (note: the original submission and latest update are provided for examination) (publication: see Nucleic Acids Res. 20 (5), 1087-1091, 1992, Evolutionary variation of the CCAAT-binding transcription factor NF-Y.

NCBI accession No. Y13724 (gi:2398528) (Sep. 16, 1997); Edwards, D., "*Arabidopsis thaliana* mRNA for Hap3b transcription factor" (note: the original submission and latest update are provided for examination).

NCBI acc. No. AA598183 (gi: 2413606) (Sep. 20, 1997); Newman,T., et al. Title: "Genes galore: a summary of methods for accessing results from large-scale partial sequencing of anonymous *Arabidopsis* cDNA clones" (Plant Physiol. 106, 1241-1255 (1994)).

NCBI acc. No. T00409 (gi: 276890) (Nov. 10, 1992); McCombie,W. R., et al. Title: "*Caenorhabditis elegans* cDNAs" (Unpublished (1993)).

NCBI accession No. AF193440 (gi:6289056) (Nov. 9, 1999); Gherraby, W., et al., "*Arabidopsis thaliana* heme activated protein (HAP5c) mRNA, complete cds".

TREMBL Acc. No. AB008103 (Aug. 21, 1998); "*Arabidopsis thaliana* AtERF-1 mRNA for ethylene responsive element binding factor 1, complete cds."

NCBI acc. No. AB008104 (gi: 3434968) (Aug. 19, 1998); Usui.A., et al. Title: "ERF family" (Unpublished (1998)).

TREMBL Acc. No. AB009055 (Sep. 3, 1999); , et al. "*Arabidopsis thaliana* genomic cDNA chromosome 5, P1 clone: MXC20".

Database GenEMBL AC002338 Online, Jul. 24, 1997; Lin et al. Title: "Sequence and analysis of chromosome 2 of the plant *Arabidopsis thaliana*, Nature" (Dec. 16, 1999) vol. 402, pp. 761-768.

TREMBL Acc. No. AC002388 (Aug. 4, 1997); Rounsley S. D. et al., "*Arabidopsis thaliana* chromosome II BAC T13E15 genomic sequence, complete sequence."

TREMBL Acc. No. AF003096 (Jul. 28, 1997); "*Arabidopsis thaliana* AP2 domain containing protein RAP2.3 mRNA, complete cds."

TREMBL Acc. No. AF007269 (Jun. 24, 1997); "*Arabidopsis thaliana* BAC IG002N01."

NCBI acc. No. AI999616 (gi: 5846521) (Sep. 8, 1999); Chen,J., et al. Title: "*Arabidopsis thaliana* Gene Expression MicroArray" (Unpublished (1999)).

TREMBL Acc. No. AL161546 (Mar. 16, 2000); "*Arabidopsis thaliana* DNA chromosome 4, contig fragment No. 46".
TREMBL Acc. No. O80337 (May 30, 2000); "Ethylene-responsive transcription factor 1A (Ethylene-responsive element binding factor 1A) (EREBP-1A) (AtERF1)."
TREMBL Acc. No. P42736 (Nov. 1, 1995); "AP2 domain transcription factor RAP2.3 (Related to AP2 protein 3) (Cadmium-induced protein AS30)."
TREMBL Acc. No. U89255 (Jun. 28, 1997); "*Lycopersicon esculentum* DNA-binding protein Pti4 mRNA, complete cds." (Duplicate entry above for U89255).
TREMBL Acc. No. Z97343 (Jul. 4, 1997); "*Arabidopsis thaliana* DNA chromosome 4, ESSA I FCA contig fragment No. 8".
TREMBL Acc. No. O22167 (Q8L9K1) (Jan. 1, 1998); Rounsley, et al.
NCBI acc. No. NP_182011 (gi: 15225361) (Aug. 21, 2001); Lin,X., et al. Title: "Sequence and analysis of chromosome 2 of the plant *Arabidopsis thaliana*" (Nature 402 (6763), 761-768 (1999)).
NCBI acc. No. NP_567530 (gi: 18414897) (Jan. 29, 2002); , et al. "ethylene responsive element binding factor 1 (frameshift !)"; source: Unknown.; Title:"".
NCBI acc. No. ABD19651 (gi: 87116574) (Feb. 10, 2006); Shinn,P., et al. "At5g47220 [*Arabidopsis thaliana*]"; source: *Arabidopsis thaliana* (thale cress); Title: "*Arabidopsis* ORF clones" (Unpublished).
NCBI acc. No. Y10555 (gi: 2695702) (Dec. 18, 1997); Putterill,J.J., et al. "*A.thaliana* mRNA for CONSTANS protein"; source: *Arabidopsis thaliana* (thale cress); Title: "The flowering-time gene CONSTANS and homologue CONSTANS Like 1 exist as a tandem repeat on chromosome 5 of *Arabidopsis*" (Unpublished).
Ainley et al., Regulatable endogenous production of cytokinins up to 'toxic' levels in transgenic plants and plant tissues, The Plant Mol. Biol. (Apr. 1993) 22:13-23.
Allen, M.D., et al. (1998). A novel mode of DNA recognition by a beta-sheet revealed by the solution structure of the GCC-box binding domain in complex with DNA. Embo J 17, 5484-5496.
An et al., Organ-Specific and Developmental Regulation of the Nopaline Synthase Promoter in Transgenic Tobacco Plants. (May 1988) Plant Physiology 88:547-552.
Anand, Ajith et al: "Greenhouse and field testing of transgenic wheat plants stably expressing genes for thaumatin-like protein, chitinase and glucanase against *Fusarium graminearum*" J of Exper Botany, vol. 54, No. 384, Mar. 2003, pp. 1101-1111.
Aoyama et al. (Nov. 1995) Ectopic expression of the *Arabidopsis* transcriptional activator Athb-1 alters leaf cell fate in tobacco. Plant Cell 7:1773-1785.
Asamizu, et al. (2000) Generation of 7137 non-redundant expressed sequence tags from a legume, *Lotus japonicus*. DNA Res. 7 (2), 127-130.
Asamizu, et al. (2000) A large scale analysis of cDNA in *Arabidopsis thaliana*: Generation of 12,028 non-redundant expressed sequence tags from normalized and size-selected cDNA libraries. DNA Res. 7 (3), 175-180.
NCBI acc. No. Y10556 (gi: 2695704) (Dec. 18, 1997); Putterill.J.J., et al. "*A.thaliana* constans gene"; source: *Arabidopsis thaliana* (thale cress); Title: "The flowering-time gene CONSTANS and homologue CONSTANS Like 1 exist as a tandem repeat on chromosome 5 of *Arabidopsis*" (Unpublished).
Ashida, Y. et al. (2002). Molecular cloning and mRNA expression of geraniol-inducible genes in cultured shoot primordia of *Matricaria chamomilla*. Biosci. Biotechnol. Biochem. 66 (11), 2511-2514.
Ayele, et al. (2005). Whole genome shotgun sequencing of *Brassica oleracea* and its application to genediscovery and annotation in *Arabidopsis*. Genome Res. 15 (4), 487-495.
Baerson et al. (Dec. 1994). Identification of domains in an *Arabidopsis* acyl carrier protein gene promoter required for maximal organ-specific expression. Plant Mol. Biol. 26:1947-1959.
Baerson et al. (May 1993). Developmental regulation of an acyl carrier protein gene promoter in vegetative and reproductive tissues. Plant Mol. Biol. 22:255-267.
Baumann et al. (Mar. 1999). The DNA Binding Site of the Dof Protein NtBBF1 Is Essential for Tissue-Specific . . . , The Plant Cell 11:323-334.

Berrocal-Lobo, M., et al. (2002). Constitutive expression of Ethylene-Response-Factor1 in *Arabidopsis* confers resistance to several necrotrophic fungi. Plant J 29, 23-32.
Berrocal-Lobo, M., and Molina, A. (2004). Ethylene response factor 1 mediates *Arabidopsis* resistance to the soilborne fungus *Fusarium oxysporum*. Mol Plant Microbe Interact 17, 763-770.
Bevan, et al. (Jan. 1998) Analysis of 1.9 Mb of contiguous sequence from chromosome 4 of *Arabidopsis thaliana*. Nature 391 (6666):438-9.
Bird et al. (1988). The tomato polygalacturonase gene and ripening-specific expression in transgenic plants. Plant Mol. Biol. 11:651-662.
Bohmert et al., AG01 defines a novel locus of *Arabidopsis* controlling leaf development, EMBO J. (Jan. 2, 1998) 17:170-180.
Bork, P., Powers and Pitfalls in Sequence Analysis: The 70% Hurdle. Genome Research, vol. 10, 2000; pp. 398-400.
Bowman et al., Crabs Claw, a gene that regulates carpel and nectary developments in *Arabidopsis*, encodes a novel protein . . . , Development (Jun. 1999) 126:2387-2396.
Brown, R.L., et al. (2003). A role for the GCC-box in jasmonate-mediated activation of the PDF1.2 gene of *Arabidopsis*. Plant Physiol 132, 1020-1032.
Buerglin in Duboule (ed.) (1994) Guidebook to the Homeobox Genes, Oxford University Press, Oxford, UK pp. 27-71.
Bustin and Reeves (1996) High-mobility-group chromosomal proteins: architectural components that facilitate chromatin function. Prog. Nucl. Acids Res. Mol. Biol. 54:35-100.
Buttner et al (May 1997) "*Arabidopsis thaliana* ethylene-responsive element binding protein (AtEBP), an ethylene-inducible, GCC box DNA-binding protein interacts with an ocs element binding protein." Proc. Natl. Acad. Sci. USA 94: 5961-5966.
Campbell, et al. (1998). Isolation of a cDNA from potato with structural similarity to the AP2 gene superfamily (Accession No. U77655) (PGR98-129). Plant Physiol. 117 (3), 1127.
Cao et al. (May 1998). Generation of broad-spectrum disease resistance by overexpression of an essential regulatory gene in systemic acquired resistance. Proc. Natl. Acad. Sci. USA 95:6531-6536.
Century et al. (1997). NDR1, a Pathogen-Induced Component Required for *Arabidopsis* Disease Resistance.Science 278:1963-1965.
NCBI acc. No. CAA71587 (gi: 2695703) (Dec. 18, 1997); Putterill. J.J., et al. "CONSTANS [*Arabidopsis thaliana*]"; source: *Arabidopsis thaliana* (thale cress); Title: "The flowering-time gene CONSTANS and homologue CONSTANS Like 1 exist as a tandem repeat on chromosome 5 of *Arabidopsis*" (Unpublished).
Chakravarthy, S., et al. (2003). The tomato transcription factor Pti4 regulates defense-related gene expression via GCC box and non-GCC box cis elements. Plant Cell 15, 3033-3050.
Chao et al. (Jun. 27, 1997). Activation of the Ethylene Gas Response Pathway in *Arabidopsis* by the Nuclear Protein . . . , Cell 89:1133-1144.
Chen, C, and Chen, Z. (2002). Potentiation of developmentally regulated plant defense response by AtWRKY18, a pathogen-induced *Arabidopsis* transcription factor. Plant Physiol 129, 706-716.
Chen, W., et al. (2002). Expression profile matrix of *Arabidopsis* transcription factor genes suggests their putative functions in response to environmental stresses. Plant Cell 14, 559-574.
Chen, J. et al. (2003) An AP2/EREBP-type transcription factor gene from rice is cold-inducible and encodes a nuclear-localized protein. Theoretical and Applied Genetics 2003, vol. 107, pp. 972-979.
Cheong, Y.H., et al. (2002). Transcriptional profiling reveals novel interactions between wounding, pathogen, abiotic stress, and hormonal responses in *Arabidopsis*. Plant Physiol 129, 661-677.
Cheong, Y.H., et al. (2003). BWMK1, a rice mitogen-activated protein kinase, locates in the nucleus and mediates pathogenesis-related gene expression by activation of a transcription factor. Plant Physiol 132, 1961-1972.
Crookshanks, et al. (2001). The potato tuber transcriptome: analysis of 6077 expressed sequence tags. FEBS Lett. 506 (2), 123-126.
Da Costa E Silva et al. (Jul. 1993) BPF-1, a pathogen-induced DNA-binding protein involved in the plant defense response. Plant J. 4:125-135.
Daly et al. (Dec. 2001). Plant Systematics in the Age of Genomics. Plant Physiology 127:1328-1333.

Dehesh et al (Dec. 1990). A trans-acting factor that binds to a GT-motif in a phytochrome gene promoter. Science 250:1397-1399.

Di Laurenzio et al. (Aug. 9, 1996). The Scarecrow Gene Regulates an Asymmetric Cell Division That is Essential . . . , Cell 86:423-433.

Durrant, et al. (2000) cDNA-AFLP reveals a striking overlap in race-specific resistance and wound response gene expression profiles. Plant Cell 12 (6), 963-977.

Edwards, D., Murray, J.A., and Smith, A.G. (Jul. 1998). Multiple genes encoding the conserved CCAAT-box transcription factor complex are expressed in *Arabidopsis*. Plant Physiol 117, 1015-1022.

Elomaa, P., et al. (1996) Transformation of antisense constructs of the chalcone synthase gene superfamily into *Gerbera hybrida*: differential effect on the expression of family members. Molecular Breeding vol. 2, pp. 41 -50.

Estruch et al. (1994) Nucl. Acids Res. 22:3983-3989.

Eulgem, Thomas et al. (Sep. 1999). Early nuclear events in plant defense signalling: Rapid gene activation by WRKY transcription factors EMBO Journal, vol. 18, No. 17, pp. 4689-4699.

Feng, et al., (2002). Sequence and analysis of rice chromosome 4. Nature 420 (6913), 316-320.

Finkelstein, R.R., et al. (1998). The *Arabidopsis* abscisic acid response locus ABI4 encodes an APETALA 2 domain protein. Plant Cell 10, 1043-1054.

Fischer, U., and Droge-Laser, W. (2004). Overexpression of NtERF5, a new member of the tobacco ethylene response transcription factor family enhances resistance to tobacco mosaic virus. Mol Plant Microbe Interact 17, 1162-1171.

Forsburg, S.L. and Guarente, L.(Aug. 1989). Identification and characterization of HAP4: a third component of the CCAAT-bound HAP2/HAP3 heteromer. Genes Dev. 3:1166-1178.

Foster et al., Plant bZIP proteins gather at ACGT elements, FASEB J. (Feb. 1994) 8:192-200.

Fromm et al., An Octopine Synthase Enhancer Element Directs Tissue-Specific Expression and Binds ASF-1, a Factor from Tobacco Nuclear Extracts. (Oct. 1989) The Plant Cell 1:977-984.

Fujimoto, S.Y., et al. (2000). *Arabidopsis* ethylene-responsive element binding factors act as transcriptional activators or repressors of GCC box-mediated gene expression. Plant Cell 12, 393-404.

Gatz C, Chemical Control of Gene Expression, Annu. Rev. Plant Physiol. Plant Mol. Biol. (Jun. 1997) 48:89-108.

Gill and Ptashne (1987). Mutants of GAL4 protein altered in an activation function. Cell 51:121-126.

Giovannoni, et al. (1999) Genetic mapping of ripening and ethylene related loci in tomato. Theor. Appl. Genet. 98 (6/7), 1005-1013.

Giraudat et al. (Oct. 1992). Isolation of the *Arabidopsis* ABI3 gene by positional cloning. Plant Cell 4:1251-1261.

Gong, et al. (Jun. 2004). Genome-wide ORFeome cloning and analysis of *Arabidopsis* transcription factor genes. Plant Physiol. 135(2):773-782.

Gu, Y.Q., et al. (2000). Pti4 is induced by ethylene and salicylic acid, and its product is phosphorylated by the Pto kinase. Plant Cell 12, 771-786.

Gu, Y.Q., et al. (2002). Tomato transcription factors pti4, pti5, and pti6 activate defense responses when expressed in *Arabidopsis*. Plant Cell 14, 817-831.

Guervara-Garcia (1998). A 42 bp fragment of the pmas10 promoter containing an ocs-like element confers a developmental, wound- and chemically inducible expression pattern. Plant Mol. Biol. 38:743-753.

Guo, H., and Ecker, J.R. (2004). The ethylene signaling pathway: new insights. Curr Opin Plant Biol 7, 40-49.

Guo, Z.J., et al. (2004a). Overexpression of the AP2/EREBP transcription factor OPBP1 enhances disease resistance and salt tolerance in tobacco. Plant Mol Biol 55, 607-618.

Guo, et al. (2004) Protein tolerance to random amino acid change. Proc. Natl. Acad. Sci. USA 101: 9205-9210.

Gutterson, et al. (2004) Regulation of disease resistance pathways by AP2/ERF transcription factors. Current Opin. in Plant Biology, vol. 7, pp. 465-471.

Hall et al., Golden 2: A Novel Transcriptional Regulator of Cellular Differentiation in the Maize Leaf. The PlantCell (Jun. 1998) 10:925-936.

Hao, D., et al. (2002). Determinants in the sequence specific binding of two plant transcription factors, CBF1 and NtERF2, to the DRE and GCC motifs. Biochemistry 41, 4202-4208.

Hao, D., et al. (1998). Unique mode of GCC box recognition by the DNA-binding domain of ethylene-responsive element-binding factor (ERF domain) in plant. J Biol Chem 273, 26857-26861.

He, P., et al. (2001). Overexpression of Pti5 in tomato potentiates pathogen-induced defense gene expression and enhances disease resistance to *Pseudomonas syringae* pv. tomato. Mol Plant Microbe Interact 14, 1453-1457.

Heard et al. (Jul. 1997) Evolutionary diversity of symbiotically induced nodule MADS box genes:characterizatoin of nmhC5, a member of a novel subfamily. Molecular Plant-Microbe Interactions. Jul. 1997, vol. 10, No. 5, pp. 665-676.

Heard et al. (Jun. 1995) Symbiotic induction of a MADS-box gene during development of alfalfa root nodules. Proc. Natl. Acad. Sci. USA, vol. 92, pp. 5273-5277.

Hill, et al. (1998). Functional Analysis of Conserved Histidines in ADP-Glucose . . . Biochem. Biophys. Res. Comm. 244: 573-577.

Hollung, Kristin et al. (Jun. 1997) Developmental stress and ABA modulation of mRNA levels for bZIP transcription factors and Vp1 in barley embryos and embryo-derived suspension cultures, Plant Molecular Biology, vol. 35, No. 5, pp. 561-571.

Horvath, et al. (1998). Four classes of salicylate-induced tobacco genes. Mol. Plant Microbe Interact. 11 (9), 895-905.

Ishiguro, S. and Nakamura, K. (Sep. 28, 1994). Characterization of a cDNA encoding a novel DNA-binding protein, SPF1, that recognizes SP8 sequences in the 5' upstream regions of genes coding for sporamin and beta-amylase from sweet potato. Mol. Gen. Genet. 244: 563-571.

Jaglo-Ottosen, K.R., et al. (1998). *Arabidopsis* CBF1 overexpression induces COR genes and enhances freezing tolerance. Science 280, 104-106.

Jia, Y. and Martin, G.B. (Jun. 1999). Rapid transcript accumulation of pathogenesis-related genes during an incompatible interaction in bacterial speck disease-resistant tomato plants. Plant Molec. Biol. 40: 455-465.

Jofuku, K.D., et al. (1994). Control of *Arabidopsis* flower and seed development by the homeotic gene APETALA2. Plant Cell 6, 1211-1225.

Kaiser, T. and Batschauer A. (May 1995). Cis-acting elements of the CHS1 gene from white mustard controlling promoter activity and spatial patterns of expression. Plant Mol. Biol. 28:231-243.

Kaneko, et al. (Jun. 1999) Structural analysis of *Arabidopsis thaliana* chromosome 5. IX. Sequence features of the regions of 1,011,550 bp covered by seventeen P1 and TAC clones. DNA Res. 6(3):183-95.

Kasuga Mie et al. (Mar. 1999) "Improving plant drought, salt, and freezing tolerance by gene transfer of a single stress-inducible transcription factor" Nature Biotechnology, vol. 17, No. 3, pp. 287-291.

Lee, S.C., et al. (2004a). Ectopic expression of a cold-inducible transcription factor, CBF1/DREB1b, in transgenic rice (*Oryza sativa* L.). Mol Cells 18, 107-114.

Kennison (1995). The Polycomb and trithorax group proteins of *Drosophila*: transregulators of homeotic gene function. Annu. Rev. Genet. 29:289-303.

Kim et al. (Jun. 1997) Isolation of a novel class of bZIP transcription factors that interact with ABA-responsive and embryo-specification elements in the Dc3 promoter using a modified yeast one-hybrid system. Plant J. 11:1237-1251.

Kitajima, Sakihito, et al (Jun. 2000) Characterization of gene expression of NsERFs, transcription factors of basic PR genes from *Nicotiana sylvestris*. Plant and Cell Physiology, vol. 41, No. 6, pp. 817-824.

Klein et al., A new family of DNA binding proteins includes putative transcriptional regulators of . . . , Mol. Gen. Genet. (Jan. 15, 1996) 250:7-16.

Klug and Schwabe, Zinc fingers, FASEB J. (May 1995) 9:597-604.

Kranz, H.D. et al. (1998) Towards functional characterization of the members of the R2R3 MYB gene family from *Arabidopsis thaliana*. The Plant Journal vol. 16, No. 2, pp. 263-276.

Kuhlemeier et al., The Pea rbcS-3A Promoter Mediates Light Responsiveness but not Organ Specificity, The Plant Cell (Apr. 1989) 1:471-478.

Lacombe, et al. (2001). The Identity of Plant Glutamate Receptors. Science Journal, vol. 292: 1486-1487.

Lazar, et al. (1988). Transforming Growth Factor ox: Mutation of Aspartic Acid 47 and Leucine 48 Results in Different Biological Activities. Mol. Cell Biol. 8: 1247-1252.

Leckband, G. et al: "transformation and expression of a stilbene synthase gene of *Vitis vinifera* I. in barley and wheat for increased fungal resistance" theoretical and applied genetics, springer, Berlin, DE, vol. 96, No. 8, 1998, pp. 1004-1012, XP000923027.

Lee, J.H., et al. (2004b). The ethylene-responsive factor like protein 1 (CaERFLP1) of hot pepper (*Capsicum annuum* L.) interacts in vitro with both GCC and DRE/CRT sequences with different binding affinities: possible biological roles of CaERFLP1 in response to pathogen infection and high salinity . . . Plant Mol Biol 55, 61-81.

Lee J H. et al. (Oct. 1995), Derepression of the activity of genetically engineered heat shock factor causes constitutive synthesis of heat shock proteins and increased themotolerance in transgenic *Arabidopsis*. Plant Journal, vol. 8, No. 4, pp. 603-612.

Leggewie, G. et al. (1998). A cDNA from potato with homology to DNAJ is identical to a hitherto unidentified gene that is induced upon tuberization in potato and upon flowering in tobacco. Plant Physiol. 117, 1127.

Lin, et al. (Dec. 1999). Sequence and analysis of chromosome 2 of the plant *Arabidopsis thaliana*. Nature 402 (6763):761-768.

Littlewood et al. (1994) Transcription factors 2: helix-loop-helix. Prot. Profile 1:639-709.

Liu Qiang et al. (Aug. 1998) "Two transcription factors, DREB1 and DREB2, with an EREBP/AP2 DNA binding domain separate two cellular signal transduction pathways in drought-and low-termperature-responsive gene expression, respectivley, in *Arabidopsis*" Plant Cell 10: 1391-1406.

Lorenzo, O., et al. (2003). Ethylene Response Factor1 integrates signals from ethylene and jasmonate pathways in plant defense. Plant Cell 15, 165-178.

Lu and Ferl (Oct. 1995). The Electronic Plant Gene Register. Plant Physiol. 109:721-723.

Luo et al. (1996) Origin of floral asymmetry in *Antirrhinum*. Nature 383:794-799.

Ma and Ptashne (1987) A new class of yeast transcriptional activators. Cell 51:113-119.

Ma Q-H et al. (1998) Seed-specific expression of the isopentenyl transferase gene (IPT) in transgenic tobacco Austral. J Plant Physiol. 25: 53-59.

Martin, G.B., et al. (1993). Map-based cloning of a protein kinase gene conferring disease resistance in tomato. Science 262, 1432-1436.

Martin and Paz-Ares, MYB transcription factors in plants, Trends in Genetics (Feb. 1997) 13:67-73.

Mayer, K. et al. (2001) Conservation of microstructure between a sequenced region of the genome of rice and multiple segments of the genome of *Arabidopsis thaliana*. Genome Res. 11 (7), 1167-1174 (2001).

Mayer, et al. (Dec. 1999). Sequence and analysis of chromosome 4 of the plant *Arabidopsis thaliana*. Nature 402(6763):769-77.

Mazarei, et al. (Jun. 2002). Identification and characterization of a soybean ethylene-responsive element-binding protein gene whose mRNA expression changes during soybean cyst nematode infection. Mol. Plant Microbe Interact. 15(6):577-586.

Meissner, Ruth et al. (Oct. 1999) "Function search in a large transcription factor gene family in *Arabidopsis*: Assessing the potential of reverse genetics to identify insertional mutations in R2R3 MYB genes" Plant Cell vol. 11, No. 10, pp. 1827-1840.

Menke, et al. (1999). A novel jasmonate-and elicitor-responsive element in the periwinkle secondary metabolite biosynthetic gene Str interacts with a jasmonate-and elicitor-inducible AP2-domain transcription factor, ORCA2. EMBO J. 18 (16), 4455-4463.

Moore et al. (1998). A transcription activation system for regulated gene expression in transgenic plants Proc. Natl. Acad. Sci. 95:376-381.

Nakano,T., et al. (2006). Genome-wide analysis of the ERF gene family in *Arabidopsis* and rice. Plant Physiol. 140 (2), 411-432.

Newman, et al. (1994). Genes galore: a summary of methods for accessing results from large-scale partial sequencing of anonymous *Arabidopsis* cDNA clones (Plant Physiol. 106, 1241-1255 (1994)).

Odell et al. (Feb. 28, 1985). Identification of DNA sequences required for activity of the cauliflower mosaic virus 35S promoter. Nature 313:810-812.

Odell et al., Seed-Specific Gene Activation Mediated by the Cre/lox Site-Specific Recombination System, Plant Physiol. (Oct. 1994) 106:447-458.

Ohl et al., Functional Properties of a Phenylalanine Ammonia-Lyase Promoter from *Arabidopsis*, The Plant Cell (Sep. 1990) 2:837-848.

Ohme-Takagi, M., and Shinshi, H. (1990). Structure and expression of a tobacco a-1,3-glucanase gene. Plant Mol. Biol. 15, 941-946.

Ohme-Takagi, M., and Shinshi, H. (1995). Ethylene-inducible DNA binding proteins that interact with an ethylene-responsive element. Plant Cell 7, 173-182.

Ohta, et al. (2001) Repression domains of class II ERF transcriptional repressors share an essential motif for active repression. Plant Cell 13 (8), 1959-1968.

Okamuro, J.K., et al. (1997). The AP2 domain of APETALA2 defines a large new family of DNA binding proteins in *Arabidopsis*. Proc Natl Acad Sci U S A 94, 7076-7081.

Oldroyd et al. (Aug. 1998) Genetically engineered broad-spectrum disease resistance in tomato. Plant Biol. 95:10300-10305.

Onate-Sanchez, L., and Singh, K.B. (2002). Identification of *Arabidopsis* ethylene-responsive element binding factors with distinct induction kinetics after pathogen infection. Plant Physiol 128, 1313-1322.

NCBI acc. No. AAC27694 (gi: 2895184) (Feb. 19, 1998); Robert,L. S., et al. "CONSTANS homolog [*Brassica napus*]"; source: *Brassica napus* (rape); Title: "Conserved structure and function of the flowering time gene Constans in *Brassicaceae*" (Unpublished).

Park, J.M., et al. (2001). Overexpression of the tobacco Tsi1 gene encoding an EREBP/AP2-type transcription factor enhances resistance against pathogen attack and osmotic stress in tobacco. Plant Cell 13, 1035-1046.

Prandl, R., et al., (May 1998) HSF3, a new heat shock factor from *Arabidopsis thaliana*, derepresses the heat shock response and confers thermotolerance when overexpressed in transgenic plants. Molecular and General Genetics, vol. 258, pp. 269-278.

Quattrocchio, et al. (1998) Analysis of bHLH and MYB domain proteins: species-specific regulatory differences are caused by divergent evolution of target anthocyanin genes. The Plant Journal, vol. 13, No. 4, pp. 475-488.

Ratcliffe et al. (Mar. 1999) Separation of shoot and floral identity in *Arabidopsis*. Development vol. 126, pp. 1109-1120.

Reeves and Nissen (1990) J. Biol. Chem. 265:8573-8582.

Rensink, et al. (2005) Analyzing the potato abiotic stress transcriptome using expressed sequence tags. Genome 48 (4), 598-605.

Rice Chromosome 10 Sequencing Consortium (Jun. 2003) In-depth view of structure, activity, and evolution of rice chromosome 10. Science 300(5625):1566-9.

Riechmann, et al. (Aug. 1996). DNA-binding properties of *Arabidopsis* MADS domain homeotic proteins APETALA1, APETALA3, PISTILLATA and AGAMOUS. Nucleic Acids Research. vol. 24, No. 16, pp. 3134-3141.

Riechmann, et al. (May 1996) Dimerization specificity of *Arabidopsis* MADS domain homeotic proteins APETALA1, APETALA3, PISTILLATA, and AGAMOUS. Proc. Natl. Acad. Sci. USA. vol. 93, pp. 4793-4798.

Riechmann, J.L., and Meyerowitz, E.M. (1998). The AP2/EREBP family of plant transcription factors. Biol Chem 379, 633-646.

Riechmann, J.L., and Ratcliffe, O.J. (2000). A genomic perspective on plant transcription factors. Curr Opin Plant Biol 3, 423-434.

Riechmann and Meyerowitz (Oct. 1997) MADS domain proteins in plant development. Bio. Chem. 378:1079-1101.

Riechmann, et al. (Jul. 1997) Determination of floral organ identity by *Arabidopsis* MADS domain homeotic proteins AP1, AP3, PI, and AG is independent of their DNA-binding specificity. Molecular Biol. of the Cell, pp. 1243-1259.

Riechmann, J.L., et al. (2000). *Arabidopsis* transcription factors: genome-wide comparative analysis among eukaryotes. Science 290, 2105-2110.

Ringli et al., Specific interaction of the tomato bZIP transcription factor VSF-1 with a non-palindromic DNA sequence that controls vascular gene expression, Plant Mol. Biol. (Aug. 1998) 37:977-988.

Rouse et al., Changes in Auxin Response from Mutations in an AUX/IAA Gene, Science 279:1371 (Feb. 1998) 279:1371-1373.

Sakuma, Y., et al. (2002). DNA-binding specificity of the ERF/AP2 domain of Arabidopsis DREBs, transcription factors involved in dehydration- and cold-inducible gene expression. Biochem Biophys Res Commun 290, 998-1009.

Sakurai, et al. (Jan. 2005). RARGE: a large-scale database of RIKEN *Arabidopsis* resources ranging from transcriptome to phenome. Nucleic Acids Res. (2005), 33(Database Issue): D647-50.

Salmi, et al. (2005). Profile and analysis of gene expression changes during early development in germinating spores of *Ceratopteris richardii*. Plant Physiol. 138 (3), 1734-1745.

Sasaki, T. et al. (2002). The genome sequence and structure of rice chromosome 1. Nature 420 (6913), 312-316.

Sato, et al. (1998). Structural analysis of *Arabidopsis thaliana* chromosome 5. IV. Sequence features of the regions of 1,456,315 bp covered by nineteen physically assigned P1 and AC clones. DNA Rsearch, Universal Academy Press, JP, vol. 5, 1998, pp. 41-54.

Sato, et al. (2000). Structural analysis of *Arabidopsis thaliana* chromosome 5. X. Sequence features of the regions of 3,076,755 bp covered by sixty P1 and TAC clones. DNA Res. 7 (1), 31-63 (2000).

Sato, et. al. (Apr. 28, 2000). Structural analysis of *Arabidopsis thaliana* chromosome 3. I. Sequence features of the regions of 4,504,864 bp covered by sixty P1 and TAC clones. DNA Res. 7(2):131-135.

Schaffner and Sheen, Maize rbcS Promoter Depends on Sequence Elements Not Found in Dicot recS Promoters, The Plant Cell (Sep. 1991) 3:997-1012.

Seki, et al. (Epub Mar. 21, 2002). Functional annotation of a full-length Arabidopsis cDNA collection. Science Apr. 2002; 296(5565):141-5.

Shi et al., Gibberellin and abscisie acids regulate GAST1 expression at the level of transcription, Plant Mol. Biol. (Dec. 1998) 38:1053-1060.

Shin, R., et al. (2002). Ectopic expression of Tsi1 in transgenic hot pepper plants enhances host resistance to viral, bacterial, and oomycete pathogens. Mol Plant Microbe Interact 15, 983-989.

Siebertz et al. (1989) cis-analysis of the wound-inducible promoter wun1 in transgenic tobacco plants and histochemical localization of its expression. Plant Cell 1:961-968.

Smalle, J. (1998) The trihelix DNA-binding motif in higher plants is not restricted to the transcription factors GT-1 and GT-2. Proc. Natl. Acad. Sci. USA vol. 95, pp. 3318-3322.

Soares, M.B., et al. (1994). Construction and characterization of a normalized cDNA library. Proc. Natl. Acad. Sci. U.S.A. 91, 9228-9232.

Solano et al. (1998) "Nuclear events in ethylene signaling: a transcriptional cascade mediated by ethylene-insensitive3 and ethylene-response-factor1" Genes Devel. 12:3703-3714.

Solano et al. (1998). Ethylene gas: perception, signaling and response. Curr. Opin. Plant Biol. 1:393-398.

Souer et al. (Apr. 19, 1996). The No Apical Meristem Gene of *Petunia* is Required for Pattern Formation in Embryos and . . . , Cell 85:159-170.

Stepanova et al. (Oct. 2000) Ethylene signaling: from mutants to molecules. Curr. Opin. Plant Biol. 3:353-360.

Stockinger, E.J., et al. (1997). *Arabidopsis thaliana* CBF1 encodes an AP2 domain-containing transcriptional activator that binds to the C-repeat/DRE, a cis-acting DNA regulatory element that stimulates transcription in response to low temperature and water deficit. Proc Natl Acad Sci U S A 94, 1035-1040.

Sung et al. (Mar. 2000). Developmentally regulated expression of two MADS-box genes, MdMADS3 and MdMADS4, in the morphogenesis of flower buds and fruits in apple. Planta. vol. 210, pp. 519-528.

Sung et al. (Aug. 1999) Characterization of MdMADS2, a member of the *Squamosa* subfamily of genes, in apple. Plant Physiol. 120: 969-978.

Suzuki, Kaoru et al. (1998). Immediate early induction of mRNAs for ethylene-resonsive transcription factors in tobacco leaf strips after cutting. Plant Journal, 15: 657-665.

Tang, et al. (1999). Overexpression of Pto activates defense responses and confers broad resistance. Plant Cell 11 (1), 15-29.

Thara et al. (1999) *Pseudomonas syringae* pv tomato induces the expression of tomato EREBP-like genes pti4 and pti5 independent of ethylene, salicylate and jasmonate. Plant J. 20:475-483.

Theologis, et al. (Dec. 2000) Sequence and analysis of chromosome 1 of the plant *Arabidopsis thaliana*. Nature 408(6814):816-20.

Thilmony et al. (1995). Expression of the Tomato Pto Gene in Tobacco Enhances Resistance to *Pseudomonas syringae* pv tabaci Expressing avrPto. Plant Cell 7:1529-1536.

Tournier, B., et al. (2003). New members of the tomato ERF family show specific expression pattern and diverse DNA-binding capacity to the GCC box element. FEBS Lett 550: 149-154.

Tucker et al. (Jul. 1994) Crystal structure of the adenovirus DNA binding protein reveals a hook-on model for cooperative DNA binding. EMBO J. 13: 2994-3002.

Wada, T., et al (1997) "Epidermal cell differentiation in *Arabidopsis* determined by a Myb homolog, CPC"Science 277, No. 5329 1113-1116.

Wang Zhi-Yong et al: "(1997) A Myb-related transcription factor is involved in the phytochrome regulation of an *Arabidopsis* Lhcb gene" Plant Cell 9: 491-507.

Wang Z-Y et al (1998) "Constitutive expression of the Circadian Clock Associated 1 (CCA1) gene disrupts circadian rhythms and suppresses its own expression" Cell 93: 1207-1217.

Xu, P., et al. (1998). Identification of a novel DNA-binding protein to osmotin promoter. Science in China, Series C: Life Sciences, 41(6), 657-663.

Urao et al. (Nov. 1993) "An *Arabidopsis* MYB Homolog is induced by dehydration stress and its gene product binds to the conserved MYB recognition sequence." Plant Cell, 5: 1529-1539.

Van Der Fits and Memelink (2000). ORCA3, a jasmonate-responsive transcriptional regulator of plant primary and secondary metabolism. Science 289 (5477), 295-297.

Van Der Fits and Memelink (Jan. 2001). The jasmonate-inducible AP2/ERF-domain transcription factor ORCA3 activates gene expression via interaction with a jasmonate-responsive promoter element. Plant J. 25(1 ):43-53.

Van Der Kop et al., Selection of *Arabidopsis* mutants overexpressing genes driven by the promoter . . . , Plant Mol. Biol. (Mar. 1999) 39:979-990.

Weigel, D. (1995). The APETALA2 domain is related to a novel type of DNA binding domain. Plant Cell 7, 388-389.

White, et al. (2000) A new set of *Arabidopsis* expressed sequence tags from developing seeds. The metabolic pathway from carbohydrates to seed oil. Plant Physiol. 124 (4), 1582-1594.

Willmott et al., Dnase1 footprints suggest the involvement of at least three types of transcription factors in the regulation . . . , Plant Mol. Biol. (Nov. 1998) 38:817-825.

Winicov et al. (Dec. 1998) "New molecular approaches to improving salt tolerance in crop plants." Annals of Botany, vol. 82, No. 6, pp. 705-710.

Winicov Ilga et al., (Jun. 1999) Transgenic overexpression of the transcription factor Alfin1 enhances expression of the endogenous MsPRP2 gene in alfalfa and improves salinity tolerance of the plants. Plant Physiology vol. 120, No. 2, pp. 473-480.

Wu et al., The *Arabidopsis* 14-3-3 Multigene Family, Plant Physiol. (Aug. 1997) 114:1421-1431.

Wu et al. (Jan. 2002) Functional analysis of tomato Pti4 in *Arabidopsis*. Plant Physiol. 128:30-37.

Xu, et al. (Nov. 1998). A nitrilase-like protein interacts with GCC box DNA-binding proteins involved in ethylene and defense responses. Plant Physiol. 118(3):867-74.

Xue, G. et al. (2004) HvDRF1 is involved in abscisic acid-mediated gene regulation in barley and produces two forms of AP2 transcription activators, interacting preferably with a CT-rich element. The Plant Journal, vol. 37, pp. 326-339.

Yamada, K., et al. (2003). Empirical analysis of transcriptional activity in the *Arabidopsis* genome. Science 302 (5646), 842-846.

Shewmaker, C. K., et al: "Seed-specific overexpression of phytoene synthase: increase in carotenoids and other metabolic effects" Plant Journal, Blackwell Scientific Publications, Oxford, GB, vol. 20, No. 4, 1999, pp. 401-412, XP002969263 ISSN: 0960-7412.

Zhang et al., Expression of Antisense or Sense RNA of an Ankyrin Repeat-Containing Gene . . . , The Plant Cell (Dec. 1992) 4:1575-1588.

Zhou, J., et al. (1997). The Pto kinase conferring resistance to tomato bacterial speck disease interacts with proteins that bind a cis-element of pathogenesis-related genes. Embo J 16, 3207-3218.

Zhou et al. (1995). Molecular cloning of a small DNA binding protein with specificity for a tissue-specific negative element within the rps1 promoter. Nucleic Acids Res. 23:1165-1169.

Li, Z., et al: "PEI1, an embryo-specific zinc finger protein gene required for heart-stage embryo formation in *Arabidopsis*" Plant Cell, vol. 10, No. 3, Mar. 1998, pp. 383-398, XP002302043 ISSN: 1040-4651.

Robert, L.S., et al. (1998). Conserved structure and function of the *Arabidopsis* flowering time gene CONSTANS in *Brassica napus*. Plant Mol. Biol. 37 (5), 763-772 (1998).

Putterril, J.J., et al. The flowering-time gene CONSTANS and homologue CONSTANS Like 1 (accession Nos. Y10555 and Y10556) exist as a tandem repeat on chromosome 5 of *Arabidopsis* (PGR97-077) Plant Physiol. 114, 396-396 (1997).

U.S. Appl. No. 11/986,992, Kumimoto, R. et al., Entire document.

U.S. Appl. No. 12/157,329, Zhang, J. et al., Entire document.

U.S. Appl. No. 12/169,527, Zhang, J. et al., Entire document.

U.S. Appl. No. 12/154,154, Century, K. et al., Entire document.

U.S. Appl. No. 11/981,733, Ratcliffe, O. et al., Entire document.

\* cited by examiner

FIG. 2A

```
G4243 (1986)  MGEEVKTSEYD------------------EERVMEWEMGLPTANDLTPLSQPLIPPELASAFSI
G4244 (1988)  MGEEVKTSEYD------------------EERVMEWEAGLPTANDLTPLSQPLIPPELASAFSI
G4245 (1990)  MGEEVSLTDYES-----------SGGNDDRLLWEIGLPDVDDLTPLNMQLIPSELAAAFRI
G4241 (1992)  MGEEA-PEEYEL--------------GGGEDERVMEWEAGLPGADELTPLSQPLVPAGLAAAFRI
G4240 (1994)  MGEEA-VDDYELHMVCYGGGGGGSEDERVMEWESGLPGADELTPLSQPLVPAGLAAAFRI
G1435 (1796)  MGKEVMVSDYGDD---DGEDAGGGDEYRIPEWEIGLPNGDDLTPLSQYLVPSILALAFSM
G2741 (1984)  MGEEVQMSDY---------DVSGDGD--RVSEWEMGLPSDEDLASLSYSLIPPNLAMAFSI

G4243 (1986)  SPEPHRTLLEVNRASRNTLSTIRGGG--SVHQAFSSNNNNNHHYDGDGDGG-DEEEYDDA
G4244 (1988)  LPEPHRTLLDVNRASRNTLSTLRGGGG-SVHQAFSSNNN-HNYDGDGDGGVEEEEEEDD
G4245 (1990)  SPELSKTMTDVNRASQNTFSSLQRWHS-QDMASMNNSNFKTFSYERSREETVTERDETDL
G4241 (1992)  PPEPGRTLLDVHRASAATVSRLRRAS--SSS-----SSSFPAFASKGAG-AGADEAE----
G4240 (1994)  PPEAGRTLLDVHRASAATVSRLRRAPPSSSGSGSSSFAPFHPAARGDEGADSSA----
G1435 (1796)  IPERSRTIHDVNRASQITLSSLR-------SSTNASSVMEEVVDRVESSVPGSDPKKQKKS
G2741 (1984)  TPERSRTIQDVNRASETTLSSLRGGSS-GPNTSSSNNNVEEEDRVGSSSPGSDSKKQKTS

G4243 (1986)  DRDGSGSDSRKQRKIDCGVAEEAD--SAVRTETSAERTAVK----RPRLVWTPQLHKRFVD
G4244 (1988)  DRDGSGPDSRKQRKIDCGAAEEAD--SAVQTETSAERTAVK----RPRLVWTPQLHKRFVD
G4245 (1990)  IREGS--DSRKLRRVESGGTEEAD--SSLCNENFADDSSAKTLKRPRLVWTPQLHKRFIE
G4241 (1992)  -----------SGGGANGG-----NGNTNNNSS--------KRARLVWTPQLHKRFVE
G4240 (1994)  -----------AGGGAAATT----NGNNNMSSSS--------KRPRLVWTPQLHKRFVD
G1435 (1796)  --DGG---------EAAAVEDS--TAEEGDSGPEDASGKTSKRPRLVWTPQLHKRFVD
G2741 (1984)  NGDGD--------DGGGVDPDSAMAAEEGDSGTEDLSGKTLKRPRLVWTPQLHKRFVD
```

```
G4243 (1986) VVAHLGIKNAVPKTIMQLMNVEGLTRENVASHLQKYRLYLKRMQGLSNEGP---SSSDQLF
G4244 (1988) VVAHLGIKNAVPKTIMQLMNVEGLTRENVASHLQKYRLYLKRMQGLSNEGP---SASDQLF
G4245 (1990) VVAHLGIKGAVPKTIMQLMNVEGLTRENVAGHLQKYRLYTKRMQ---PNEGP---SSSDHLL
G4241 (1992) VVAHLGMKNAVPKTIMQLMNVEGLTRENVASHLQKYRLYVKRMQGLSNEGP---SPSDHIF
G4240 (1994) VVAHLGMKNAVPKTIMQLMNVEGLTRENVASHLQKYRLYVKRMQGLSDEGP---SPSDHIF
G1435 (1796) VVAHLGIKNAVPKTIMQLMNVEGLTRENVASHLQKYRLYLKRIQGLTTEEDPYSSSDQLF
G2741 (1984) VVAHLGIKNAVPKTIMQLMNVEGLTRENVASHLQKYRLYLKRMQGLTNEGP---SASDKLF

G4243 (1986) ASTAVPQSLHDSAPPSAHSN----------------GHGHLPVPMMSMPYPPPMMSMP
G4244 (1988) ASTPVPQSLHDSAPPSNHSNGHGHGHSNGRGHGHGHLSVPMMSMPYPPPLMSMP
G4245 (1990) TSTPATEIMRESSESGHLRN----------------TNGHMAMPTL-MPYQQQMVAMP
G4241 (1992) ASTPVPHASLHDQVPSPYHP----------------------------------
G4240 (1994) ASTPVPQSLVHEVPMYGTMAS----------------------------------
G1435 (1796) SSTPVPPQSFQD---GGGSN----------------GKLGVPVP----VPSMVP--
G2741 (1984) SSTPVPPQSFQDIGGGGGSS----------------GNVGVPIPGAYGTQQMQ--

G4243 (1986) YPPPMMSGMPHAHGHMGIPMPNSSAT------------SAYHPYNMLHQRDW
G4244 (1988) YPPPMMSGMP--HGHMGIPMPNSSAT------------SAYHPYNMLHQRDW
G4245 (1990) --------MMGMPN-GGHVGMPVGYGGGPPL-------GFHHHYNVVQQRDW
G4241 (1992) --------HPHHHSYNNAAYAATVSS------------YHHYHHANH---
G4240 (1994) --------GGQAYHNHNGMGGGGYQYQ-----------YHHYHHAHK---
G1435 (1796) --------IPGYGNQMGMQGYYQQYSNH------GN---ESNQYMMQQNKFG
G2741 (1984) --------MPVYAHHMGMQGYHHQNHHDPYHQNHRHHHGAGGNGAFESNPYMMQQNKFG
```

FIG. 2B

| | | |
|---|---|---|
| G4243 | (1986) | P-------HLAPNDK |
| G4244 | (1988) | P-------HLAPNDK |
| G4245 | (1990) | SGNNFGYYHPVASNDK |
| G4241 | (1992) | --------------- |
| G4240 | (1994) | --------------- |
| G1435 | (1796) | TMVTYPSVGGGDVNDK |
| G2741 | (1984) | SMASYPSVGGGSANEN |

FIG. 2C

TRANSCRIPTION FACTORS FOR INCREASING YIELD

RELATED APPLICATION INFORMATION

The present patent application is a continuation-in-part application of prior U.S. patent application Ser. No. 09/713,994, filed Nov. 16, 2000, which is now abandoned, and the present patent application claims the benefit of the following three U.S. provisional patent applications: application Ser. No. 60/166,228 filed Nov. 17, 1999; application Ser. No. 60/197,899, filed Apr. 17, 2000; and application Ser. No. 60/227,439, filed Aug. 22, 2000. The entire contents of each of these applications are hereby incorporated by reference.

JOINT RESEARCH AGREEMENT

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement, said agreement having been in effect on or before the date the claimed invention was made.

FIELD OF THE INVENTION

This invention relates to the field of plant biology. More particularly, the present invention pertains to compositions and methods for phenotypically modifying a plant.

BACKGROUND OF THE INVENTION

Transcription factors can modulate gene expression, either increasing or decreasing (inducing or repressing) the rate of transcription. This modulation results in differential levels of gene expression at various developmental stages, in different tissues and cell types, and in response to different exogenous (e.g., environmental) and endogenous stimuli throughout the life cycle of the organism.

Because transcription factors are key controlling elements of biological pathways, altering the expression levels of one or more transcription factors can change entire biological pathways in an organism. For example, manipulation of the levels of selected transcription factors may result in increased expression of economically useful proteins or metabolic chemicals in plants or to improve other agriculturally relevant characteristics such as to increase yield. Therefore, manipulating transcription factor levels in a plant offers tremendous potential in agricultural biotechnology for modifying a plant's traits such as improved yield from commercially important plant species.

One factor affecting yield is the number of plants that can be grown per acre. For crop species, planting or population density varies from a crop to a crop, from one growing region to another, and from year to year. Using corn as an example, the average prevailing density in 2000 was in the range of 20,000-25,000 plants per acre in Missouri, USA. A desirable higher population density (a measure of yield) would be at least 22,000 plants per acre, and a more desirable higher population density would be at least 28,000 plants per acre, more preferably at least 34,000 plants per acre, and most preferably at least 40,000 plants per acre. The average prevailing densities per acre of a few other examples of crop plants in the USA in the year 2000 were: wheat 1,000,000-1,500,000; rice 650,000-900,000; soybean 150,000-200,000, canola 260,000-350,000, sunflower 17,000-23,000 and cotton 28,000-55,000 plants per acre (Cheikh et al. (2003) U.S. Patent Application No. 20030101479). A desirable higher population density for each of these examples, as well as other valuable species of plants, would be at least 10% higher than the average prevailing density or yield.

The present invention provides novel transcription factors useful for modifying a plant's phenotype in desirable ways.

SUMMARY OF THE INVENTION

The present invention pertains to a transgenic plant having that has an improved trait relative to a control plant. The improved trait may include, for example, larger size, larger seeds, greater yield, darker green, increased rate of photosynthesis, more tolerance to osmotic stress, more drought tolerance, more heat tolerance, more salt tolerance, more cold tolerance, more tolerance to low nitrogen, early flowering, delayed flowering, more resistance to disease, more seed protein, and more seed oil relative to the control plant. The transgenic plant will generally comprise an expression vector that comprises a recombinant polynucleotide of the invention, that is, a nucleic acid sequence that encodes a polypeptide sequence that is related to any of SEQ ID NO: 110, 112, 116, 120, 124, 128, 131, 135, 139, 143, 147, 151, 155, 159, 163, 167, 171, 175, 179, 183, 187, 191, 195, 199, 203, 207, 211, 215, 219, 223, 227, 231, 235, 239, 243, 247, 251, 255, 259, 263, 267, 271, 275, 280, 284, 288, 292, 296, 299, 303, 306, 309, 313, 317, 321, 325, 329, 333, 337, 341, 345, 349, 353, 357, 361, 365, 369, 373, 377, 381, 385, 389, 393, 397, 401, 404, 406, 409, 413, 416, 419, 422, 425, 428, 431, 435, 439, 443, 447, 451, 454, 458, 462, 465, 468, 471, 475, 478, 482, 485, 489, 493, 497, 501, 505, 509, 512, 515, 519, 522, 526, 530, 534, 538, 542, 546, 550, 553, 557, 561, 565, 568, 571, 574, 577, 581, 585, 588, 591, 594, 597, 601, 605, 609, 613, 616, 620, 624, 628, 632, 636, 640, 644, 648, 652, 656, 660, 664, 667, 671, 674, 678, 682, 686, 689, 692, 696, 700, 704, 708, 712, 715, 719, 723, 727, 731, 734, 738, 741, 745, 749, 752, 756, 760, 762, 766, 770, 774, 778, 782, 786, 789, 793, 797, 801, 805, 809, 813, 816, 819, 823, 827, 831, 835, 839, 843, 847, 851, 855, 859, 863, 867, 871, 874, 878, 882, 886, 890, 894, 898, 901, 905, 909, 913, 917, 921, 925, 929, 933, 937, 941, 945, 949, 953, 957, 960, 963, 966, 970, 973, 976, 980, 984, 988, 992, 995, 999, 1003, 1007, 1011, 1015, 1019, 1023, 1027, 1031, 1037, 1041, 1045, 1049, 1052, 1056, 1060, 1064, 1067, 1071, 1075, 1078, 1081, 1085, 1089, 1093, 1097, 1101, 1104, 1108, 1112, 1116, 1120, 1123, 1126, 1130, 1134, 1138, 1142, 1145, 1148, 1151, 1154, 1157, 1161, 1165, 1169, 1173, 1177, 1181, 1185, 1188, 1192, 1195, 1199, 1203, 1207, 1211, 1215, 1219, 1222, 1226, 1229, 1233, 1236, 1240, 1243, 1247, 1251, 1254, 1258, 1262, 1266, 1269, 1273, 1277, 1281, 1285, 1289, 1293, 1297, 1300, 1304, 1308, 1311, 1314, 1318, 1322, 1326, 1330, 1334, 1338, 1342, 1346, 1350, 1354, 1358, 1361, 1365, 1369, 1372, 1376, 1380, 1384, 1388, 1392, 1396, 1400, 1404, 1408, 1411, 1415, 1419, 1423, 1427, 1431, 1435, 1439, 1443, 1446, 1449, 1452, 1455, 1459, 1463, 1467, 1470, 1474, 1477, 1481, 1488, 1492, 1495, 1499, 1503, 1507, 1511, 1515, 1519, 1522, 1526, 1530, 1533, 1537, 1541, 1545, 1549, 1553, 1557, 1561, 1565, 1568, 1572, 1576, 1579, 1583, 1586, 1589, 1593, 1596, 1598, 1602, 1604, 1608, 1611, 1614, 1617, 1620, 1624, 1628, 1632, 1636, 1640, 1645, 1648, 1652, 1656, 1660, 1664, 1668, 1672, 1676, 1680, 1684, 1688, 1692, 1696, 1700, 1704, 1707, 1711, 1715, 1719, 1722, 1726, 1729, 1733, 1737, 1741, 1745, 1749, 1753, 1757, 1761, 1765, 1769, 1773, 1777, 1781, 1785, 1789, 1793, 1796, 1800, 1803, 1806, 1809, 1812, 1816, 1820, 1824, 1827, 1831, 1835, 1838, 1841, 1844, 1846, 1850, 1853, 1857, 1861, 1865, 1869, 1873, 1877, 1881, 1885, 1889, 1893, 1897, 1901, 1904, 1908, 1912, 1916, 1920, 1924, 1928, 1932, 1935, 1939, 1943, 1949, 1957, 1961, 1964, 1967, 1970, 1973, 1977, 1981, 1984, 1986, 1988, 1990, 1992, 1994, 1996, 1998; and 1999-2007. Sequences that are related to the polypeptides listed in the sequence listing will have at least 46%, or at least 50%, or at least 53%, or at least 56%, or at least 61%, or at least 80%, or at least 85%, or at least 90%, or at least 100% amino acid identity to the polypeptides of the sequence listing, or comprise a conserved domain at least 80%, or at least 91%, or at least 95%, or at least 97%, or at least 100% identical to the conserved domain of a polypeptide selected from the sequence listing. The conserved domains of the polypeptides of the invention and/or found within the sequence listing are required for the function of regulating transcription and altering a trait in a transgenic plant. Transgenic plants of the invention that comprise polypeptides of the invention will have improved traits, relative to a control plant, said improved traits including larger size, larger seeds, greater yield, darker green color, increased rate of photosynthesis, more tolerance to osmotic stress, more drought tolerance, more heat tolerance, more salt tolerance, more cold tolerance, more tolerance to low nitrogen, early flowering, delayed flowering, more resistance to disease, more seed protein, and/or more seed oil relative to the control plant. The invention is also directed to methods for producing a transgenic plant, or increasing the size, yield, photosynthetic rate or yield of a plant. These methods are carried out with a target plant that is then transformed with an expression vector that encodes a polypeptide with a conserved domain at least 91%, 95%, or 97% identical to SEQ ID NO: 1995, the conserved domain of amino acids 146-194 of the G1435 polypeptide, SEQ ID NO: 1796, thus producing the transgenic plant.

BRIEF DESCRIPTION OF THE SEQUENCE LISTING AND DRAWINGS

FIG. 1 shows a conservative estimate of phylogenetic relationships among the orders of flowering plants (modified from Angiosperm Phylogeny Group (1998) Ann. Missouri Bot. Gard. 84: 1-49). Those plants with a single cotyledon (monocots) are a monophyletic clade nested within at least two major lineages of dicots; the eudicots are further divided into rosids and asterids. Arabidopsis is a rosid eudicot classified within the order Brassicales; rice is a member of the monocot order Poales. FIG. 1 was adapted from Daly et al. (2001) Plant Physiol. 127: 1328-1333.

FIGS. 2A-2C show a Clustal W alignment of the G1435 clade. SEQ ID NOs: appear in parentheses after each Gene IDentifier (GID). The highly conserved GARP domain is identified in FIGS. 2A-2B by the box that appears around the residues within these domains.

The Sequence Listing provides exemplary polynucleotide and polypeptide sequences of the invention. CD-ROMs Copy 1 and Copy 2, and the CRF copy of the Sequence Listing under CFR Section 1.821(e), are read-only memory computer-readable compact discs. Each contains a copy of the Sequence Listing in ASCII text format. The Sequence Listing is named "MB10022-2CIP.ST25.txt", the electronic file of the Sequence Listing contained on each of these CD-ROMs was created on Jun. 30, 2006, and is 4299 kilobytes in size. The copies of the Sequence Listing on the CD-ROM discs are hereby incorporated by reference in their entirety.

DETAILED DESCRIPTION

The present invention relates to polynucleotides and polypeptides, e.g. for modifying phenotypes of plants.

The polynucleotides of the invention encode plant transcription factors. The plant transcription factors are derived, e.g., from *Arabidopsis thaliana* and can belong, e.g., to one or more of the following transcription factor families: the AP2 (APETALA2) domain transcription factor family (Riechmann and Meyerowitz (1998) *J. Biol. Chem.* 379:633-646); the MYB transcription factor family (Martin and Paz-Ares (1997) *Trends Genet.* 13:67-73); the MADS domain transcription factor family (Riechmann and Meyerowitz (1997) *J. Biol. Chem.* 378:1079-1101); the WRKY protein family (Ishiguro and Nakamura (1994) *Mol. Gen. Genet.* 244:563-571); the ankyrin-repeat protein family (Zhang et al. (1992) *Plant Cell* 4:1575-1588); the miscellaneous protein (MISC) family (Kim et al. (1997) *Plant J.* 11:1237-1251); the zinc finger protein (Z) family (Klug and Schwabe (1995) *FASEB J.* 9: 597-604); the homeobox (HB) protein family (Duboule (1994) *Guidebook to the Homeobox Genes*, Oxford University Press); the CAAT-element binding proteins (Forsburg and Guarente (1989) *Genes Dev.* 3:1166-1178); the squamosa promoter binding proteins (SPB) (Klein et al. (1996) *Mol. Gen. Genet.* 1996 250:7-16); the NAM protein family; the IAA/AUX proteins (Rouse et al. (1998) *Science* 279:1371-1373); the HLH/MYC protein family (Littlewood et al. (1994) *Prot. Profile* 1:639-709); the DNA-binding protein (DBP) family (Tucker et al. (1994) *EMBO J.* 13:2994-3002); the bZIP family of transcription factors (Foster et al. (1994) *FASEB J.* 8:192-200); the BPF-1 protein (Box P-binding factor) family (da Costa e Silva et al. (1993) *Plant J.* 4:125-135); and the golden protein (GLD) family (Hall et al. (1998) *Plant Cell* 10:925-936).

In addition to methods for modifying a plant phenotype by employing one or more polynucleotides and polypeptides of the invention described herein, the polynucleotides and polypeptides of the invention have a variety of additional uses. These uses include their use in the recombinant production (i.e, expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like, of as substrates for cloning e.g., including digestion or ligation reactions, and for identifying exogenous or endogenous modulators of the transcription factors.

Definitions

A "polynucleotide" is a nucleic acid sequence comprising a plurality of polymerized nucleotide residues, e.g., at least about 15 consecutive polymerized nucleotide residues, optionally at least about 30 consecutive nucleotides, at least about 50 consecutive nucleotides. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "recombinant polypeptide" is a polypeptide produced by translation of a recombinant polynucleotide. An "isolated polypeptide," whether a naturally occurring or a recombinant polypeptide, is more enriched in (or out of) a cell than the polypeptide in its natural state in a wild type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type or other control standardized at 100%. Such an enrichment is not the result of a natural response of a wild type or other control plant. Alternatively, or additionally, the isolated polypeptide is separated from other cellular components with which it is typically associated, e.g., by any of the various protein purification methods herein.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, Daly et al. (2001) *Plant Physiol.* 127: 1328-1333 (2001), adapted from Ku et al. (2000) *Proc. Natl. Acad. Sci. USA* 97: 9121-9126; and see also Tudge (2000) in *The Variety of Life*, Oxford University Press, New York, N.Y. pp. 547-606.

The term "transgenic plant" refers to a plant that contains genetic material, not found in a control plant such as a wild type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation.

A transgenic plant may contain an expression vector or cassette. The expression cassette typically comprises a polypeptide-encoding sequence operably linked (i.e., under regulatory control of) to appropriate inducible or constitutive regulatory sequences that allow for the expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

The phrase "ectopically expression or altered expression" in reference to a polynucleotide indicates that the pattern of expression in, e.g., a transgenic plant or plant tissue, is different from the expression pattern in a wild type plant, control plant, or a reference plant of the same species. For example, the polynucleotide or polypeptide is expressed in a cell or tissue type other than a cell or tissue type in which the sequence is expressed in the control or wild type plant, or by expression at a time other than at the time the sequence is expressed in the control or wild type plant, or by a response to different inducible agents, such as hormones or environmental signals, or at different expression levels (either higher or lower) compared with those found in a control or wild type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "fragment" or "domain," with respect to a polypeptide, refers to a subsequence of the polypeptide. In some cases, the fragment or domain, is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA binding domain that binds to a DNA promoter region, an activation domain or a domain for protein-protein interactions. Fragments can vary in size from as few as 6 amino acids to the full length of the intact polypeptide, but are preferably at least about 30 amino acids in length and more preferably at least about 60 amino acids in length. In reference to a nucleotide sequence, "a fragment" refers to any subsequence of a polynucleotide, typically, of at least consecutive about 15 nucleotides, preferably at least about 30 nucleotides, more preferably at least about 50, of any of the sequences provided herein.

A "conserved domain" or "conserved region" as used herein refers to a region in heterologous polynucleotide or polypeptide sequences where there is a relatively high degree of sequence identity between the distinct sequences. A "GARP" domain", such as is found in a polypeptide member of GARP family, is an example of a conserved domain. With respect to polynucleotides encoding presently disclosed polypeptides, a conserved domain is preferably at least nine base pairs (bp) in length. A conserved domain with respect to presently disclosed polypeptides refers to a domain within a polypeptide family that exhibits a higher degree of sequence homology, such as at least about 80% sequence identity, or at least about 91% sequence identity, or at least about 95% sequence identity, or at least about 97% amino acid residue sequence identity, to a conserved domain of a polypeptide of the invention (e.g., SEQ ID NOs: 1999-2007). Sequences that possess or encode for conserved domains that meet these criteria of percentage identity, and that have comparable biological activity to the present polypeptide sequences, for example, those sequences that are members of the G1435 clade polypeptides, are encompassed by the invention. A fragment or domain can be referred to as outside a conserved domain, outside a consensus sequence, or outside a consensus DNA-binding site that is known to exist or that exists for a particular polypeptide class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al. (2000a) *Science* 290, 2105-2110; Riechmann, J. L., and Ratcliffe, O. J. (2000b) *Curr. Opin. Plant Biol.* 3, 423-434). Thus, by using alignment methods well known in the art, the conserved domains of the plant polypeptides, for example, for the GARP family of transcription factors), may be determined.

The polypeptide may comprise 1) a localization domain, 2) an activation domain, 3) a repression domain, 4) an oligomerization domain, or 5) a DNA-binding domain, or the like. The conserved domains of the polypeptides of the invention and/or that are found within the sequence listing are required for the function of regulating transcription and altering a trait in a transgenic plant of the invention. Altered traits that may be conferred to a transgenic plant of the invention may include larger size, larger seeds, greater yield, darker green, increased rate of photosynthesis, more tolerance to osmotic stress, more drought tolerance, more heat tolerance, more salt tolerance, more cold tolerance, more tolerance to low nitrogen, early flowering, delayed flowering, more resistance to disease, more seed protein, and more seed oil relative to a control plant.

Conserved domains for some examples of polypeptide sequences of the invention are listed in Table 4. Also, the polypeptides of Table 4 have conserved domains specifically indicated by amino acid coordinate start and stop sites. A comparison of the regions of these polypeptides allows one of skill in the art (see, for example, Reeves and Nissen (1990) *J. Biol. Chem.* 265, 8573-8582) to identify domains or conserved domains for any of the polypeptides listed or referred to in this disclosure.

The term "trait" refers to a physiological, morphological, biochemical or physical characteristic of a plant or particular plant material or cell. In some instances, this characteristic is visible to the human eye, such as seed or plant size, or can be measured by available biochemical techniques, such as the protein, starch or oil content of seed or leaves or by the observation of the expression level of genes, e.g., by employing Northern analysis, RT-PCR, microarray gene expression assays or reporter gene expression systems, or by agricultural observations such as stress tolerance, yield or pathogen tolerance.

"Trait modification" refers to a detectable difference in a characteristic in a plant ectopically expressing a polynucleotide or polypeptide of the present invention relative to a plant not doing so, such as a control or wild type plant. In some cases, the trait modification can be evaluated quantitatively. For example, the trait modification can entail at least about a 2% increase or decrease in an observed trait (difference), at least a 5% difference, at least about a 10% difference, at least about a 20% difference, at least about a 30%, at least about a 50%, at least about a 70%, or at least about a 100%, or an even greater difference. It is known that there can be a natural variation in the modified trait. Therefore, the trait modification observed entails a change of the normal distribution of the trait in the plants compared with the distribution observed in a control or a wild type plant.

Trait modifications of particular interest include those to seed (such as embryo or endosperm), fruit, root, flower, leaf, stem, shoot, seedling or the like, including: enhanced tolerance to environmental conditions including freezing, chilling, heat, drought, water saturation, radiation and ozone; improved tolerance to microbial, fungal or viral diseases; improved tolerance to pest infestations, including nematodes, mollicutes, parasitic higher plants or the like; decreased herbicide sensitivity; improved tolerance of heavy metals or enhanced ability to take up heavy metals; improved growth under poor photoconditions (e.g., low light and/or short day length), or changes in expression levels of genes of interest. Other phenotype that can be modified relate to the production of plant metabolites, such as variations in the production of taxol, tocopherol, tocotrienol, sterols, phytosterols, vitamins, wax monomers, anti-oxidants, amino acids, lignins, cellulose, tannins, prenyllipids (such as chlorophylls and carotenoids), glucosinolates, and terpenoids, enhanced or compositionally altered protein or oil production (especially in seeds), or modified sugar (insoluble or soluble) and/or starch composition. Physical plant characteristics that can be modified include cell development (such as the number of trichomes), fruit and seed size and number, yields of plant parts such as stems, leaves and roots, the stability of the seeds during storage, characteristics of the seed pod (e.g., susceptibility to shattering), root hair length and quantity, internode distances, or the quality of seed coat. Plant growth characteristics that can be modified include growth rate, germination rate of seeds, vigor of plants and seedlings, leaf and flower senescence, male sterility, apomixis, flowering time, flower abscission, rate of nitrogen uptake, biomass or transpiration characteristics, as well as plant architecture characteristics such as apical dominance, branching patterns, number of organs, organ identity, organ shape or size.

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

Polypeptides and Polynucleotides of the Invention

The present invention provides, among other things, transcription factors (TFs), and transcription factor homologue polypeptides, and isolated or recombinant polynucleotides encoding the polypeptides. These polypeptides and polynucleotides may be employed to modify a plant's characteristic.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides of the invention were identified by screening *Arabidopsis thaliana* and/or other plant cDNA libraries with probes corresponding to known transcription factors under low stringency hybridization conditions. Additional sequences, including full length coding sequences were subsequently recovered by the rapid amplification of cDNA ends (RACE) procedure, using a commercially available kit according to the manufacturer's instructions. Where necessary, multiple rounds of RACE are performed to isolate 5' and 3' ends. The full length cDNA was then recovered by a routine end-to-end polymerase chain reaction (PCR) using primers specific to the isolated 5' and 3' ends. Exemplary sequences are provided in the Sequence Listing.

The polynucleotides of the invention were ectopically expressed in overexpressor or knockout plants and changes in the characteristics of the plants were observed. Therefore, the polynucleotides and polypeptides can be employed to improve the characteristics of plants.

Making Polynucleotides

The polynucleotides of the invention include sequences that encode transcription factors and transcription factor homologue polypeptides and sequences complementary thereto, as well as unique fragments of coding sequence, or sequence complementary thereto. Such polynucleotides can be, e.g., DNA or RNA, e.g., mRNA, cRNA, synthetic RNA, genomic DNA, cDNA synthetic DNA, oligonucleotides, etc. The polynucleotides are either double-stranded or single-stranded, and include either, or both sense (i.e., coding) sequences and antisense (i.e., non-coding, complementary) sequences. The polynucleotides include the coding sequence of a transcription factor, or transcription factor homologue polypeptide, in isolation, in combination with additional coding sequences (e.g., a purification tag, a localization signal, as a fusion-protein, as a pre-protein, or the like), in combination with non-coding sequences (e.g., introns or inteins, regulatory elements such as promoters, enhancers, terminators, and the like), and/or in a vector or host environment in which the polynucleotide encoding a transcription factor or transcription factor homologue polypeptide is an endogenous or exogenous gene.

A variety of methods exist for producing the polynucleotides of the invention. Procedures for identifying and isolating DNA clones are well known to those of skill in the art, and are described in, e.g., Berger and Kimmel, *Guide to Molecular Cloning Techniques, Methods in Enzymology* volume 152 Academic Press, Inc., San Diego, Calif. ("Berger"); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2000) ("Ausubel").

Alternatively, polynucleotides of the invention, can be produced by a variety of in vitro amplification methods adapted to the present invention by appropriate selection of specific or degenerate primers. Examples of protocols sufficient to direct persons of skill through in vitro amplification methods, including the polymerase chain reaction (PCR) the ligase chain reaction (LCR), Qbeta-replicase amplification and other RNA polymerase mediated techniques (e.g., NASBA), e.g., for the production of the homologous nucleic acids of the invention are found in Berger, Sambrook, and Ausubel, as well as Mullis et al., (1987) *PCR Protocols A Guide to Methods and Applications* (Innis et al. eds) Academic Press Inc. San Diego, Calif. (1990) (Innis). Improved methods for cloning in vitro amplified nucleic acids are described in Wallace et al., U.S. Pat. No. 5,426,039. Improved methods for amplifying large nucleic acids by PCR are summarized in Cheng et al. (1994) *Nature* 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Alternatively, polynucleotides and oligonucleotides of the invention can be assembled from fragments produced by solid-phase synthesis methods. Typically, fragments of up to approximately 100 bases are individually synthesized and then enzymatically or chemically ligated to produce a desired sequence, e.g., a polynucleotide encoding all or part of a transcription factor. For example, chemical synthesis using the phosphoramidite method is described, e.g., by Beaucage et al. (1981) *Tetrahedron Letters* 22:1859-69; and Matthes et al. (1984) *EMBO J.* 3:801-5. According to such methods, oligonucleotides are synthesized, purified, annealed to their complementary strand, ligated and then optionally cloned into suitable vectors. And if so desired, the polynucleotides and polypeptides of the invention can be custom ordered from any of a number of commercial suppliers.

Table 1 provides exemplary polynucleotide sequences of the invention. The table includes from left to right for each sequence: the SEQ ID No., the internal code reference number (GID), where the coding sequence is initiated and where the coding sequence terminates, and identification of any conserved domains for the translated polypeptide sequences maintaining the same coordinates of the polynucleotide sequence.

TABLE 1

Exemplary Polynucleotide Sequences of the Invention

| SEQ ID No. | GID | Coding Sequence Coordinates | Conserved Domain(s) in Amino Acid Coordinates |
|---|---|---|---|
| 1 | G188 | 50 ... 1096 | 175-222 |
| 2 | G616 | 129 ... 1211 | 39-95 |
| 3 | G19 | 70 ... 816 | 76-145 |
| 4 | G261 | 458 ... 1663 | 16-104 |
| 5 | G28 | 63 ... 869 | 145-213 |
| 6 | G869 | 428 ... 1402 | 109-177 |
| 7 | G237 | 1 ... 852 | 11-113 |
| 8 | G409 | 331 ... 1149 | 64-124 |
| 9 | G418 | 103 ... 2322 | 500-560 |
| 10 | G591 | 88 ... 1020 | 143-240 |
| 11 | G525 | 109 ... 966 | 23-167 |
| 12 | G545 | 55 ... 738 | 82-102, 136-154 |
| 13 | G865 | 282 ... 920 | 36-103 |
| 14 | G881 | 76 ... 1008 | 176-233 |
| 15 | G896 | 47 ... 1150 | 18-39 |
| 16 | G378 | 1 ... 726 | 196-237 |
| 17 | G569 | 184 ... 969 | 90-153 |
| 18 | G558 | 267 ... 1259 | 45-105 |
| 19 | G22 | 81 ... 761 | 89-157 |
| 20 | G225 | 157 ... 441 | 39-76 |
| 21 | G226 | 10 ... 348 | 28-78 |
| 22 | G256 | 312 ... 1310 | 13-115 |
| 23 | G419 | 381 ... 2213 | 392-452 |
| 24 | G464 | 41 ... 664 | 7-15, 70-80, 125-158, 183-219 |
| 25 | G482 | 188 ... 760 | 25-116 |
| 26 | G502 | 224 ... 1093 | 10-155 |

TABLE 1-continued

Exemplary Polynucleotide Sequences of the Invention

| SEQ ID No. | GID | Coding Sequence Coordinates | Conserved Domain(s) in Amino Acid Coordinates |
|---|---|---|---|
| 27 | G526 | 181 ... 1188 | 21-149 |
| 28 | G561 | 86 ... 1168 | 248-308 |
| 29 | G664 | 104 ... 952 | 13-116 |
| 30 | G682 | 1 ... 228 | 22-53 |
| 31 | G911 | 1 ... 480 | 86-129 |
| 32 | G964 | 162 ... 1013 | 126-186 |
| 33 | G394 | 82 ... 918 | 121-182 |
| 34 | G489 | 33 ... 695 | 57-156 |
| 35 | G214 | 238 ... 2064 | 22-71 |
| 36 | G229 | 41 ... 1156 | 14-120 |
| 37 | G241 | 46 ... 867 | 14-114 |
| 38 | G663 | 113 ... 862 | 9-111 |
| 39 | G776 | 76 ... 1431 | 27-175 |
| 40 | G778 | 50 ... 1249 | 220-267 |
| 41 | G883 | 67 ... 1041 | 245-302 |
| 42 | G938 | 1 ... 1755 | 96-104 |
| 43 | G1328 | 67 ... 1041 | 14-119 |
| 44 | G584 | 40 ... 1809 | 401-494 |
| 45 | G668 | 1 ... 1056 | 13-113 |
| 46 | G727 | 43 ... 1977 | 226-269 |
| 47 | G732 | 73 ... 588 | 31-91 |
| 48 | G9 | 81 ... 1139 | 62-127 |
| 49 | G428 | 97 ... 1032 | 229-292 |
| 50 | G1269 | 88 ... 951 | 27-83 |
| 51 | G1038 | 240 ... 1574 | 198-247 |
| 52 | G438 | 188 ... 2716 | 22-85 |
| 53 | G571 | 326 ... 1708 | 160-220 |
| 54 | G748 | 98 ... 1444 | 112-140 |
| 55 | G431 | 1 ... 1149 | 286-335 |
| 56 | G187 | 118 ... 1074 | 172-228 |
| 57 | G470 | 1 ... 2580 | 61-393 |
| 58 | G615 | 197 ... 1252 | 88-147 |
| 59 | G1073 | 62 ... 874 | 33-42, 78-175 |
| 60 | G26 | 73 ... 729 | 67-134 |
| 61 | G38 | 149 ... 1156 | 76-143 |
| 62 | G43 | 38 ... 643 | 104-172 |
| 63 | G207 | 16 ... 930 | 6-106 |
| 64 | G254 | 15 ... 923 | 62-106 |
| 65 | G263 | 48 ... 902 | 15-105 |
| 66 | G308 | 196 ... 1794 | 270-274 |
| 67 | G536 | 1 ... 768 | 226-233 |
| 68 | G680 | 338 ... 2275 | 24-70 |
| 69 | G867 | 64 ... 1098 | 59-124 |
| 70 | G912 | 20 ... 694 | 51-118 |
| 71 | G996 | 53 ... 1063 | 14-114 |
| 72 | G1068 | 150 ... 1310 | 143-150 |
| 73 | G1337 | 97 ... 1398 | 9-75 |
| 74 | G231 | 88 ... 888 | 14-118 |
| 75 | G274 | 172 ... 2037 | 108-572 |
| 76 | G307 | 1 ... 1764 | 323-339 |
| 77 | G346 | 1 ... 825 | 196-221 |
| 78 | G598 | 248 ... 1039 | 205-263 |
| 79 | G605 | 72 ... 1076 | 132-143 |
| 80 | G777 | 54 ... 914 | 47-101 |
| 81 | G1133 | 104 ... 1084 | 256-326 |
| 82 | G1266 | 62 ... 718 | 79-147 |
| 83 | G1324 | 54 ... 914 | 20-118 |
| 84 | G975 | 58 ... 657 | 4-71 |
| 85 | G157 | 31 ... 621 | 2-57 |
| 86 | G859 | 132 ... 569 | 2-57 |
| 87 | G1842 | 219 ... 809 | 2-57 |
| 88 | G1843 | 51 ... 653 | 2-57 |
| 89 | G1844 | 39 ... 635 | 2-57 |
| 90 | G861 | 158 ... 880 | 2-57 |
| 91 | G192 | 63 ... 959 | 128-185 |
| 92 | G234 | 106 ... 1035 | 14-115 |
| 93 | G361 | 54 ... 647 | 43-63 |
| 94 | G486 | 1 ... 420 | 5-66 |
| 95 | G994 | 180 ... 917 | 14-123 |
| 96 | G1335 | 56 ... 667 | 24-43, 131-144, 185-203 |
| 97 | G562 | 137 ... 1285 | 253-315 |
| 98 | G736 | 1 ... 513 | 54-111 |
| 99 | G1435 | 8 ... 904 | 146-194 |
| 100 | G180 | 54 ... 629 | 118-174 |
| 101 | G592 | 121 ... 1200 | 290-342 |
| 102 | G208 | 15 ... 725 | 14-116 |
| 103 | G658 | 17 ... 757 | 2-105 |
| 104 | G1334 | 76 ... 885 | 18-190 |
| 105 | G27 | 83 ... 622 | 37-104 |
| 106 | G740 | 25 ... 924 | 24-42, 232-268 |
| 107 | G559 | 89 ... 1285 | 203-264 |
| 108 | G1093 | 1 ... 531 | 105-148 |
| 109 | G725 | 46 ... 1122 | 39-87 |

Orthologs and Paralogs

Sequences homologous, i.e., that share significant sequence identity or similarity, to those provided in the Sequence Listing, derived from *Arabidopsis thaliana* or from other plants of choice are also an aspect of the invention. Homologous sequences can be derived from any plant including monocots and dicots and in particular agriculturally important plant species, including but not limited to, crops such as soybean, wheat, corn, potato, cotton, rice, oilseed rape (including canola), sunflower, alfalfa, sugarcane and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, spinach, squash, sweet corn, tobacco, tomato, watermelon, rosaceous fruits (such as apple, peach, pear, cherry and plum) and vegetable brassicas (such as broccoli, cabbage, cauliflower, Brussels sprouts and kohlrabi). Other crops, fruits and vegetables whose phenotype can be changed include barley, rye, millet, sorghum, currant, avocado, citrus fruits such as oranges, lemons, grapefruit and tangerines, artichoke, cherries, nuts such as the walnut and peanut, endive, leek, roots, such as arrowroot, beet, cassava, turnip, radish, yam, and sweet potato, and beans. The homologous sequences may also be derived from woody species, such pine, poplar and eucalyptus.

Homologous sequences as described above can comprise orthologous or paralogous sequences. Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

As described by Eisen (1998) *Genome Res.* 8: 163-167, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen, supra). In fact, many specific examples exist in which gene function has been shown to correlate well with gene phylogeny (Eisen, supra). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, supra).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL Thompson et al. (1994) *Nucleic Acids Res.* 22: 4673-4680; et al. (1996) *Methods Enzymol.* 266: 383-402). Groups of similar genes can also be identified with pair-wise BLAST analysis (Feng and Doolittle (1987) *J. Mol. Evol.* 25: 351-360). For example, a clade of very similar MADS domain transcription factors from *Arabidopsis* all share a common function in flowering time (Ratcliffe et al. (2001) *Plant Physiol.* 126: 122-132), and a group of very similar AP2 domain transcription factors from *Arabidopsis* are involved in tolerance of plants to freezing (Gilmour et al. (1998) *Plant J.* 16: 433-442). Analysis of groups of similar genes with similar function that fall within one clade can yield sub-sequences that are particular to the clade. These sub-sequences, known as consensus sequences, can not only be used to define the sequences within each lade, but define the functions of these genes; genes within a clade may contain paralogous sequences, or orthologous sequences that share the same function (see also, for example, Mount (2001), in *Bioinformatics: Sequence and Genome Analysis*, Cold Spring Harbor Laboratory Press, Cold Spring Harbor, N.Y., p. 543).

Transcription factor gene sequences are conserved across diverse eukaryotic species lines (Goodrich et al. (1993) Cell 75: 519-530); Lin et al. (1991) Nature 353: 569-571; Sadowski et al. (1988) *Nature* 335: 563-564). Plants are no exception to this observation; diverse plant species possess transcription factors that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) supra; Higgins et al. (1996) *Methods Enzymol.* 266: 383-402) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

By using a phylogenetic analysis, one skilled in the art would recognize that the ability to predict similar functions conferred by closely-related polypeptides is predictable. This predictability has been confirmed by our own many studies in which we have found that a wide variety of polypeptides have orthologous or closely-related homologous sequences that function as does the first, closely-related reference sequence. For example, distinct transcription factors, including:

(i) AP2 family *Arabidopsis* G47 (found in US patent publication 20040019925A1), a phylogenetically-related sequence from soybean, and two phylogenetically-related homologs from rice all can confer greater tolerance to drought, hyperosmotic stress, or delayed flowering as compared to control plants;

(ii) CAAT family *Arabidopsis* G481 (found in PCT patent publication WO2004076638), and numerous phylogenetically-related sequences from dicots and monocots can confer greater tolerance to drought-related stress as compared to control plants;

(iii) Myb-related *Arabidopsis* G682 (found in PCT patent publication WO2004076638) and numerous phylogenetically-related sequences from dicots and monocots can confer greater tolerance to heat, drought-related stress, cold, and salt as compared to control plants;

(iv) WRKY family *Arabidopsis* G1274 (found in U.S. patent application Ser. No. 10/666,642) and numerous closely-related sequences from dicots and monocots have been shown to confer increased water deprivation tolerance, and (v) AT-hook family soy sequence G3456 (found in US patent publication 20040128712A1) and numerous phylogenetically-related sequences from dicots and monocots, increased biomass compared to control plants when these sequences are overexpressed in plants.

The polypeptides sequences belong to distinct clades of polypeptides that include members from diverse species. In each case, most or all of the clade member sequences derived from both dicots and monocots have been shown to confer darker green coloration, increased photosynthetic rate, increased size, increased yield or delayed flowering, relative to control plants, when the sequences were overexpressed. These studies each demonstrate that evolutionarily conserved genes from diverse species are likely to function similarly (i.e., by regulating similar target sequences and controlling the same traits), and that polynucleotides from one species may be transformed into closely-related or distantly-related plant species to confer or improve traits.

As shown in Table 4, polypeptides that are phylogenetically related to the polypeptides of the invention may have at least 46%, 50%, 53%, 56%, 61% or 100% amino acid sequence identity with a member of the G1435 clade of transcription factors, or have conserved GARP domains that share at least 91%, 95%, 97%, or 100% amino acid sequence identity with a member of the G1435 clade of transcription factors, and have similar functions in that the polypeptides of the invention may, when overexpressed, confer at least one regulatory activity selected from the group consisting of greater increased photosynthetic rate, increased size, increased yield or delayed flowering, relative to control plants.

At the nucleotide level, the sequences of the invention will typically share at least about 84%, 85%, 87%, 89%, 90% or 100% sequence identity to one or more of the listed full-length sequences. These percentages were determined by BLASTn analysis comparing to the G1435 polynucleotide, SEQ ID NO: 99, the clade member nucleotide sequences of:

G4241 or G4240 (SEQ ID NOs: 1991 or 1993, each 84% identical to G1435, the BLASTn analysis comparing 103/122 bases of either sequence to G1435);

G4244 (SEQ ID NO: 1987, 85% identical to G1435, the BLASTn analysis comparing 89/105 bases to G1435);

G4243 (SEQ ID NO: 1985, 87% identical to G1435, the BLASTn analysis comparing 91/104 bases to G1435);

G4245 (SEQ ID NO: 1989, 89% identical to G1435, the BLASTn analysis comparing 35/39 bases to G1435); or G2741 (SEQ ID NO: 1983, 90% identical to G1435, the BLASTn analysis comparing 172/191 bases to G1435).

The degeneracy of the genetic code enables major variations in the nucleotide sequence of a polynucleotide while maintaining the amino acid sequence of the encoded protein.

Percentage identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp (1988) *Gene* 73: 237-244. The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Software for performing BLAST analyses is publicly available, e.g., through the National Center for Biotechnology Information (see internet website at http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) *J. Mol. Biol.* 215: 403-410; Altschul (1993) *J. Mol. Evol.* 36: 290-300). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix (see Henikoff and Henikoff (1989) *Proc. Natl. Acad. Sci. USA* 89:10915). Unless otherwise indicated for comparisons of predicted polynucleotides, "sequence identity" refers to the % sequence identity generated from a tblastx using the NCBI version of the algorithm at the default settings using gapped alignments with the filter "off" (see, for example, internet website at http://www.ncbi.nlm.nih.gov/).

Other techniques for alignment are described by Doolittle, ed. (1996) *Methods in Enzymology*, vol. 266: "Computer Methods for Macromolecular Sequence Analysis" Academic Press, Inc., San Diego, Calif., USA. Preferably, an alignment program that permits gaps in the sequence is utilized to align the sequences. The Smith-Waterman is one type of algorithm that permits gaps in sequence alignments (see Shpaer (1997) *Methods Mol. Biol.* 70: 173-187). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (see, for example, Hein (1990) *Methods Enzymol.* 183: 626-645) Identity between sequences can also be determined by other methods known in the art, e.g., by varying hybridization conditions (see US Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al. (1997) *Nucleic Acids Res.* 25: 217-221), PFAM, and other databases which contain previously identified and annotated motifs, sequences and gene functions. Methods that search for primary sequence patterns with secondary structure gap penalties (Smith et al. (1992) *Protein Engineering* 5: 35-51) as well as algorithms such as Basic Local Alignment Search Tool (BLAST; Altschul (1990) supra; Altschul et al. (1993) supra), BLOCKS (Henikoff and Henikoff (1991) Nucleic Acids Res. 19: 6565-6572), Hidden Markov Models (HMM; Eddy (1996) *Curr. Opin. Str. Biol.* 6: 361-365; Sonnhammer et al. (1997) *Proteins* 28: 405-420), and the like, can be used to manipulate and analyze polynucleotide and polypeptide sequences encoded by polynucleotides. These databases, algorithms and other methods are well known in the art and are described in Ausubel et al.

(1997) Short Protocols in Molecular Biology, John Wiley & Sons, New York, N.Y., unit 7.7, and in Meyers (1995) Molecular Biology and Biotechnology, Wiley VCH, New York, N.Y., p 856-853.

A further method for identifying or confirming that specific homologous sequences control the same function is by comparison of the transcript profile(s) obtained upon overexpression or knockout of two or more related polypeptides. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler and Thomashow (2002) *Plant Cell* 14: 1675-1690), have shown that three paralogous AP2 family genes (CBF1, CBF2 and CBF3) are induced upon cold treatment, and each of which can condition improved freezing tolerance, and all have highly similar transcript profiles. Once a polypeptide has been shown to provide a specific function, its transcript profile becomes a diagnostic tool to determine whether paralogs or orthologs have the same function.

Furthermore, methods using manual alignment of sequences similar or homologous to one or more polynucleotide sequences or one or more polypeptides encoded by the polynucleotide sequences may be used to identify regions of similarity and B-box zinc finger domains. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted $\alpha$ helices, $\beta$-sheets, amphipathic helices, leucine zipper motifs, zinc finger motifs, proline-rich regions, cysteine repeat motifs, and the like.

Orthologs and paralogs of presently disclosed polypeptides may be cloned using compositions provided by the present invention according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of *Arabidopsis* polypeptide sequences and their functionally similar orthologs are listed in Table 4 and the Sequence Listing. In addition to the sequences in Table 4 and the Sequence Listing, the invention encompasses isolated nucleotide sequences that are phylogenetically and structurally similar to sequences listed in the Sequence Listing) and can function in a plant by increasing yield and/or and abiotic stress tolerance when ectopically expressed in a plant.

Since a significant number of these sequences are phylogenetically and sequentially related to each other and have been shown to increase yield from a plant and/or abiotic stress tolerance, one skilled in the art would predict that other similar, phylogenetically related sequences falling within the present clades of polypeptides would also perform similar functions when ectopically expressed.

Identifying Nucleic Acids by Hybridization

Polynucleotides homologous to the sequences illustrated in the Sequence Listing can be identified, e.g., by hybridization to each other under stringent or under highly stringent conditions. Single stranded polynucleotides hybridize when they associate based on a variety of well characterized physico-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number), as described in more detail in the references cited above.

An example of stringent hybridization conditions for hybridization of complementary nucleic acids which have more than 100 complementary residues on a filter in a Southern or northern blot is about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Nucleic acid molecules that hybridize under stringent conditions will typically hybridize to a probe based on either the entire cDNA or selected portions, e.g., to a unique subsequence, of the cDNA under wash conditions of 0.2×SSC to 2.0×SSC, 0.1% SDS at 50-65° C., for example 0.2×SSC, 0.1% SDS at 65° C. For identification of less closely related homologues washes can be performed at a lower temperature, e.g., 50° C. In general, stringency is increased by raising the wash temperature and/or decreasing the concentration of SSC.

As another example, stringent conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a transcription factor known as of the filing date of the application. Conditions can be selected such that a higher signal to noise ratio is observed in the particular assay which is used, e.g., about 15×, 25×, 35×, 50× or more. Accordingly, the subject nucleic acid hybridizes to the unique coding oligonucleotide with at least a 2× higher signal to noise ratio as compared to hybridization of the coding oligonucleotide to a nucleic acid encoding known polypeptide. Again, higher signal to noise ratios can be selected, e.g., about 5×, 10×, 25×, 35×, 50× or more. The particular signal will depend on the label used in the relevant assay, e.g., a fluorescent label, a calorimetric label, a radioactive label, or the like.

Alternatively, transcription factor homologue polypeptides can be obtained by screening an expression library using antibodies specific for one or more transcription factors. With the provision herein of the disclosed transcription factor, and transcription factor homologue nucleic acid sequences, the encoded polypeptide(s) can be expressed and purified in a heterologous expression system (e.g., *E. coli*) and used to raise antibodies (monoclonal or polyclonal) specific for the polypeptide(s) in question. Antibodies can also be raised against synthetic peptides derived from transcription factor, or transcription factor homologue, amino acid sequences.

Methods of raising antibodies are well known in the art and are described in Harlow and Lane (1988) *Antibodies: A Laboratory Manual*, Cold Spring Harbor Laboratory, New York. Such antibodies can then be used to screen an expression library produced from the plant from which it is desired to clone additional transcription factor homologues, using the methods described above. The selected cDNAs can be confirmed by sequencing and enzymatic activity.

Sequence Variations

It will readily be appreciated by those of skill in the art, that any of a variety of polynucleotide sequences are capable of encoding the transcription factors and transcription factor homologue polypeptides of the invention. Due to the degeneracy of the genetic code, many different polynucleotides can encode identical and/or substantially similar polypeptides in addition to those sequences illustrated in the Sequence Listing.

For example, Table 2 illustrates, e.g., that the codons AGC, AGT, TCA, TCC, TCG, and TCT all encode the same amino acid: serine. Accordingly, at each position in the sequence where there is a codon encoding serine, any of the above trinucleotide sequences can be used without altering the encoded polypeptide.

TABLE 2

| Amino acids | | | Codon |
|---|---|---|---|
| Alanine | Ala | A | GCA GCC GCG GCU |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGG AGT TCA TCC TCG TCT |
| Threonine | Thr | T | ACA ACC ACG ACT |
| Valine | Val | V | GTA GTC GTG GTG GTT |
| Tryptophan | Trp | W | TGG |
| Tyrosine | Tyr | Y | TAC TAT |

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence selected from the above table are a feature of the invention.

In addition to silent variations, other conservative variations that alter one, or a few amino acids in the encoded polypeptide, can be made without altering the function of the polypeptide, these conservative variants are, likewise, a feature of the invention.

For example, substitutions, deletions and insertions introduced into the sequences provided in the Sequence Listing are also envisioned by the invention. Such sequence modifications can be engineered into a sequence by site-directed mutagenesis (Wu (ed.) *Meth. Enzymol.* (1993) vol. 217, Academic Press) or the other methods noted below. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 3 when it is desired to maintain the activity of the protein. Table 3 shows amino acids which can be substituted for an amino acid in a protein and which are typically regarded as conservative substitutions.

TABLE 3

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Substitutions that are less conservative than those in Table 3 can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Further Modifying Sequences of the Invention—Mutation/Forced Evolution

In addition to generating silent or conservative substitutions as noted, above, the present invention optionally includes methods of modifying the sequences of the Sequence Listing. In the methods, nucleic acid or protein modification methods are used to alter the given sequences to produce new sequences and/or to chemically or enzymatically modify given sequences to change the properties of the nucleic acids or proteins.

Thus, in one embodiment, given nucleic acid sequences are modified, e.g., according to standard mutagenesis or artificial evolution methods to produce modified sequences. For example, Ausubel, supra, provides additional details on mutagenesis methods. Artificial forced evolution methods are described, e.g., by Stemmer (1994) *Nature* 370:389-391, and Stemmer (1994) *Proc. Natl. Acad. Sci. USA* 91:10747-10751. Many other mutation and evolution methods are also available and expected to be within the skill of the practitioner.

Similarly, chemical or enzymatic alteration of expressed nucleic acids and polypeptides can be performed by standard methods. For example, sequence can be modified by addition of lipids, sugars, peptides, organic or inorganic compounds, by the inclusion of modified nucleotides or amino acids, or the like. For example, protein modification techniques are illustrated in Ausubel, supra. Further details on chemical and enzymatic modifications can be found herein. These modification methods can be used to modify any given sequence, or to modify any sequence produced by the various mutation and artificial evolution modification methods noted herein.

Accordingly, the invention provides for modification of any given nucleic acid by mutation, evolution, chemical or enzymatic modification, or other available methods, as well as for the products produced by practicing such methods, e.g., using the sequences herein as a starting substrate for the various modification approaches.

For example, optimized coding sequence containing codons preferred by a particular prokaryotic or eukaryotic host can be used e.g., to increase the rate of translation or to produce recombinant RNA transcripts having desirable properties, such as a longer half-life, as compared with transcripts produced using a non-optimized sequence. Translation stop codons can also be modified to reflect host preference. For example, preferred stop codons for *S. cerevisiae* and mammals are TAA and TGA, respectively. The preferred stop codon for monocotyledonous plants is TGA, whereas insects and *E. coli* prefer to use TAA as the stop codon.

The polynucleotide sequences of the present invention can also be engineered in order to alter a coding sequence for a variety of reasons, including but not limited to, alterations which modify the sequence to facilitate cloning, processing and/or expression of the gene product. For example, alterations are optionally introduced using techniques which are well known in the art, e.g., site-directed mutagenesis, to insert new restriction sites, to alter glycosylation patterns, to change codon preference, to introduce splice sites, etc.

Furthermore, a fragment or domain derived from any of the polypeptides of the invention can be combined with domains derived from other transcription factors or synthetic domains to modify the biological activity of a transcription factor. For instance, a DNA binding domain derived from a transcription factor of the invention can be combined with the activation domain of another transcription factor or with a synthetic activation domain. A transcription activation domain assists in initiating transcription from a DNA binding site. Examples include the transcription activation region of VP16 or GAL4 (Moore et al. (1998) *Proc. Natl. Acad. Sci. USA* 95: 376-381; and Aoyama et al. (1995) *Plant Cell* 7:1773-1785), peptides derived from bacterial sequences (Ma and Ptashne (1987) *Cell* 51; 113-119) and synthetic peptides (Giniger and Ptashne, (1987) *Nature* 330:670-672).

Expression and Modification of Polypeptides

Typically, polynucleotide sequences of the invention are incorporated into recombinant DNA (or RNA) molecules that direct expression of polypeptides of the invention in appropriate host cells, transgenic plants, in vitro translation systems, or the like. Due to the inherent degeneracy of the genetic code, nucleic acid sequences which encode substantially the same or a functionally equivalent amino acid sequence can be substituted for any listed sequence to provide for cloning and expressing the relevant homologue.

Vectors, Promoters and Expression Systems

The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts which describe molecular biological techniques useful herein, including the use and production of vectors, promoters and many other relevant topics, include Berger, Sambrook and Ausubel, supra. Any of the identified sequences can be incorporated into a cassette or vector, e.g., for expression in plants. A number of expression vectors suitable for stable transformation of plant cells or for the establishment of transgenic plants have been described including those described in Weissbach and Weissbach, (1989) *Methods for Plant Molecular Biology*, Academic Press, and Gelvin et al., (1990) *Plant Molecular Biology Manual*, Kluwer Academic Publishers. Specific examples include those derived from a Ti plasmid of *Agrobacterium tumefaciens*, as well as those disclosed by Herrera-Estrella et al. (1983) *Nature* 303: 209, Bevan (1984) *Nucl Acid Res.* 12: 8711-8721, Klee (1985) *Bio/Technol.* 3: 637-642, for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) *Bio/Technol.* 9: 957-962) and corn (Gordon-Kamm (1990) *Plant Cell* 2: 603-618) can be produced. An immature embryo can also be a good target tissue for monocots for direct DNA delivery techniques by using the particle gun (Weeks et al. (1993) *Plant Physiol.* 102: 1077-1084; Vasil (1993) *Bio/Technol.* 10: 667-674; Wan and Lemeaux (1994) *Plant Physiol.* 104: 37-48, and for *Agrobacterium*-mediated DNA transfer (Ishida et al. (1996) *Nature Biotech.* 14: 745-750).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally- or developmentally-regulated, or cell- or tissue-specific expression), a transcription initiation start site, an RNA processing signal (such as intron splice sites), a transcription termination site, and/or a polyadenylation signal.

Examples of constitutive plant promoters which can be useful for expressing the TF sequence include: the cauliflower mosaic virus (CaMV) 35S promoter, which confers constitutive, high-level expression in most plant tissues (see, e.g., Odel et al. (1985) *Nature* 313:810); the nopaline synthase promoter (An et al. (1988) *Plant Physiol.* 88:547); and the octopine synthase promoter (Fromm et al. (1989) *Plant Cell* 1: 977).

A variety of plant gene promoters that regulate gene expression in response to environmental, hormonal, chemical, developmental signals, and in a tissue-active manner can be used for expression of a TF sequence in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorable be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697), fruit-specific promoters that are active during fruit ripening (such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol Biol.* 11:651), root-specific promoters, such as those disclosed in U.S. Pat. Nos. 5,618,988, 5,837,848 and 5,905,186, pollen-active promoters such as PTA29, PTA26 and PTA13 (U.S. Pat. No. 5,792,929), promoters active in vascular tissue (Ringli and Keller (1998) *Plant Mol. Biol.* 37:977-988), flower-specific (Kaiser et al, (1995) *Plant Mol. Biol.* 28:231-243), pollen (Baerson et al. (1994) *Plant Mol. Biol.* 26:1947-1959), carpels (Ohl et al. (1990) *Plant Cell* 2:837-848), pollen and ovules (Baerson et al. (1993) *Plant Mol. Biol.* 22:255-267), auxin-inducible promoters (such as that described in van der Kop et al. (1999) *Plant Mol. Biol.* 39:979-990 or Baumann et al. (1999) *Plant Cell* 11:323-334), cytokinin-inducible promoter (Guevara-Garcia (1998) *Plant Mol. Biol.* 38:743-753), promoters responsive to gibberellin (Shi et al. (1998) *Plant Mol. Biol.* 38:1053-1060, Willmott et al. (1998) 38:817-825) and the like. Additional promoters are those that elicit expression in response to heat (Ainley et al. (1993) *Plant Mol. Biol.* 22: 13-23), light (e.g., the pea rbcS-3A promoter, Kuhlemeier et al. (1989) *Plant Cell* 1:471, and the maize rbcS promoter, Schaffner and Sheen (1991) *Plant Cell* 3: 997); wounding (e.g., wunI, Siebertz et al. (1989) *Plant Cell* 1: 961); pathogens (such as the PR-1 promoter described in Buchel et al. (1999) *Plant Mol. Biol.* 40:387-396, and the PDF1.2 promoter described in Manners et al. (1998) *Plant Mol. Biol.* 38:1071-80), and chemicals such as methyl jasmonate or salicylic acid (Gatz et al. (1997) *Plant Mol. Biol.* 48: 89-108). In addition, the timing of the expression can be controlled by using promoters such as those acting at senescence (An and Amazon (1995) *Science* 270: 1986-1988); or late seed development (Odell et al. (1994) *Plant Physiol.* 106:447-458).

Plant expression vectors can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Additional Expression Elements

Specific initiation signals can aid in efficient translation of coding sequences. These signals can include, e.g., the ATG initiation codon and adjacent sequences. In cases where a coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous transcriptional control signals including the ATG initiation codon can be separately provided. The initiation codon is provided in the correct reading frame to facilitate transcription. Exogenous transcriptional elements and initiation codons can be of various origins, both natural and synthetic. The efficiency of expression can be enhanced by the inclusion of enhancers appropriate to the cell system in use.

Expression Hosts

The present invention also relates to host cells which are transduced with vectors of the invention, and the production of polypeptides of the invention (including fragments thereof) by recombinant techniques. Host cells are genetically engineered (i.e, nucleic acids are introduced, e.g., transduced, transformed or transfected) with the vectors of this invention, which may be, for example, a cloning vector or an expression vector comprising the relevant nucleic acids herein. The vector is optionally a plasmid, a viral particle, a phage, a naked nucleic acids, etc. The engineered host cells can be cultured in conventional nutrient media modified as appropriate for activating promoters, selecting transformants, or amplifying the relevant gene. The culture conditions, such as temperature, pH and the like, are those previously used with the host cell selected for expression, and will be apparent to those skilled in the art and in the references cited herein, including, Sambrook and Ausubel.

The host cell can be a eukaryotic cell, such as a yeast cell, or a plant cell, or the host cell can be a prokaryotic cell, such as a bacterial cell. Plant protoplasts are also suitable for some applications. For example, the DNA fragments are introduced into plant tissues, cultured plant cells or plant protoplasts by standard methods including electroporation (Fromm et al., (1985) *Proc. Natl. Acad. Sci. USA* 82, 5824, infection by viral vectors such as cauliflower mosaic virus (CaMV) (Hohn et al., (1982) *Molecular Biology of Plant Tumors*, (Academic Press, New York) pp. 549-560; U.S. Pat. No. 4,407,956), high velocity ballistic penetration by small particles with the nucleic acid either within the matrix of small beads or particles, or on the surface (Klein et al., (1987) *Nature* 327, 70-73), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233:496-498; Fraley et al. (1983) *Proc. Natl. Acad. Sci. USA* 80, 4803).

The cell can include a nucleic acid of the invention which encodes a polypeptide, wherein the cells expresses a polypeptide of the invention. The cell can also include vector sequences, or the like. Furthermore, cells and transgenic plants which include any polypeptide or nucleic acid above or throughout this specification, e.g., produced by transduction of a vector of the invention, are an additional feature of the invention.

For long-term, high-yield production of recombinant proteins, stable expression can be used. Host cells transformed with a nucleotide sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature proteins of the invention can be designed with signal sequences which direct secretion of the mature polypeptides through a prokaryotic or eukaryotic cell membrane.

Modified Amino Acids

Polypeptides of the invention may contain one or more modified amino acids. The presence of modified amino acids may be advantageous in, for example, increasing polypeptide half-life, reducing polypeptide antigenicity or toxicity, increasing polypeptide storage stability, or the like. Amino acid(s) are modified, for example, co-translationally or post-translationally during recombinant production or modified by synthetic or chemical means.

Non-limiting examples of a modified amino acid include incorporation or other use of acetylated amino acids, glycosylated amino acids, sulfated amino acids, prenylated (e.g., farnesylated, geranylgeranylated) amino acids, PEG modified (e.g., "PEGylated") amino acids, biotinylated amino acids, carboxylated amino acids, phosphorylated amino acids, etc. References adequate to guide one of skill in the modification of amino acids are replete throughout the literature.

Identification of Additional Factors

A transcription factor provided by the present invention can also be used to identify additional endogenous or exogenous molecules that can affect a phenotype or trait of interest. On the one hand, such molecules include organic (small or large molecules) and/or inorganic compounds that affect expression of (i.e., regulate) a particular transcription factor. Alternatively, such molecules include endogenous molecules that are acted upon either at a transcriptional level by a transcription factor of the invention to modify a phenotype as desired. For example, the transcription factors can be employed to identify one or more downstream gene with which is subject to a regulatory effect of the transcription factor. In one approach, a transcription factor or transcription factor homologue of the invention is expressed in a host cell, e.g, a transgenic plant cell, tissue or explant, and expression products, either RNA or protein, of likely or random targets are monitored, e.g., by hybridization to a microarray of nucleic acid probes corresponding to genes expressed in a tissue or cell type of interest, by two-dimensional gel electrophoresis of protein products, or by any other method known in the art for assessing expression of gene products at the level of RNA or protein. Alternatively, a transcription factor of the invention can be used to identify promoter sequences (i.e., binding sites) involved in the regulation of a downstream target. After identifying a promoter sequence, interactions between the transcription factor and the promoter sequence can be modified by changing specific nucleotides in the promoter sequence or specific amino acids in the transcription factor that interact with the promoter sequence to alter a plant trait. Typically, transcription factor DNA binding sites are identified by gel shift assays. After identifying the promoter regions, the promoter region sequences can be employed in double-stranded DNA arrays to identify molecules that affect the interactions of the transcription factors with their promoters (Bulyk et al. (1999) *Nature Biotechnol.* 17:573-577).

The identified transcription factors are also useful to identify proteins that modify the activity of the transcription factor. Such modification can occur by covalent modification, such as by phosphorylation, or by protein-protein (homo or -heteropolymer) interactions. Any method suitable for detecting protein-protein interactions can be employed. Among the methods that can be employed are co-immunoprecipitation, cross-linking and co-purification through gradients or chromatographic columns, and the two-hybrid yeast system.

The two-hybrid system detects protein interactions in vivo and is described in Chien, et al., (1991), *Proc. Natl. Acad. Sci. USA* 88, 9578-9582 and is commercially available from Clontech (Palo Alto, Calif.). In such a system, plasmids are constructed that encode two hybrid proteins: one consists of the DNA-binding domain of a transcription activator protein fused to the TF polypeptide and the other consists of the transcription activator protein's activation domain fused to an unknown protein that is encoded by a cDNA that has been recombined into the plasmid as part of a cDNA library. The DNA-binding domain fusion plasmid and the cDNA library are transformed into a strain of the yeast *Saccharomyces cerevisiae* that contains a reporter gene (e.g., lacZ) whose regulatory region contains the transcription activator's binding site. Either hybrid protein alone cannot activate transcription of the reporter gene. Interaction of the two hybrid proteins reconstitutes the functional activator protein and results in expression of the reporter gene, which is detected by an assay for the reporter gene product. Then, the library plasmids responsible for reporter gene expression are isolated and sequenced to identify the proteins encoded by the library plasmids. After identifying proteins that interact with the transcription factors, assays for compounds that interfere with the TF protein-protein interactions can be preformed.

Identification of Modulators

In addition to the intracellular molecules described above, extracellular molecules that alter activity or expression of a transcription factor, either directly or indirectly, can be identified. For example, the methods can entail first placing a candidate molecule in contact with a plant or plant cell. The molecule can be introduced by topical administration, such as spraying or soaking of a plant, and then the molecule's effect on the expression or activity of the TF polypeptide or the expression of the polynucleotide monitored. Changes in the expression of the TF polypeptide can be monitored by use of polyclonal or monoclonal antibodies, gel electrophoresis or the like. Changes in the expression of the corresponding polynucleotide sequence can be detected by use of microarrays, Northern blots, quantitative PCR, or any other technique for monitoring changes in mRNA expression. These techniques are exemplified in Ausubel et al. (eds) *Current Protocols in Molecular Biology*, John Wiley & Sons (1998). Such changes in the expression levels can be correlated with modified plant traits and thus identified molecules can be useful for soaking or spraying on fruit, vegetable and grain crops to modify traits in plants.

Essentially any available composition can be tested for modulatory activity of expression or activity of any nucleic acid or polypeptide herein. Thus, available libraries of compounds such as chemicals, polypeptides, nucleic acids and the like can be tested for modulatory activity. Often, potential modulator compounds can be dissolved in aqueous or organic (e.g., DMSO-based) solutions for easy delivery to the cell or plant of interest in which the activity of the modulator is to be tested. Optionally, the assays are designed to screen large modulator composition libraries by automating the assay steps and providing compounds from any convenient source to assays, which are typically run in parallel (e.g., in microtiter formats on microtiter plates in robotic assays).

In one embodiment, high throughput screening methods involve providing a combinatorial library containing a large number of potential compounds (potential modulator compounds). Such "combinatorial chemical libraries" are then screened in one or more assays, as described herein, to identify those library members (particular chemical species or subclasses) that display a desired characteristic activity. The compounds thus identified can serve as target compounds.

A combinatorial chemical library can be, e.g., a collection of diverse chemical compounds generated by chemical synthesis or biological synthesis. For example, a combinatorial chemical library such as a polypeptide library is formed by combining a set of chemical building blocks (e.g., in one example, amino acids) in every possible way for a given compound length (i.e., the number of amino acids in a polypeptide compound of a set length). Exemplary libraries include peptide libraries, nucleic acid libraries, antibody libraries (see, e.g., Vaughn et al. (1996) *Nature Biotechnol.* 14:309-314 and PCT/US96/10287), carbohydrate libraries (see, e.g., Liang et al. *Science* (1996) 274:1520-1522 and U.S. Pat. No. 5,593,853), peptide nucleic acid libraries (see, e.g., U.S. Pat. No. 5,539,083), and small organic molecule libraries (see, e.g., benzodiazepines, Baum (1993) *Chem Eng. News* January 18, page 33; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337) and the like.

Preparation and screening of combinatorial or other libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.* 37:487-493 and Houghton et al. *Nature* (1991) 354:84-88). Other chemistries for generating chemical diversity libraries can also be used.

In addition, as noted, compound screening equipment for high-throughput screening is generally available, e.g., using any of a number of well known robotic systems that have also been developed for solution phase chemistries useful in assay systems. These systems include automated workstations including an automated synthesis apparatus and robotic systems utilizing robotic arms. Any of the above devices are suitable for use with the present invention, e.g., for high-throughput screening of potential modulators. The nature and implementation of modifications to these devices (if any) so that they can operate as discussed herein will be apparent to persons skilled in the relevant art.

Indeed, entire high throughput screening systems are commercially available. These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. Similarly, microfluidic implementations of screening are also commercially available.

The manufacturers of such systems provide detailed protocols the various high throughput. Thus, for example, Zymark Corp. provides technical bulletins describing screening systems for detecting the modulation of gene transcription, ligand binding, and the like. The integrated systems herein, in addition to providing for sequence alignment and, optionally, synthesis of relevant nucleic acids, can include such screening apparatus to identify modulators that have an effect on one or more polynucleotides or polypeptides according to the present invention.

In some assays it is desirable to have positive controls to ensure that the components of the assays are working properly. At least two types of positive controls are appropriate. That is, known transcriptional activators or inhibitors can be incubated with cells/plants/etc. in one sample of the assay, and the resulting increase/decrease in transcription can be detected by measuring the resulting increase in RNA/protein expression, etc., according to the methods herein. It will be appreciated that modulators can also be combined with transcriptional activators or inhibitors to find modulators which inhibit transcriptional activation or transcriptional repression. Either expression of the nucleic acids and proteins herein or any additional nucleic acids or proteins activated by the nucleic acids or proteins herein, or both, can be monitored.

In an embodiment, the invention provides a method for identifying compositions that modulate the activity or expression of a polynucleotide or polypeptide of the invention. For example, a test compound, whether a small or large molecule, is placed in contact with a cell, plant (or plant tissue or explant), or composition comprising the polynucleotide or polypeptide of interest and a resulting effect on the cell, plant, (or tissue or explant) or composition is evaluated by monitoring, either directly or indirectly, one or more of: expression level of the polynucleotide or polypeptide, activity (or modulation of the activity) of the polynucleotide or polypeptide. In some cases, an alteration in a plant phenotype can be detected following contact of a plant (or plant cell, or tissue or explant) with the putative modulator, e.g., by modulation of expression or activity of a polynucleotide or polypeptide of the invention.

Subsequences

Also contemplated are uses of polynucleotides, also referred to herein as oligonucleotides, typically having at least 12 bases, preferably at least 15, more preferably at least 20, 30, or 50 bases, which hybridize under at least highly stringent (or ultra-high stringent or ultra-ultra-high stringent conditions) conditions to a polynucleotide sequence described above. The polynucleotides may be used as probes, primers, sense and antisense agents, and the like, according to methods as noted supra.

Subsequences of the polynucleotides of the invention, including polynucleotide fragments and oligonucleotides are useful as nucleic acid probes and primers. An oligonucleotide suitable for use as a probe or primer is at least about 15 nucleotides in length, more often at least about 18 nucleotides, often at least about 21 nucleotides, frequently at least about 30 nucleotides, or about 40 nucleotides, or more in length. A nucleic acid probe is useful in hybridization protocols, e.g., to identify additional polypeptide homologues of the invention, including protocols for microarray experiments. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods. See Sambrook and Ausubel, supra.

In addition, the invention includes an isolated or recombinant polypeptide including a subsequence of at least about 15 contiguous amino acids encoded by the recombinant or isolated polynucleotides of the invention. For example, such polypeptides, or domains or fragments thereof, can be used as immunogens, e.g., to produce antibodies specific for the polypeptide sequence, or as probes for detecting a sequence of interest. A subsequence can range in size from about 15 amino acids in length up to and including the full length of the polypeptide.

Introduction to the GARP Family

The acronym GARP was adopted to describe this family of transcription factors based on three of the founding members of the family: maize GOLDEN2, the ARR B class of *Arabidopsis* response regulator homologs, and Psr1 of *Chlamydomonas reinhardtii* (Riechmann et al. (2000) *Science* 290: 2105-2110). These proteins share a putative DNA binding domain with limited homology to the myb superfamily of transcription factors (Sakai et al. (1998) *Plant Cell Physiol.* 39: 1232-1239), particularly to a family of Myb-related proteins that includes the circadian regulatory protein CCA1 (Riechmann et al. 2000) supra). Distant homology of this domain is also evident to the TEA DNA binding domain found in a number of regulatory genes from fungi, insects, and mammals (Burglin (1991) *Cell* 66: 11-12; Hall et al. (1998) *Plant Cell* 10: 925-36). The TEA domain is predicted to form two α helices that are implicated in DNA binding (Burglin (1991) supra). For simplicity, this putative DNA binding domain is referred to as the GARP domain. The GARP domain is a highly conserved stretch of 49-50 amino acids that begins with an invariant tryptophan residue and ends in a motif with the consensus sequence SHLQKYRL (SEQ ID NO: 2008), in which the first four amino acids appear to be invariant.

The founding member of the GARP family is the maize GOLDEN2 (G2) gene (Hall et al. (1998) supra). Maize uses the C4 pathway of photosynthesis, where photosynthetic carbon fixation reactions are segregated between the mesophyll and bundle sheath cells. The g2 mutation perturbs the specialized development of the bundle sheath cells and expression of the C4 photosynthetic pathway enzymes. Evidence provided by G2-GUS fusions indicates that G2 is localized to the nucleus. The GARP domain was subsequently found in a *Chlamydomonas reinhardtii* protein, PSR1, that is a nuclear-localized regulator of phosphorus metabolism (Wykoff et al. (1999) *Proc. Natl. Acad. Sci. USA* 96: 15336-15341) as well as in a tobacco protein submitted to GenBank as a transfactor, WREBP-1 (acc. no. AB017693).

Fifty-six GARP genes are present in *Arabidopsis*, and these fall into two major classes. The first class consists of proteins that contain the GARP domain as the only recognizable motif (44 genes). G2, PSR1, and WREBP-1 are of this type. The second class also contains an N terminal domain with similarity to bacterial response regulators (12 genes). These proteins have been termed ARR for *Arabidopsis* Response Regulator (Sakai et al. (1998) supra), or ARP for *Arabidopsis* Receiver-like Protein (acc. no. AJ005194).

The response regulator class of GARP proteins is of particular interest because of the growing evidence that phosphorelay signal transduction systems, with homology to prokaryotic two-component systems, are functional in plants. The simplest bacterial two-component systems consist of a sensor kinase and a response regulator protein. The sensor kinase autophosphorylates on a histidine residue, and the rate of autophosphorylation is modified by input from a sensor domain. The phosphate group is then transferred to an aspartate residue on the response regulator. In prokaryotes the response regulator is usually a transcription factor that activates downstream responses, although some response regulators have different modes of action. Phosphorelay systems of greater complexity are known, where the phosphate is passed through one or more intermediary phosphotransmitter proteins before phosphorylation of the response regulator. Other variations include proteins with fused sensor kinase and receiver domains (hybrid kinases), and the *Arabidopsis* ETR1 protein is a eukaryotic example of this class (for reviews see D'Agostino and Kieber (1999) *Trends Biochem Sci.* 24: 452-456); Chang and Stewart (1998) *Plant Physiol.* 117: 723-731). The response regulator class of GARP proteins is a subset of a group of putative *Arabidopsis* response regulators that has been termed the type-B response regulators. The type-A response regulators in contrast lack a putative DNA binding domain (D'Agostino and Kieber (1999) supra). The type-B response regulators are likely to be the functional equivalents of bacterial response regulators, which receive a signal from a sensor kinase and activate transcription. ARR type-B proteins have been shown to bind DNA (Sakai et al. (2000) *Plant J.* 24: 703-711; Lohrmann et al. (2001) *Mol. Genet. Genomics* 265: 2-13), and to interact with histidine phosphotransmitter proteins (Imamura et al. (1999) *Plant Cell Physiol.* 40: 733-742).

Recent work implicates the response regulator GARP (ARR type-B) proteins in cytokinin signal transduction. ARR1, ARR2, and ARR10 activate transcription of the cytokinin-regulated type-A ARR gene ARR6 in protoplasts (Hwang and Sheen (2001) *Nature* 413: 383-389). The cytokinin receptor CRE1 was recently found to be a histidine kinase with fused receiver domains (Inoue et al. (2001) *Nature* 409: 1060-1063). A signal transduction pathway is postulated where CRE1 initiates a phosphorelay, the signal is transduced to the nucleus through histidine phosphotransmitter proteins, and these proteins interact with ARR type-B proteins to release these proteins from putative repressors, allowing them to activate transcription. Among the genes induced are those encoding ARR type-A proteins, which are thought to serve as negative feedback regulators of the pathway (Hwang and Sheen (2001) supra).

It should be noted that one *Arabidopsis* protein with a GARP domain, AT1, was identified in a screen for clones affecting cell shape when overexpressed in *Schizosaccharomyces pombe*. Overexpression of AT1 caused disordered actin staining and cell elongation similar to the effects of overexpressing cytoskeletal components. On the basis of these results, AT1 was characterized as a putative cytoskeletal protein, and annotated as such in GenBank (Xia et al, (1996) *Plant J.* 10:761-769). However, the effects that AT1 overexpression produced could also be due to inappropriate activation of "*S. pombe*" genes. Because AT1 was the only annotated protein with a GARP domain in the database for some time, a number of *Arabidopsis* proteins with GARP domains were annotated as putative cytoskeletal proteins, even though the annotation of AT1 is tenuous.

G1435, SEQ ID NO: 1796, encoded by SEQ ID NO: 99, is an example of a GARP family transcription factor polypeptide. A number of sequences have been found in other plant species that are closely-related to G1435. Table 4 shows a number of polypeptides of the invention and includes the SEQ ID NO: (Column 1), the species from which the sequence was derived and the Gene Identifier ("GID"; Column 2), the percent identity of the polypeptide in Column 1 to the full length G1435 polypeptide, SEQ ID NO: 1, as determined by a BLASTp analysis with a wordlength (W) of 3, an expectation (E) of 10, and the BLOSUM62 scoring matrix Henikoff & Henikoff (1989) *Proc. Natl. Acad. Sci. USA* 89:10915; Column 3), the amino acid residue coordinates for the respective conserved GARP domains, in amino acid coordinates beginning at the n-terminus, of each of the sequences (Column 4), the conserved GARP domain sequences of the respective polypeptides (Column 5); the SEQ ID NO: of each of the GARP domains (Column 6), and the percentage identity of the conserved GARP domain in Column 5 to the conserved GARP domain, SEQ ID NO: 1995, in the *Arabidopsis* G1435 sequence, SEQ ID NO: 1796 (Column 7; determined by BLASTp analysis as indicated above).

TABLE 4

Conserved domains and potentially valuable morphological traits of G1435 and closely related sequences

| Column 1 Polypeptide SEQ ID NO: | Column 2 Species/ GID No. | Column 3 Percent identity of polypeptide in Column 1 to G1435 (identical residues/ total number of residues compared) | Column 4 GARP domain in amino acid coordinates | Column 5 Conserved GARP domain | Column 6 SEQ ID NO: of GARP domain | Column 7 Percent identity of conserved domain in Column 5 to conserved domain of G1435 |
|---|---|---|---|---|---|---|
| 1796 | At/G1435 | 100% (298/298) | 146-194 | WTPQLHKRFVDVVAH LGIKNAVPKTIMQLM NVEGLTRENVASHLQ KYRL | 1995 | 100% (49/49) |
| 1984 | At/G2741 | 61% (205/331) | 149-197 | WTPQLHKRFVDVVAH LGIKNAVPKTIMQLM NVEGLTRENVASHLQ KYRL | 1996 | 100% (49/49) |
| 1986 | Gm/G4243 | 53% (147/274) | 148-196 | WTPQLHKRFVDVVAH LGIKNAVPKTIMQLM NVEGLTRENVASHLQ KYRL | 1997 | 100% (49/49) |
| 1988 | Gm/G4244 | 56% (141/250) | 149-197 | WTPQLHKRFVDVVAH LGIKNAVPKTIMQLM NVEGLTRENVASHLQ KYRL | 1998 | 100% (49/49) |
| 1994 | Zm/G4240 | 50% (130/257) | 141-189 | WTPQLHKRFVDVVAH LGMKNAVPKTIMQLM NVEGLTRENVASHLQ KYRL | 2001 | 97% (47/49) |
| 1992 | Os/G4241 | 56% (119/212) | 123-171 | WTPQLHKRFVEVVAH LGMKNAVPKTIMQLM NVEGLTRENVASHLQ KYRL | 2000 | 95% (47/49) |
| 1990 | Le/G4245 | 46% (146/317) | 155-203 | WTPQLHKRFIEVVAH LGIKGAVPKTIMQLM NVEGLTRENVAGHLQ KYRL | 1999 | 91% (45/49) |

Species abbreviations for Table 4: At - *Arabidopsis thaliana*; Gm - *Glycine max*; Le - *Lycopersicon esculentum*; Os - *Oryza sativa*; Zm - *Zea mays*.

Production of Transgenic Plants

Modification of Traits

The polynucleotides of the invention are favorably employed to produce transgenic plants with various traits, or characteristics, that have been modified in a desirable manner, e.g., to improve the seed characteristics of a plant. For example, alteration of expression levels or patterns (e.g., spatial or temporal expression patterns) of one or more of the transcription factors (or transcription factor homologues) of the invention, as compared with the levels of the same protein found in a control or a wild type plant, can be used to modify a plant's traits. An illustrative example of trait modification, improved characteristics, by altering expression levels of a particular transcription factor is described further in the Examples and the Sequence Listing.

Antisense and Cosuppression Approaches

In addition to expression of the nucleic acids of the invention as gene replacement or plant phenotype modification nucleic acids, the nucleic acids are also useful for sense and anti-sense suppression of expression, e.g., to down-regulate expression of a nucleic acid of the invention, e.g., as a further mechanism for modulating plant phenotype. That is, the nucleic acids of the invention, or subsequences or anti-sense sequences thereof, can be used to block expression of naturally occurring homologous nucleic acids. A variety of sense and anti-sense technologies are known in the art, e.g., as set forth in Lichtenstein and Nellen (1997) *Antisense Technology: A Practical Approach* IRL Press at Oxford University, Oxford, England. In general, sense or anti-sense sequences are introduced into a cell, where they are optionally amplified, e.g., by transcription. Such sequences include both simple oligonucleotide sequences and catalytic sequences such as ribozymes.

For example, a reduction or elimination of expression (i.e., a "knock-out") of a transcription factor or transcription factor homologue polypeptide in a transgenic plant, e.g., to modify a plant trait, can be obtained by introducing an antisense construct corresponding to the polypeptide of interest as a cDNA. For antisense suppression, the transcription factor or homologue cDNA is arranged in reverse orientation (with respect to the coding sequence) relative to the promoter sequence in the expression vector. The introduced sequence need not be the full length cDNA or gene, and need not be identical to the cDNA or gene found in the plant type to be transformed. Typically, the antisense sequence need only be capable of hybridizing to the target gene or RNA of interest. Thus, where the introduced sequence is of shorter length, a higher degree of homology to the endogenous transcription factor sequence will be needed for effective antisense suppression. While antisense sequences of various lengths can be utilized, preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous transcription factor gene in the plant cell.

Suppression of endogenous transcription factor gene expression can also be achieved using a ribozyme. Ribozymes are RNA molecules that possess highly specific endoribonuclease activity. The production and use of ribozymes are disclosed in U.S. Pat. No. 4,987,071 and U.S. Pat. No. 5,543,508. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

Vectors in which RNA encoded by a transcription factor or transcription factor homologue cDNA is over-expressed can also be used to obtain co-suppression of a corresponding endogenous gene, e.g., in the manner described in U.S. Pat. No. 5,231,020 to Jorgensen. Such co-suppression (also termed sense suppression) does not require that the entire transcription factor cDNA be introduced into the plant cells, nor does it require that the introduced sequence be exactly identical to the endogenous transcription factor gene of interest. However, as with antisense suppression, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of the transcription factor mRNA, e.g., sequences comprising one or more stop codon, or nonsense mutation) can also be used to suppress expression of an endogenous transcription factor, thereby reducing or eliminating it's activity and modifying one or more traits. Methods for producing such constructs are described in U.S. Pat. No. 5,583,021. Preferably, such constructs are made by introducing a premature stop codon into the transcription factor gene. Alternatively, a plant trait can be modified by gene silencing using double-strand RNA (Sharp (1999) *Genes Dev.* 13: 139-141).

Another method for abolishing the expression of a gene is by insertion mutagenesis using the T-DNA of *Agrobacterium tumefaciens*. After generating the insertion mutants, the mutants can be screened to identify those containing the insertion in a transcription factor or transcription factor homologue gene. Plants containing a single transgene insertion event at the desired gene can be crossed to generate homozygous plants for the mutation (Koncz et al. (1992) *Methods in Arabidopsis Research*, World Scientific).

Alternatively, a plant phenotype can be altered by eliminating an endogenous gene, such as a transcription factor or transcription factor homologue, e.g., by homologous recombination (Kempin et al. (1997) *Nature* 389:802).

A plant trait can also be modified by using the cre-lox system (for example, as described in U.S. Pat. No. 5,658, 772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means. For example, by ectopically expressing a gene by T-DNA activation tagging (Ichikawa et al. (1997) *Nature* 390 698-701; Kakimoto et al. (1996) *Science* 274: 982-985). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (See, e.g., PCT Publications WO 96/06166 and WO 98/53057 which describe the modification of the DNA binding specificity of zinc finger proteins by changing particular amino acids in the DNA binding motif).

The transgenic plant can also include the machinery necessary for expressing or altering the activity of a polypeptide encoded by an endogenous gene, for example by altering the phosphorylation state of the polypeptide to maintain it in an activated state.

Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a transcription factor or transcription factor homologue, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledonous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al. (1984) *Handbook of Plant Cell Culture— Crop Species*. Macmillan Publ. Co. Shimamoto et al. (1989) *Nature* 338:274-276; Fromm et al. (1990) *Bio/Technology* 8:833-839; and Vasil et al. (1990) *Bio/Technology* 8:429-434.

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence in a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Integrated Systems—Sequence Identity

Additionally, the present invention may be an integrated system, computer or computer readable medium that comprises an instruction set for determining the identity of one or more sequences in a database. In addition, the instruction set can be used to generate or identify sequences that meet any specified criteria. Furthermore, the instruction set may be used to associate or link certain functional benefits, such improved characteristics, with one or more identified sequence.

For example, the instruction set can include, e.g., a sequence comparison or other alignment program, e.g., an available program such as, for example, the Wisconsin Package Version 10.0, such as BLAST, FASTA, PILEUP, FINDPATTERNS or the like (GCG, Madison, Wis.). Public sequence databases such as GenBank, EMBL, Swiss-Prot and PIR or private sequence databases such as PhytoSeq (Incyte Pharmaceuticals, Palo Alto, Calif.) can be searched.

Alignment of sequences for comparison can be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. U.S.A.* 85: 2444, by computerized implementations of these algorithms. After alignment, sequence comparisons between two (or more) polynucleotides or polypeptides are typically performed by comparing sequences of the two sequences over a comparison window to identify and compare local regions of sequence similarity. The comparison window can be a segment of at least about 20 contiguous positions, usually about 50 to about 200, more usually about 100 to about 150 contiguous positions. A description of the method is provided in Ausubel et al., supra.

A variety of methods of determining sequence relationships can be used, including manual alignment and computer assisted sequence alignment and analysis. This later approach is a preferred approach in the present invention, due to the increased throughput afforded by computer assisted methods. As noted above, a variety of computer programs for performing sequence alignment are available, or can be produced by one of skill.

One example algorithm that is suitable for determining percent sequence identity and sequence similarity is the BLAST algorithm, which is described in Altschul et al. *J. Mol. Biol.* 215:403-410 (1990). Software for performing BLAST analyses is publicly available, e.g., through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) supra).

In addition to calculating percent sequence identity, the BLAST algorithm also performs a statistical analysis of the similarity between two sequences (see, e.g., Karlin & Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001. An additional example of a useful sequence alignment algorithm is PILEUP. PILEUP creates a multiple sequence alignment from a group of related sequences using progressive, pairwise alignments. The program can align, e.g., up to 300 sequences of a maximum length of 5,000 letters.

The integrated system, or computer typically includes a user input interface allowing a user to selectively view one or more sequence records corresponding to the one or more character strings, as well as an instruction set which aligns the one or more character strings with each other or with an additional character string to identify one or more region of sequence similarity. The system may include a link of one or more character strings with a particular phenotype or gene function. Typically, the system includes a user readable output element which displays an alignment produced by the alignment instruction set.

The methods of this invention can be implemented in a localized or distributed computing environment. In a distributed environment, the methods may implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an intra-net or an internet.

Thus, the invention provides methods for identifying a sequence similar or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an inter or intra net) and a query is made against the sequence database using the relevant sequences herein and associated plant phenotypes or gene functions.

Any sequence herein can be entered into the database, before or after querying the database. This provides for both expansion of the database and, if done before the querying step, for insertion of control sequences into the database. The control sequences can be detected by the query to ensure the general integrity of both the database and the query. As noted, the query can be performed using a web browser based interface. For example, the database can be a centralized public database such as those noted herein, and the querying can be done from a remote terminal or computer across an internet or intranet.

EXAMPLES

The following examples are intended to illustrate but not limit the present invention.

Example I

Full Length Gene Identification and Cloning

Putative transcription factor sequences (genomic or ESTs) related to known transcription factors were identified in the *Arabidopsis thaliana* GenBank database using the tblastn sequence analysis program using default parameters and a P-value cutoff threshold of −4 or −5 or lower, depending on the length of the query sequence. Putative transcription factor sequence hits were then screened to identify those containing particular sequence strings. If the sequence hits contained such sequence strings, the sequences were confirmed as transcription factors.

Alternatively, *Arabidopsis thaliana* cDNA libraries derived from different tissues or treatments, or genomic libraries were screened to identify novel members of a transcription family using a low stringency hybridization approach. Probes were synthesized using gene specific primers in a standard PCR reaction (annealing temperature 60° C.) and labeled with $^{32}$P dCTP using the High Prime DNA Labeling Kit (Boehringer Mannheim). Purified radiolabelled probes were added to filters immersed in Church hybridization medium (0.5 M NaPO$_4$ pH 7.0, 7% SDS, 1% w/v bovine serum albumin) and hybridized overnight at 60° C. with shaking. Filters were washed two times for 45 to 60 minutes with 1×SCC, 1% SDS at 60° C.

To identify additional sequence 5' or 3' of a partial cDNA sequence in a cDNA library, 5' and 3' rapid amplification of cDNA ends (RACE) was performed using the Marathon™ cDNA amplification kit (Clontech, Palo Alto, Calif.). Generally, the method entailed first isolating poly(A) mRNA, performing first and second strand cDNA synthesis to generate double stranded cDNA, blunting cDNA ends, followed by ligation of the Marathon™ Adaptor to the cDNA to form a library of adaptor-ligated ds cDNA.

Gene-specific primers were designed to be used along with adaptor specific primers for both 5' and 3' RACE reactions. Nested primers, rather than single primers, were used to increase PCR specificity. Using 5' and 3' RACE reactions, 5' and 3' RACE fragments were obtained, sequenced and cloned. The process can be repeated until 5' and 3' ends of the full-length gene were identified. Then the full-length cDNA was generated by PCR using primers specific to 5' and 3' ends of the gene by end-to-end PCR.

Example II

Construction of Expression Vectors

The sequence was amplified from a genomic or cDNA library using primers specific to sequences upstream and downstream of the coding region. The expression vector was pMEN20 or pMEN65, which are both derived from pMON316 (Sanders et al, (1987) *Nucleic Acids Res.* 15:1543-58) and contain the CaMV 35S promoter to express transgenes. To clone the sequence into the vector, both pMEN20 and the amplified DNA fragment were digested separately with SalI and NotI restriction enzymes at 37° C. for 2 hours. The digestion products were subject to electrophoresis in a 0.8% agarose gel and visualized by ethidium bromide staining. The DNA fragments containing the sequence and the linearized plasmid were excised and purified by using a Qiaquick gel extraction kit (Qiagen, CA). The fragments of interest were ligated at a ratio of 3:1 (vector to insert). Ligation reactions using T4 DNA ligase (New England Biolabs, MA) were carried out at 16° C. for 16 hours. The ligated DNAs were transformed into competent cells of the *E. coli* strain DH5alpha by using the heat shock method. The transformations were plated on LB plates containing 50 mg/l kanamycin (Sigma).

Individual colonies were grown overnight in five milliliters of LB broth containing 50 mg/l kanamycin at 37° C. Plasmid DNA was purified by using Qiaquick Mini Prep kits (Qiagen, CA).

Example III

Transformation of *Agrobacterium* with the Expression Vector

After the plasmid vector containing the gene was constructed, the vector was used to transform *Agrobacterium tumefaciens* cells expressing the gene products. The stock of *Agrobacterium tumefaciens* cells for transformation was made as described by Nagel et al. (1990) *FEMS MicroBiol. Letts.* 67: 325-328. *Agrobacterium* strain ABI was grown in 250 ml LB medium (Sigma) overnight at 28° C. with shaking until an absorbance ($A_{600}$) of 0.5-1.0 was reached. Cells were harvested by centrifugation at 4,000×g for 15 min at 4° C. Cells were then resuspended in 250 µl chilled buffer (1 mM HEPES, pH adjusted to 7.0 with KOH). Cells were centrifuged again as described above and resuspended in 125 µl chilled buffer. Cells were then centrifuged and resuspended two more times in the same HEPES buffer as described above at a volume of 100 µl and 750 µl, respectively. Resuspended cells were then distributed into 40 µl aliquots, quickly frozen in liquid nitrogen, and stored at −80° C.

Agrobacterium cells were transformed with plasmids prepared as described above following the protocol described by Nagel et al. For each DNA construct to be transformed, 50-100 ng DNA (generally resuspended in 10 mM Tris-HCl, 1 mM EDTA, pH 8.0) was mixed with 40 µl of Agrobacterium cells. The DNA/cell mixture was then transferred to a chilled cuvette with a 2 mm electrode gap and subject to a 2.5 kV charge dissipated at 25 µF and 200° F. using a Gene Pulser II apparatus (Bio-Rad). After electroporation, cells were immediately resuspended in 1.0 ml LB and allowed to recover without antibiotic selection for 2-4 hours at 28° C. in a shaking incubator. After recovery, cells were plated onto selective medium of LB broth containing 100 µg/ml spectinomycin (Sigma) and incubated for 24-48 hours at 28° C. Single colonies were then picked and inoculated in fresh medium. The presence of the plasmid construct was verified by PCR amplification and sequence analysis.

Example IV

Transformation of Arabidopsis Plants with Agrobacterium tumefaciens with Expression Vector After transformation of Agrobacterium tumefaciens with plasmid vectors containing the gene, single Agrobacterium colonies were identified, propagated, and used to transform Arabidopsis plants. Briefly, 500 ml cultures of LB medium containing 50 mg/l kanamycin were inoculated with the colonies and grown at 28° C. with shaking for 2 days until an absorbance ($A_{600}$) of >2.0 is reached. Cells were then harvested by centrifugation at 4,000×g for 10 min, and resuspended in infiltration medium (½× Murashige and Skoog salts (Sigma), 1× Gamborg's B-5 vitamins (Sigma), 5.0% (w/v) sucrose (Sigma), 0.044 µM benzylamino purine (Sigma), 200 µl/L Silwet L-77 (Lehle Seeds) until an absorbance ($A_{600}$) of 0.8 was reached.

Prior to transformation, Arabidopsis thaliana seeds (ecotype Columbia) were sown at a density of ~10 plants per 4" pot onto Pro-Mix BX potting medium (Hummert International) covered with fiberglass mesh (18 mm×16 mm). Plants were grown under continuous illumination (50-75 µE/m²/sec) at 22-23° C. with 65-70% relative humidity. After about 4 weeks, primary inflorescence stems (bolts) are cut off to encourage growth of multiple secondary bolts. After flowering of the mature secondary bolts, plants were prepared for transformation by removal of all siliques and opened flowers.

The pots were then immersed upside down in the mixture of Agrobacterium infiltration medium as described above for 30 sec, and placed on their sides to allow draining into a 1'×2' flat surface covered with plastic wrap. After 24 h, the plastic wrap was removed and pots are turned upright. The immersion procedure was repeated one week later, for a total of two immersions per pot. Seeds were then collected from each transformation pot and analyzed following the protocol described below.

Example V

Identification of Arabidopsis Primary Transformants

Seeds collected from the transformation pots were sterilized essentially as follows. Seeds were dispersed into in a solution containing 0.1% (v/v) Triton X-100 (Sigma) and sterile $H_2O$ and washed by shaking the suspension for 20 min. The wash solution was then drained and replaced with fresh wash solution to wash the seeds for 20 min with shaking. After removal of the second wash solution, a solution containing 0.1% (v/v) Triton X-100 and 70% ethanol (Equistar) was added to the seeds and the suspension was shaken for 5 min. After removal of the ethanol/detergent solution, a solution containing 0.1% (v/v) Triton X-100 and 30% (v/v) bleach (Clorox) was added to the seeds, and the suspension was shaken for 10 min. After removal of the bleach/detergent solution, seeds were then washed five times in sterile distilled $H_2O$. The seeds were stored in the last wash water at 4° C. for 2 days in the dark before being plated onto antibiotic selection medium (1× Murashige and Skoog salts (pH adjusted to 5.7 with 1M KOH), 1× Gamborg's B-5 vitamins, 0.9% phytagar (Life Technologies), and 50 mg/l kanamycin). Seeds were germinated under continuous illumination (50-75 µE/m²/sec) at 22-23° C. After 7-10 days of growth under these conditions, kanamycin resistant primary transformants ($T_1$ generation) were visible and obtained. These seedlings were transferred first to fresh selection plates where the seedlings continued to grow for 3-5 more days, and then to soil (Pro-Mix BX potting medium).

Primary transformants were crossed and progeny seeds ($T_2$) collected; kanamycin resistant seedlings were selected and analyzed. The expression levels of the recombinant polynucleotides in the transformants vary from about a 5% expression level increase to a least a 100% expression level increase. Similar observations are made with respect to polypeptide level expression.

Example VI

Identification of Arabidopsis Plants with Transcription Factor Gene Knockouts

The screening of insertion mutagenized Arabidopsis collections for null mutants in a known target gene was essentially as described in Krysan et al (1999) Plant Cell 11:2283-2290. Briefly, gene-specific primers, nested by 5-250 base pairs to each other, were designed from the 5' and 3' regions of a known target gene. Similarly, nested sets of primers were also created specific to each of the T-DNA or transposon ends (the "right" and "left" borders). All possible combinations of gene specific and T-DNA/transposon primers were used to detect by PCR an insertion event within or close to the target gene. The amplified DNA fragments were then sequenced which allows the precise determination of the T-DNA/transposon insertion point relative to the target gene. Insertion events within the coding or intervening sequence of the genes were deconvoluted from a pool comprising a plurality of insertion events to a single unique mutant plant for functional characterization. The method is described in more detail in Yu and Adam, U.S. application Ser. No. 09/177,733 filed Oct. 23, 1998.

Example VII

Identification of Modified Phenotype in Overexpressor or Gene Knockout Plants Experiments were performed to identify those transformants or knockouts that exhibited modified biochemical characteristics. Among the biochemicals that were assayed were insoluble sugars, such as arabinose, fucose, galactose, mannose, rhamnose or xylose or the like; prenyl lipids, such as lutein, β-carotene, xanthophyll-1, xanthophyll-2, chlorophylls A or B, or α-, δ- or γ-tocopherol or the like; fatty acids, such as 16:0 (palmitic acid), 16:1 (palmitoleic acid), 18:0 (stearic acid), 18:1 (oleic acid), 18:2 (linoleic acid), 20:0, 18:3 (linolenic acid), 20:1 (eicosenoic acid), 20:2, 22:1 (erucic acid) or the like; waxes, such as by altering the levels of C29, C31, or C33 alkanes; sterols, such as brassicasterol, campesterol, stigmasterol, sitosterol or stigmastanol or the like, glucosinolates, protein or oil levels Fatty acids were measured using two methods depending on whether the tissue was from leaves or seeds. For leaves, lipids were extracted and esterified with hot methanolic $H_2SO_4$ and partitioned into hexane from methanolic brine. For seed fatty acids, seeds were pulverized and extracted in methanol:heptane:toluene:2,2-dimethoxypropane:$H_2SO_4$ (39:34:20:5:2) for 90 minutes at 80° C. After cooling to room temperature the upper phase, containing the seed fatty acid esters, was subjected to GC analysis. Fatty acid esters from both seed and leaf tissues were analyzed with a Supelco SP-2330 column.

Glucosinolates were purified from seeds or leaves by first heating the tissue at 95° C. for 10 minutes. Preheated ethanol:water (50:50) is and after heating at 95° C. for a further 10 minutes, the extraction solvent is applied to a DEAE Sephadex column which had been previously equilibrated with 0.5 M pyridine acetate. Desulfoglucosinolates were eluted with 300 μl water and analyzed by reverse phase HPLC monitoring at 226 nm.

For wax alkanes, samples were extracted using an identical method as fatty acids and extracts were analyzed on a HP 5890 GC coupled with a 5973 MSD. Samples were chromatographed on a J&W DB35 mass spectrometer (J&W Scientific).

To measure prenyl lipids levels, seeds or leaves were pulverized with 1 to 2% pyrogallol as an antioxidant. For seeds, extracted samples were filtered and a portion removed for tocopherol and carotenoid/chlorophyll analysis by HPLC. The remaining material was saponified for sterol determination. For leaves, an aliquot was removed and diluted with methanol and chlorophyll A, chlorophyll B, and total carotenoids measured by spectrophotometry by determining absorbance at 665.2 nm, 652.5 nm, and 470 nm. An aliquot was removed for tocopherol and carotenoid/chlorophyll composition by HPLC using a Waters μBondapak® C18 column (4.6 mm×150 mm). The remaining methanolic solution was saponified with 10% KOH at 80° C. for one hour. The samples were cooled and diluted with a mixture of methanol and water. A solution of 2% methylene chloride in hexane was mixed in and the samples were centrifuged. The aqueous methanol phase was again re-extracted 2% methylene chloride in hexane and, after centrifugation, the two upper phases were combined and evaporated. 2% methylene chloride in hexane was added to the tubes and the samples were then extracted with one ml of water. The upper phase was removed, dried, and resuspended in 400 μl of 2% methylene chloride in hexane and analyzed by gas chromatography using a 50 m DB-5 ms (0.25 mm ID, 0.25 um phase, J&W Scientific).

Insoluble sugar levels were measured by the method essentially described by Reiter et al. *Plant J.* 12:335-345. This method analyzes the neutral sugar composition of cell wall polymers found in *Arabidopsis* leaves. Soluble sugars were separated from sugar polymers by extracting leaves with hot 70% ethanol. The remaining residue containing the insoluble polysaccharides was then acid hydrolyzed with allose added as an internal standard. Sugar monomers generated by the hydrolysis were then reduced to the corresponding alditols by treatment with $NaBH_4$, then were acetylated to generate the volatile alditol acetates which were then analyzed by GC-FID. Identity of the peaks was determined by comparing the retention times of known sugars converted to the corresponding alditol acetates with the retention times of peaks from wild-type plant extracts. Alditol acetates were analyzed on a Supelco SP-2330 capillary column (30 m×250 um×0.2 um) using a temperature program beginning at 180° C. for 2 minutes followed by an increase to 220° C. in 4 minutes. After holding at 220° C. for 10 minutes, the oven temperature is increased to 240° C. in 2 minutes and held at this temperature for 10 minutes and brought back to room temperature.

To identify plants with alterations in total seed oil or protein content, 150 mg of seeds from T2 progeny plants were subjected to analysis by Near Infrared Reflectance (NIR) using a Foss NirSystems Model 6500 with a spinning cup transport system.

Experiments were performed to identify those transformants or knockouts that exhibited an improved pathogen tolerance. For such studies, the transformants were exposed to biotropic fungal pathogens, such as *Erysiphe orontii*, and necrotropic fungal pathogens, such as *Fusarium oxysporum*. *Fusarium oxysporum* isolates cause vascular wilts and damping off of various annual vegetables, perennials and weeds (Mauch-Mani and Slusarenko (1994) *Mol. Plant-Microbe Interact.* 7: 378-383). For *Fusarium oxysporum* experiments, plants grown on Petri dishes were sprayed with a fresh spore suspension of *F. oxysporum*. The spore suspension was prepared as follows: A plug of fungal hyphae from a plate culture was placed on a fresh potato dextrose agar plate and allowed to spread for one week. 5 ml sterile water was then added to the plate, swirled, and pipetted into 50 ml Armstrong *Fusarium* medium. Spores were grown overnight in *Fusarium* medium and then sprayed onto plants using a Preval paint sprayer. Plant tissue was harvested and frozen in liquid nitrogen 48 hours post infection.

*Erysiphe orontii* is a causal agent of powdery mildew. For *Erysiphe orontii* experiments, plants were grown approximately 4 weeks in a greenhouse under 12 hour light (20 C, ~30% relative humidity (rh)). Individual leaves were infected with *E. orontii* spores from infected plants using a camel's hair brush, and the plants were transferred to a Percival growth chamber (20 C, 80% rh.). Plant tissue was harvested and frozen in liquid nitrogen 7 days post infection.

*Botrytis cinerea* is a necrotrophic pathogen. *Botrytis cinerea* was grown on potato dextrose agar in the light. A spore culture was made by spreading 10 ml of sterile water on the fungus plate, swirling and transferring spores to 10 ml of sterile water. The spore inoculum (approx. 105 spores/ml) was used to spray 10 day-old seedlings grown under sterile conditions on MS (-sucrose) media. Symptoms were evaluated every day up to approximately 1 week.

Infection with bacterial pathogens *Pseudomonas syringae* pv maculicola strain 4326 and pv maculicola strain 4326 was performed by hand inoculation at two doses. Administration of two inoculation doses allows the differentiation between plants with enhanced susceptibility and plants with enhanced resistance to the pathogen. Plants were grown for 3 weeks in the greenhouse, then transferred to the growth chamber for the remainder of their growth. Psm ES4326 was hand inoculated with 1 ml syringe on 3 fully-expanded leaves per plant (4½ wk old), using at least 9 plants per overexpressing line at two inoculation doses, OD=0.005 and OD=0.0005. Disease scoring occurred at day 3 post-inoculation with pictures of the plants and leaves taken in parallel In some instances, expression patterns of the pathogen induced genes (such as defense genes) were monitored by microarray experiments. cDNAs were generated by PCR and resuspended at a final concentration of ~100 ng/μl in 3×SSC or 150 mM Na-phosphate (Eisen and Brown (1999) *Meth. in Enzymol.* 303:179-205). The cDNAs were spotted on microscope glass slides coated with polylysine. The prepared cDNAs were aliquoted into 384 well plates and spotted on the slides using an x-y-z gantry (OmniGrid) purchased from GeneMachines (Menlo Park, Calif.) outfitted with quill type pins purchased from Telechem International (Sunnyvale, Calif.). After spotting, the arrays were cured for a minimum of one week at room temperature, rehydrated and blocked following the protocol recommended by Eisen and Brown (1999).

Sample total RNA (10 μg) samples were labeled using fluorescent Cy3 and Cy5 dyes. Labeled samples were resuspended in 4×SSC/0.03% SDS/4 μg salmon sperm DNA/2 μg tRNA/50 mM Na-pyrophosphate, heated for 95° C. for 2.5 minutes, spun down and placed on the array. The array was then covered with a glass coverslip and placed in a sealed chamber. The chamber was then kept in a water bath at 62° C. overnight. The arrays were washed as described in Eisen and Brown (1999) and scanned on a General Scanning ScanArray™ 3000 laser scanner. The resulting files are subsequently quantified using Imagene a software purchased from BioDiscovery (Los Angeles, Calif.).

Measurement of Photosynthesis.

Photosynthesis was measured using a LICOR LI-6400 (Li-Cor® Biosciences, Lincoln, Nebr.). The LI-6400 used infrared gas analyzers to measure carbon dioxide to generate a photosynthesis measurement. It was based upon the difference of the $CO_2$ reference (the amount put into the chamber) and the $CO_2$ sample (the amount that leaves the chamber). Since photosynthesis is the process of converting $CO_2$ to carbohydrates, we expected to see a decrease in the amount of $CO_2$ sample. From this difference, a photosynthesis rate could be generated. In some cases, respiration may occur and an increase in $CO_2$ detected. To perform measurements, the LI-6400 as set-up and calibrated as per LI-6400 standard directions. Photosynthesis was measured in the youngest, most fully expanded leaf at 300 and 1000 ppm $CO_2$ using a metal halide light source. This light source provided about 700 $\mu E\ m^{-2}\ s^{-1}$.

Environmental Stress Tolerance.

Experiments were performed to identify those transformants or knockouts that exhibited an improved environmental stress tolerance. For such studies, the transformants were exposed to a variety of environmental stresses. Plants were exposed to chilling stress (6 hour exposure to 4°-8° C.), heat stress (6 hour exposure to 32°-37° C.), high salt stress (germination in 150 mM NaCl or a 6 hour exposure of plants to 200 mM NaCl), drought stress (withholding of water for 168 hours), hyperosmotic stress (for example, germination in 9.4% sucrose or a 6 hour exposure to 3 M mannitol), desiccation, or nutrient limitation (nitrogen, phosphate, and potassium) (Nitrogen: all components of MS medium remained constant except N was reduced to 20 mg/L of $NH_4NO_3$, or Phosphate: All components of MS medium except $KH_2PO_4$, which was replaced by $K_2SO_4$, Potassium: All components of MS medium except removal of $KNO_3$ and $KH_2PO_4$, which were replaced by $NaH_4PO_4$). For analysis of ability to tolerate desiccation (a plate-based water deprivation assay), seedlings were grown for 14 days on MS+Vitamins+1% sucrose at 22° C. Plates were opened in the sterile hood for 3 hr for hardening and then seedlings were removed from the media and let dry for two hours in the hood. After this time the plants were transferred back to plates and incubated at 22° C. for recovery. The plants were then evaluated after five days.

Soil-based drought assays. Seeds were sterilized by a 2 minute ethanol treatment followed by 20 minutes in 30% bleach/0.01% Tween and five washes in distilled water. Seeds were sown to MS agar in 0.1% agarose and stratified for three days at 4° C., before transfer to growth cabinets with a temperature of 22° C. After seven days of growth on selection plates, seedlings were transplanted to 3.5 inch diameter clay pots containing 80 g of a 50:50 mix of vermiculite:perlite topped with 80 g of ProMix. Typically, each pot contains 14 seedlings, and plants of the transgenic line being tested were in separate pots to the wild-type controls. Pots containing the transgenic line versus control pots were interspersed in the growth room, maintained under 24-hour light conditions (18-23° C., and 90-100 $\mu E\ m^{-2}\ s^{-1}$) and watered for a period of 14 days. Water was then withheld and pots were placed on absorbent paper for a period of 8-10 days to apply a drought treatment. After this period, a visual qualitative "drought score" from 0-6 was assigned to record the extent of visible drought stress symptoms. A score of "6" corresponded to no visible symptoms whereas a score of "0" corresponded to extreme wilting and the leaves having a "crispy" texture. At the end of the drought period, pots were re-watered and scored after 5-6 days; the number of surviving plants in each pot was counted, and the proportion of the total plants in the pot that survived was calculated.

In a given experiment, we typically compared 6 or more pots of a transgenic line with 6 or more pots of the appropriate control. The mean drought score and mean proportion of plants surviving (survival rate) were calculated for both the transgenic line and the wild-type pots. In each case a p-value* was calculated, which indicated the significance of the difference between the two mean values. The results for each transgenic line across each planting for a particular project were then presented in a results table.

For the assays where control and experimental plants were in separate pots, survival was analyzed with a logistic regression to account for the fact that the random variable is a proportion between 0 and 1. The reported p-value was the significance of the experimental proportion was to the control, based upon regressing the logit-transformed data.

Drought score, being an ordered factor with no real numeric meaning, is analyzed with a non-parametric test between the experimental and control groups. The p-value was calculated with a Mann-Whitney rank-sum test.

Experiments were performed to identify those transformants or knockouts that exhibited a modified structure and development characteristics. For such studies, the transformants were observed by eye to identify novel structural or developmental characteristics associated with the ectopic expression of the polynucleotides or polypeptides of the invention.

Experiments were performed to identify those transformants or knockouts that exhibited modified sugar-sensing. For such studies, seeds from transformants were germinated on media containing 5% glucose or 9.4% sucrose which normally partially restrict hypocotyl elongation. Plants with altered sugar sensing may have either longer or shorter hypocotyls than normal plants when grown on this media. Additionally, other plant traits may be varied such as root mass.

Flowering time was measured by the number of rosette leaves present when a visible inflorescence of approximately 3 cm is apparent Rosette and total leaf number on the progeny stem are tightly correlated with the timing of flowering (Koornneef et al (1991) *Mol. Gen. Genet* 229:57-66. The vernalization response was measured. For vernalization treatments, seeds were sown to MS agar plates, sealed with micropore tape, and placed in a 4° C. cold room with low light levels for 6-8 weeks. The plates were then transferred to the growth rooms alongside plates containing freshly sown non-vernalized controls. Rosette leaves were counted when a visible inflorescence of approximately 3 cm was apparent.

Table 5 shows exemplary modified phenotypes observed for particular overexpressor or knockout plants. Modified phenotypes observed for particular overexpressor or knockout plants were provided in Appendix A in U.S. priority application Ser. No. 09/713,994, filed Nov. 16, 2000 (Appendix A is herein incorporated by reference in its entirety). For a particular overexpressor that shows a less beneficial characteristic, it may be more useful to select a plant with a decreased expression of the particular transcription factor. For a particular knockout that shows a less beneficial characteristic, it may be more useful to select a plant with an increased expression of the particular transcription factor.

Example VIII

Identification of Homologous Sequences

Homologous sequences from *Arabidopsis* and plant species other than *Arabidopsis* were identified using database sequence search tools, such as the Basic Local Alignment Search Tool (BLAST) (Altschul et al. (1990) *J. Mol. Biol.* 215:403-410; and Altschul et al. (1997) *Nucl. Acid Res.* 25: 3389-3402). The tblastx sequence analysis programs were employed using the BLOSUM-62 scoring matrix (Henikoff, S. and Henikoff, J. G. (1992) *Proc. Natl. Acad. Sci. USA* 89: 10915-10919).

Identified *Arabidopsis* homologous sequences are provided in Tables 4 and 5 and included in the Sequence Listing.

The percent sequence identity among these sequences is as low as 46% sequence identity. Additionally, the entire NCBI GenBank database was filtered for sequences from all plants except *Arabidopsis thaliana* by selecting all entries in the NCBI GenBank database associated with NCBI taxonomic ID 33090 (Viridiplantae; all plants) and excluding entries associated with taxonomic ID 3701 (*Arabidopsis thaliana*). These sequences were compared to sequences representing genes of SEQ IDs Nos. 1-54 on Sep. 26, 2000 using the Washington University TBLASTX algorithm (version 2.0a19 MP). For each gene of SEQ IDs Nos. 1-54, individual comparisons were ordered by probability score (P-value), where the score reflects the probability that a particular alignment occurred by chance. For example, a score of 3.6e-40 is $3.6 \times 10^{-40}$. In addition to P-values, comparisons were also scored by percentage identity. Percentage identity reflects the degree to which two segments of DNA or protein are identical over a particular length.

Example IX

Trait summary for Transgenic Plants Overexpressing Sequences of the Invention

Appendix A, filed with priority U.S. patent application Ser. No. 09/713,994 on Nov. 16, 2000, provides traits observed when plants were modified to alter the expression of additional polynucleotide and polypeptide sequences.

The entire contents of Appendix A filed with priority U.S. patent application Ser. No. 09/713,994 are hereby incorporated by reference.

Table 5, below, provides a summary of the traits associated with prior filed Appendix A and the sequences of the invention. Each of the traits listed in Table 5 was observed to be modified in transgenic plants when the expression levels of each of these exemplary sequences were altered by overexpression of suppression. Table 5 lists the Gene IDentifier (GID) of each sequence, the SEQ ID NO: of the polynucleotide corresponding to the GID number, whether the sequence encoded by the respective GID was overexpressed or knocked out in plants, and the trait category and experimental observation made when the expression level of the respective GID was so altered.

TABLE 5

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G4 | 111 | 112 | OE | Disease resistance | Increased resistance to *Botrytis* |
| G5 | 115 | 116 | OE | Plant size | Small plant |
| G6 | 119 | 120 | | | |
| G7 | 123 | 124 | | | |
| G9 | 48 | 128 | OE | Root morphology | Increased root mass |
| | | | OE | Salt tolerance | Greater tolerance to 150 mM NaCl in a germination assay |
| | | | OE | Sugar sensing/ sucrose tolerance | More tolerant to glucose; greater germination and growth on 5% glucose medium |
| | | | OE | Hormone sensitivity | Less sensitive to ABA; seedlings were larger and greener in 0.5 µM ABA in a germination assay |
| | | | OE | Cold tolerance | More tolerant to cold; seedlings had less anthocyanin during growth in 8° C. |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G14 | 130 | 131 | | | |
| G19 | 3 | 135 | OE | Disease resistance | Increased resistance to *Erysiphe* |
| | | | OE | Hormon sensitivity | Repressed by methyl jasmonate and induced by ACC |
| G20 | 138 | 139 | OE | Seed sterols | Increase in campesterol |
| G22 | 19 | 143 | OE | Salt tolerance | Greater tolerance to 150 mM NaCl in a germination assay |
| G23 | 146 | 147 | | | |
| G25 | 150 | 151 | OE | Trichome | Fewer trichomes at seedling stage |
| | | | OE | *Fusarium* | Expression induced by *Fusarium* infection |
| G26 | 60 | 155 | OE | Sugar sensing/ sucrose tolerance | Decreased germination and growth on 5% glucose medium |
| G27 | 105 | 159 | OE | Plant size | Abnormal development, small |
| | | | OE | Altered C/N sensing | Increased sensitivity to media with low nitrogen or lacking nitrogen source |
| G28 | 5 | 163 | OE | Disease resistance | Increased resistance to *Botrytis* |
| | | | OE | Disease resistance | Increased resistance to *Erysiphe* |
| | | | OE | Disease resistance | Increased resistance to *Sclerotinia* |
| G29 | 166 | 167 | | | |
| G30 | 170 | 171 | OE | Leaf morphology | Glossy green leaves |
| | | | OE | Light response | Increased shade tolerance; lack of shade avoidance phenotype |
| G35 | 174 | 175 | | | |
| G36 | 178 | 179 | | | |
| G38 | 61 | 183 | OE | Sugar sensing/ sucrose tolerance | Reduced germination on 5% glucose medium |
| G39 | 186 | 187 | | | |
| G43 | 62 | 191 | OE | Sugar sensing/ sucrose tolerance | Decreased germination and growth on 5% glucose medium |
| G44 | 194 | 195 | | | |
| G142 | 198 | 199 | OE | Flowering time | Early flowering |
| G148 | 202 | 203 | | | |
| G152 | 206 | 207 | | | |
| G157 | 210 | 211 | OE | Flowering time | Modest overexpression triggers early flowering; greater overexpression delays flowering |
| G161 | 214 | 215 | OE | Altered C/N sensing | Increased sensitivity to media with low nitrogen or lacking nitrogen source |
| G164 | 218 | 219 | | | |
| G177 | 222 | 223 | | | |
| G178 | 226 | 227 | | | |
| G180 | 100 | 231 | OE | Seed oil content | Decreased seed oil |
| | | | OE | Flowering time | Early flowering |
| G187 | 56 | 235 | OE | Morphology | Long, thin cotyledons at seedling stage; several flower abnormalities including strap-like, sepaloid petals |
| G188 | 1 | 239 | KO | Salt and hyperosmotic stress | More tolerant to salt and/or osmotic stress: better germination in 150 mM NaCl, 300 mM mannitol, 9.4% sucrose or 5% glucose |
| | | | KO | Disease resistance | Increased susceptibility to *Fusarium* |
| G190 | 242 | 243 | | | |
| G192 | 91 | 247 | OE | Seed oil content | Decreased seed oil content |
| | | | OE | Flowering time | Late flowering |
| G194 | 250 | 251 | OE | Plant size | Small plant |
| | | | OE | Water deprivation tolerance | More tolerant to desiccation |
| G197 | 254 | 255 | OE | Seed oil content | Increased seed oil |
| | | | OE | Seed protein content | Decreased seed protein |
| G198 | 258 | 259 | OE | Salt tolerance | More tolerant to salt; seedlings were larger and greener in a germination assay on 150 mM NaCl |
| G200 | 262 | 263 | KO | Altered C/N sensing | Increased sensitivity to media with low nitrogen or lacking nitrogen source |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G201 | 266 | 267 | OE | Seed protein content | Increased seed protein content |
|  |  |  | OE | Seed oil content | Decreased seed oil content |
| G202 | 270 | 271 | OE | Seed protein content | Decreased seed protein content |
|  |  |  | OE | Seed oil content | Increased seed oil content |
| G203 | 274 | 275 |  |  |  |
| G204 | 279 |  |  |  |  |
| G206 | 282 | 280 | OE | Seed size | Large seeds |
| G207 | 63 | 284 | OE | Sugar sensing/ glucose tolerance | Decreased germination on 5% glucose medium |
|  |  |  | KO | Disease resistance | Increased susceptibility to *Botrytis* |
|  |  |  | OE | Disease resistance | Increased resistance to *Erysiphe* |
| G208 | 102 | 288 | OE | Flowering time | Early flowering |
| G209 | 291 | 292 |  |  |  |
| G210 | 295 | 296 |  |  |  |
| G212 | 301 | 299 | OE | Altered trichome initiation and number | Partially to fully glabrous on adaxial surface of leaves |
| G214 | 35 | 303 | OE | Leaf fatty acids | Increased leaf fatty acids |
|  |  |  | OE | Leaf prenyl lipids | Increased leaf chlorophyll and carotenoids |
|  |  |  | OE | Flowering time | Late flowering |
|  |  |  | OE | Seed prenyl lipids | Increased seed lutein |
| G215 | 308 | 306 |  |  |  |
| G216 | 311 | 309 |  |  |  |
| G217 | 312 | 313 | OE | Seed fatty acids | Increase in 20:2 fatty acid in seeds |
| G219 | 316 | 317 |  |  |  |
| G220 | 320 | 321 |  |  |  |
| G222 | 324 | 325 | OE | Seed oil content | Decreased seed oil content |
|  |  |  | OE | Seed protein content | Increased seed protein content |
| G225 | 20 | 329 | OE | Root | Increased root hairs |
|  |  |  | OE | Trichome | Glabrous, lack of trichomes |
|  |  |  | OE | C/N sensing | Greater growth and/or vigor on media with low nitrogen or lacking nitrogen source |
|  |  |  | OE | Nutrient uptake | Increased tolerance to nitrogen-limited medium |
| G226 | 21 | 333 | OE | Nutrient uptake | Increased tolerance to nitrogen-limited medium |
|  |  |  | OE | Seed protein content | Increased seed protein |
|  |  |  | OE | Root | Increased root hairs |
|  |  |  | OE | Trichome | Glabrous, lack of trichomes |
|  |  |  | OE | Sodium chloride | More tolerant to salt; seedlings were larger and greener in a germination assay on 150 mM NaCl |
|  |  |  | OE | Altered C/N sensing | Greater growth and/or vigor on media with low nitrogen or lacking nitrogen source |
| G228 | 336 | 337 |  |  |  |
| G229 | 36 | 341 | OE | Seed protein content | Decreased seed protein |
|  |  |  | OE | Seed oil content | Increased seed oil |
|  |  |  | OE | Other biochemistry | Up-regulation of genes involved in secondary metabolism |
| G231 | 74 | 345 | OE | Leaf fatty acids | Increased leaf unsaturated fatty acids |
|  |  |  | OE | Seed protein content | Decreased seed protein content |
|  |  |  | OE | Seed oil content | Increased seed oil content |
| G232 | 348 | 349 |  |  |  |
| G233 | 37 | 353 | OE | Disease resistance | Increased resistance to *Botrytis* |
|  |  |  | OE | Disease resistance | Increased resistance to *Erysiphe* |
| G234 | 92 | 357 | OE | Flowering time | Late flowering |
|  |  |  | OE | Altered C/N sensing | Greater growth and/or vigor on media with low nitrogen or lacking nitrogen source |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G237 | 7 | 361 | OE | Leaf biochemistry | Increased leaf insoluble sugars |
| | | | OE | Disease resistance | Increased resistance to *Erysiphe* |
| | | | OE | Altered C/N sensing | Greater growth and/or vigor on media with low nitrogen or lacking nitrogen source |
| G239 | 364 | 365 | OE | Expression/ABA treatment | Expression induced by 0.5 μM ABA |
| | | | OE | Expression from drought | Expression induced by drought |
| | | | OE | Expression/heat treatment | Expression induced by 32° C. |
| | | | OE | Expression/hyperosmotic stress | Expression induced by hyperosmotic stress |
| G241 | 368 | 369 | OE | Seed oil content | Decreased seed oil |
| | | | KO | Seed protein content | Altered seed protein content |
| | | | OE | Sugar sensing/ glucose tolerance | Decreased germination and growth on 5% glucose medium |
| G242 | 372 | 373 | OE | Leaf insoluble sugars | Increased arabinose |
| G245 | 376 | 377 | | | |
| G249 | 380 | 381 | OE | Flowering time | Late flowering |
| | | | OE | Time to senescence | Delayed senescence |
| G251 | 384 | 385 | | | |
| G252 | 388 | 389 | | | |
| G254 | 64 | 393 | OE | Sugar sensing/ glucose tolerance | Decreased germination and growth on 5% glucose medium |
| G256 | 22 | 397 | OE | Cold tolerance | More tolerant to cold; increased seedling vigor and root growth at 8° C. in germination and growth assays |
| G260 | 400 | 401 | | | |
| G261 | 4 | 404 | OE | Disease resistance | Increased susceptibility to *Botrytis* |
| G262 | 407 | 406 | | | |
| G263 | 65 | 409 | OE | Sugar sensing/ glucose tolerance | Decreased root growth on 9.4% sucrose medium |
| | | | OE | Tissue-specific expression | Root specific expression |
| G271 | 412 | 413 | | | |
| G273 | 415 | 416 | | | |
| G274 | 75 | 419 | OE | Leaf insoluble sugars | Increased leaf arabinose |
| G279 | 421 | 422 | | | |
| G285 | 424 | 425 | | | |
| G291 | 427 | 428 | OE | Seed oil content | Increased seed oil content |
| G306 | 430 | 431 | OE | Leaf insoluble sugars | Altered leaf insoluble sugars: increased galactose, decreased arabinose, mannose, rhamnose and xylose |
| G307 | 76 | 435 | OE | Sugar sensing/ glucose tolerance | No germination on 5% glucose medium |
| G308 | 66 | 439 | | | |
| G313 | 442 | 443 | | | |
| G315 | 446 | 447 | | | |
| G321 | 450 | 451 | | | |
| G322 | 453 | 454 | | | |
| G326 | 457 | 458 | OE | Altered C/N sensing | Increased sensitivity to media with low nitrogen or lacking nitrogen source |
| G328 | 461 | 462 | | | |
| G329 | 464 | 465 | | | |
| G330 | 467 | 468 | OE | Cell wall composition | Xylose and rhamnose levels were elevated |
| G335 | 473 | 471 | | | |
| G343 | 474 | 475 | OE | Glyphosate resistance | Increased glyphosate resistance |
| G345 | 477 | 478 | | | |
| G346 | 77 | 482 | OE | Leaf fatty acids | Significant increase in 18:2 leaf fatty acid level |
| | | | OE | Seed oil content | Decreased seed oil |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G355 | 484 | 485 | | | |
| G357 | 488 | 489 | OE | Morphology and development | Most transformants died by the flowering stage; potential herbicide target |
| G361 | 93 | 493 | OE | Flowering time | Late flowering |
| G363 | 496 | 497 | | | |
| G364 | 500 | 501 | OE | Morphology and development | Most transformants died by the flowering stage; potential herbicide target |
| G368 | 504 | 505 | | | |
| G371 | 508 | 509 | OE | Disease resistance | Increased susceptibility to *Botrytis* |
| G376 | 511 | 512 | | | |
| G378 | 16 | 515 | OE | Disease resistance | Increased resistance to *Erysiphe* |
| G384 | 518 | 519 | OE | Altered C/N sensing | Increased sensitivity to media with low nitrogen or lacking nitrogen source |
| G385 | 521 | 522 | OE | Plant size | Small plant |
| | | | OE | Inflorescence | Short inflorescence stems |
| | | | OE | Leaf morphology | Dark green plant |
| G388 | 525 | 526 | | | |
| G389 | 529 | 530 | | | |
| G390 | 533 | 534 | OE | Flowering time | Early flowering |
| | | | OE | Plant morphology | Abnormal, disorganized phyllotaxy; exhibited stem bifurcations in which shoot meristems split to form two or three separate shoots |
| G391 | 537 | 538 | OE | Altered architecture | Altered shoot development; T1 plants were dark green with short bolts, small leaves and short siliques |
| G393 | 541 | 542 | | | |
| G394 | 33 | 546 | OE | Cold tolerance | More sensitive to 8° C.; plants became chlorotic and leaves senesced prematurely |
| G395 | 549 | 550 | | | |
| G396 | 552 | 553 | | | |
| G397 | 556 | 557 | | | |
| G398 | 560 | 561 | | | |
| G399 | 564 | 565 | | | |
| G400 | 567 | 568 | | | |
| G404 | 570 | 571 | | | |
| G409 | 8 | 574 | OE | Disease resistance | Increased resistance to *Erysiphe* |
| G411 | 576 | 577 | | | |
| G412 | 580 | 581 | | | |
| G414 | 584 | 585 | | | |
| G418 | 9 | 588 | OE | Disease resistance | Increased resistance to *Pseudomonas* |
| | | | OE | Seed protein content | Decreased seed protein content |
| G419 | 23 | 591 | OE | Low nutrient tolerance | Increased tolerance to potassium-free medium |
| G425 | 593 | 594 | OE | Disease resistance | Increased resistance to *Pseudomonas* |
| G426 | 596 | 597 | | | |
| G428 | 49 | 601 | OE | Leaf insoluble sugars | Increased leaf insoluble sugars |
| | | | OE | Leaf morphology | Severe lobing of leaves conferring a parsley-like shape |
| G431 | 55 | 605 | OE | Developmental defects | Extremely deleterious or lethal |
| G432 | 608 | 609 | | | |
| G435 | 612 | 613 | OE | Leaf insoluble sugars | Increased leaf insoluble sugars |
| G438 | 52 | 616 | KO | Altered architecture | Reduced branching |
| | | | KO | Stem lignification | Reduced lignin |
| | | | OE | Leaf morphology | Increased leaf size; larger, flatter leaves |
| | | | OE | Leaf morphology | Altered leaf shape; broad flat leaves |
| G439 | 619 | 620 | | | |
| G440 | 623 | 624 | OE | Disease resistance | Increased resistance to *Erysiphe* |
| G441 | 627 | 628 | | | |
| G442 | 631 | 632 | | | |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G443 | 635 | 636 | | | |
| G444 | 639 | 640 | | | |
| G448 | 643 | 644 | | | |
| G449 | 647 | 648 | | | |
| G451 | 651 | 652 | | | |
| G452 | 655 | 656 | | | |
| G455 | 659 | 660 | | | |
| G456 | 663 | 664 | OE | Seed protein content | Decreased seed protein |
| | | | OE | Seed oil content | Increased seed oil |
| G459 | 666 | 667 | | | |
| G461 | 670 | 671 | | | |
| G462 | 673 | 674 | | | |
| G463 | 677 | 678 | | | |
| G464 | 24 | 682 | OE | Seed oil content | Increased seed oil |
| | | | OE | Heat tolerance | More tolerance to heat; seedlings were larger and greener in germination and growth assays at 32° C. |
| | | | OE | Leaf morphology | Altered leaf shape |
| | | | OE | Seed protein content | Decreased seed protein content |
| G466 | 685 | 686 | | | |
| G467 | 688 | 689 | | | |
| G470 | 57 | 692 | OE | Fertility | Short stamen filaments; pollen produced, but not deposited on the stigma |
| G474 | 695 | 696 | | | |
| G475 | 699 | 700 | OE | Flowering time | Early flowering |
| G481 | 703 | 704 | OE | Hyperosmotic stress | More tolerant to mannitol; greater germination and growth on 300 mM mannitol medium |
| | | | OE | Hormone sensitivity | Less sensitive to ABA; seedlings were larger and greener in 0.5 µM ABA in a germination assay |
| | | | OE | Sugar sensing/sucrose tolerance | More tolerant to sucrose; better germination on 9.4% sucrose medium |
| | | | OE | Heat tolerance | More tolerance to heat; seedlings were larger and greener in germination and growth assays at 32° C. |
| | | | OE | Water deprivation tolerance | More tolerant to desiccation and drought |
| G482 | 25 | 708 | OE | Salt tolerance | More tolerant to salt; seedlings were larger and greener in a germination assay on 150 mM NaCl |
| | | | OE | Hyperosmotic stress | More tolerant to mannitol; greater germination and growth on 300 mM mannitol medium |
| | | | OE | Heat tolerance | More tolerance to heat; seedlings were larger and greener in germination and growth assays at 32° C. |
| | | | OE | Water deprivation tolerance | Increased survival and recovery from drought |
| G483 | 711 | 712 | OE | Water deprivation tolerance | Better recovery from drought |
| G484 | 714 | 715 | KO | Altered seed glucosinolates | Altered glucosinolate profile |
| | | | OE | Water deprivation tolerance | More tolerant to desiccation |
| G485 | 718 | 719 | OE | Flowering time | Early flowering |
| | | | KO | Flowering time | Late flowering |
| | | | OE | Water deprivation tolerance | Increased survival and recovery from drought |
| | | | OE | Salt tolerance | More tolerant to salt; seedlings were larger and greener in a germination assay on 150 mM NaCl |
| | | | OE | Cold tolerance | Greater tolerance to cold; in 8° C. in germination and growth assays; seedlings were larger and greener |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| | | | | | during germination and larger during growth |
| | | | OE | Hormone sensitivity | Less sensitive to ABA; seedlings were larger and greener in 0.5 μM ABA in a germination assay |
| | | | OE | Sugar sensing/sucrose tolerance | More tolerant to sucrose; better germination on 9.4% sucrose medium |
| G486 | 94 | 723 | OE | Flowering time | Late flowering |
| | | | OE | Altered C/N sensing | Greater growth and/or vigor on media with low nitrogen or lacking nitrogen source |
| G489 | 34 | 727 | OE | Hyperosmotic stress | More tolerant to mannitol; greater germination and growth on 300 mM mannitol medium |
| | | | OE | Cold tolerance | Greater tolerance to cold; in 8° C. in germination and growth assays; seedlings were larger, greened and had less anthocyanin during germination and growth |
| | | | OE | Water deprivation tolerance | More tolerant to desiccation and drought |
| G501 | 730 | 731 | | | |
| G502 | 26 | 734 | KO | Hyperosmotic stress | Increased sensitivity to 5% glucose or 150 mM NaCl |
| G503 | 737 | 738 | | | |
| G505 | 743 | 741 | OE | Altered C/N sensing | Greater sensitivity to media with low nitrogen or lacking nitrogen source |
| G508 | 744 | 745 | | | |
| G509 | 748 | 749 | KO | Seed oil content | Increased seed oil content |
| | | | KO | Seed protein content | Decreased seed protein content |
| | | | OE | Seed glucosinolates | Increased M39489 and M39497 |
| G511 | 751 | 752 | | | |
| G513 | 755 | 756 | | | |
| G514 | 759 | 760 | | | |
| G516 | 764 | 762 | OE | Hyperosmotic stress | More tolerant to mannitol; greater germination and growth on 300 mM mannitol medium |
| | | | OE | Cold tolerance | Increased tolerance to cold; in an 8° C. growth assay; seedlings had less anthocyanin |
| | | | OE | Seed morphology | Seeds of one line larger |
| | | | OE | Plant size | Seedlings of several lines larger |
| G523 | 765 | 766 | | | |
| G524 | 769 | 770 | | | |
| G525 | 11 | 774 | OE | Disease resistance | Increased tolerance to *Pseudomonas* |
| | | | OE | Leaf insoluble sugars | Increased leaf insoluble sugars |
| G526 | 27 | 778 | OE | Tolerance to hyperosmotic stress | Increased sensitivity to 300 mM mannitol or 10% polyethylene glycol |
| G528 | 781 | 782 | | | |
| G529 | 785 | 786 | | | |
| G531 | 788 | 789 | | | |
| G532 | 792 | 793 | | | |
| G533 | 796 | 797 | | | |
| G535 | 800 | 801 | | | |
| G536 | 67 | 805 | OE | Sugar sensing/ glucose tolerance | Decreased germination and growth on 5% glucose medium |
| G560 | 838 | 839 | | | |
| G561 | 28 | 843 | OE | Seed oil content | Increased seed oil content |
| | | | OE | Nutrient uptake | Increased tolerance to potassium-free medium |
| G562 | 97 | 847 | OE | Flowering time | Late flowering |
| G563 | 850 | 851 | | | |
| G564 | 854 | 855 | | | |
| G566 | 858 | 859 | | | |
| G569 | 17 | 863 | OE | Defense gene expression | Several genes repressed by G569 overexpression, including PR-1, |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| | | | | | MtN21 (upregulated by *Erysiphe*), PAR-1b (inducible by sucrose and salicylic acid), drought-induced protein Dr4, WAK 1 (upregulated by *Erysiphe*), antifungal protein, a glycine rich protein, polygalacturonase, putative β-expansin, flavonol synthase and pathogen-inducible protein CXc750. 12-oxo-phytodienoate 10,11-reductase (octadecanoid biosynthesis), lipoxygenase, GST and allene oxide synthase were consistently induced |
| G570 | 866 | 867 | | | |
| G571 | 53 | 871 | KO | Time to senescence | Delayed senescence |
| | | | KO | Flowering time | Late flowering |
| G572 | 873 | 874 | OE | Disease resistance | Increased resistance to *Erysiphe* |
| G573 | 877 | 878 | | | |
| G575 | 881 | 882 | | | |
| G579 | 885 | 886 | | | |
| G582 | 889 | 890 | | | |
| G584 | 44 | 894 | OE | Seed morphology | Large seeds |
| G586 | 897 | 898 | | | |
| G589 | 900 | 901 | | | |
| G590 | 904 | 905 | KO | Seed oil content | Increased seed oil content |
| | | | OE | Flowering time | Early flowering |
| | | | OE | Altered C/N sensing | Greater growth and/or vigor on media with low nitrogen or lacking nitrogen source |
| G591 | 10 | 909 | OE | Disease resistance | Increased resistance to *Erysiphe* |
| | | | OE | Disease resistance | Increased resistance to *Botrytis* |
| | | | OE | Disease resistance | Increased resistance to *Sclerotinia* |
| | | | OE | Flowering time | Late flowering |
| G592 | 101 | 913 | OE | Flowering time | Early flowering |
| G593 | 916 | 917 | | | |
| G595 | 920 | 921 | | | |
| G598 | 78 | 925 | OE | Seed oil content | Increased seed oil |
| | | | OE | Leaf insoluble sugars | Altered insoluble sugars; increased galactose levels |
| G599 | 928 | 929 | OE | Leaf morphology | Extreme rolling and curling of rosette leaves, giving the rosettes a pinwheel-like appearance |
| G603 | 932 | 933 | | | |
| G605 | 79 | 937 | OE | Leaf fatty acids | Altered leaf fatty acid composition; decreased 18:3 and increased 16:0 |
| G607 | 940 | 941 | | | |
| G610 | 944 | 945 | | | |
| G615 | 58 | 949 | OE | Altered architecture | Some plants were bushy and/or had fused cotyledons |
| | | | OE | Fertility | Little or no pollen production, poor filament elongation |
| G616 | 2 | 953 | OE | Disease resistance | Increased resistance to *Erysiphe* |
| G629 | 956 | 957 | OE | Leaf morphology | Altered leaf morphology |
| | | | OE | Seed oil content | Decreased seed oil content |
| | | | OE | Seed protein content | Increased seed protein content |
| G630 | 959 | 960 | OE | Seed protein content | Increased seed protein content |
| | | | OE | Tissue-specific expression | Embryo specific expression |
| G632 | 962 | 963 | | | |
| G633 | 965 | 966 | | | |
| G634 | 969 | 970 | OE | Trichome morphology and number | Increased trichome density and size |
| | | | OE | Altered light response and/or shade tolerance | Increased shade tolerance; lack of shade avoidance phenotype |
| | | | OE | Water deprivation tolerance | More tolerant to desiccation and drought |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G640 | 972 | 973 | | | |
| G641 | 975 | 976 | | | |
| G642 | 979 | 980 | | | |
| G649 | 983 | 984 | | | |
| G653 | 987 | 988 | OE | Altered C/N sensing | Greater growth and/or vigor on media with low nitrogen or lacking nitrogen source |
| G654 | 991 | 992 | | | |
| G656 | 994 | 995 | | | |
| G658 | 998 | 999 | | | |
| G659 | 1002 | 1003 | | | |
| G660 | 1006 | 1007 | | | |
| G661 | 1010 | 1011 | | | |
| G663 | 38 | 1015 | OE | Seed oil content | Decreased seed oil |
| | | | OE | Seed protein content | Increased seed protein |
| | | | OE | Anthocyanins | Increased anthocyanins in leaf, root, seed |
| G664 | 29 | 1019 | OE | Cold tolerance | Increased tolerance to cold; better germination at 8° C. |
| G665 | 1022 | 1023 | | | |
| G666 | 1026 | 1027 | | | |
| G668 | 45 | 1031 | OE | Seed protein content | Increased seed protein content |
| | | | OE | Seed oil content | Decreased seed oil content |
| | | | OE | Seed morphology | Reduced seed color |
| G669 | 1035 | | OE | Morphology | Small, rounded leaf morphology and spindly bolts with low fertility |
| G670 | 1036 | 1037 | OE | Plant size | Small plant |
| G671 | 1040 | 1041 | OE | Stem | Altered inflorescence stem structure |
| | | | OE | Flower | Reduced petal abscission |
| | | | OE | Leaf | Altered leaf shape; true leaves curl down, secondary bolts replaced by odd leaf-like structures |
| | | | OE | Size | Small plant |
| | | | OE | Fertility | Reduced fertility/underdevelopment of flowers |
| G672 | 1044 | 1045 | | | |
| G673 | 1048 | 1049 | | | |
| G675 | 1051 | 1052 | | | |
| G676 | 1055 | 1056 | OE | Trichome | Reduced trichome number, ectopic trichome formation |
| G677 | 1059 | 1060 | | | |
| G679 | 1063 | 1064 | | | |
| G680 | 68 | 1067 | OE | Flowering time | Late flowering |
| | | | OE | Sugar sensing/ glucose tolerance | Reduced germination on 5% glucose medium |
| G682 | 30 | 1071 | OE | Heat tolerance | More tolerance to heat; seedlings were larger and greener in germination and growth assays at 32° C. |
| | | | OE | Salt tolerance | More tolerant to salt; seedlings were larger and greener in a germination assay on 150 mM NaCl |
| | | | OE | Hyperosmotic stress | More tolerant to mannose; more tolerant to sucrose; better germination on a 9.4% sucrose medium |
| | | | OE | Hormone sensitivity | Less sensitive to ABA; seedlings were larger and greener in 0.5 μM ABA in a germination assay |
| | | | OE | Low nutrient tolerance | More tolerant to nitrogen-limiting conditions |
| | | | OE | Altered C/N sensing | Greater growth and/or vigor on media with low nitrogen or lacking nitrogen source |
| | | | OE | Water deprivation tolerance | More tolerant to desiccation and drought |
| | | | OE | Trichome number | Glabrous, lack of trichomes |
| | | | OE | Root morphology | Increased root hair number |
| G699 | 1074 | 1075 | | | |
| G713 | 1077 | 1078 | | | |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G714 | 1080 | 1081 | OE | Leaf morphology | Some lines had long, narrow, curled leaves |
| G718 | 1084 | 1085 | OE | Seed protein content | Increased seed protein |
| | | | OE | Leaf fatty acids | Altered leaf fatty acid composition; decreased 16:0 and 16:3, increased 16:1 and 18:3 |
| | | | OE | Seed prenyl lipids | Increased seed lutein |
| | | | OE | Seed oil content | Decreased seed oil |
| | | | OE | Seed fatty acids | Seed fatty acids; decrease in 18:1 fatty acids in seeds |
| G721 | 1088 | 1089 | | | |
| G723 | 1092 | 1093 | | | |
| G725 | 1096 | 1097 | | | |
| G726 | 1100 | 1101 | | | |
| G727 | 1103 | 1104 | | | |
| G729 | 1107 | 1108 | | | |
| G731 | 1111 | 1112 | | | |
| G732 | 47 | 1116 | OE | Seed protein content | One OE line had increased, another decreased seed protein content |
| | | | OE | Seed oil content | One OE line had increased, another decreased seed oil content |
| | | | OE | Altered architecture | Reduced apical dominance |
| | | | OE | Flower morphology | Abnormal flowers |
| G735 | 1119 | 1120 | | | |
| G736 | 98 | 1123 | OE | Flowering time | Late flowering |
| | | | OE | Leaf morphology | Small, dark green rounded leaves with long petioles |
| G740 | 106 | 1126 | OE | Altered growth rate | Slow growth |
| G743 | 1129 | 1130 | | | |
| G748 | 54 | 1134 | OE | Stem | More vascular bundles in stem |
| | | | OE | Flowering time | Late flowering |
| | | | OE | Seed prenyl lipids | Increased lutein content |
| G749 | 1137 | 1138 | | | |
| G751 | 1141 | 1142 | | | |
| G752 | 1144 | 1145 | OE | Flowering time | Late flowering |
| G759 | 1147 | 1148 | | | |
| G763 | 1150 | 1151 | | | |
| G764 | 1153 | 1154 | | | |
| G773 | 1156 | 1157 | OE | Altered C/N sensing | Increased sensitivity media with low nitrogen or lacking nitrogen source |
| G776 | 39 | 1161 | OE | Seed oil composition | Altered seed fatty acid composition; decreased 20:1 and 22:1 fatty acids |
| G777 | 80 | 1165 | OE | Seed oil content | Decreased seed oil |
| | | | OE | Leaf insoluble sugars | Increased leaf rhamnose |
| G778 | 40 | 1169 | OE | Seed oil composition | Increased seed 18:1 fatty acid |
| G779 | 1172 | 1173 | OE | Fertility | Reduced fertility |
| | | | OE | Flower | Homeotic transformations; conversion of sepals to carpels, most severely affected showed full conversion of sepals to carpels with ovules, stigmatic tissue on Petals and stamens, and in some cases showed organ fusions |
| G780 | 1176 | 1177 | KO | Seed fatty acids | Significant increases in 16:0, 18:0, and 20:0 and decreases in 18:2, 20:1, and 20:2 |
| | | | OE | Seed fatty acids | Significant increase in 18:2 and a significant decrease in 18:3 |
| G782 | 1180 | 1181 | OE | Sugar sensing/ sucrose tolerance | More tolerant to sucrose; better germination on 9.4% sucrose medium |
| G783 | 1184 | 1185 | OE | Sugar sensing/ sucrose tolerance | More tolerant to sucrose; better germination on 9.4% sucrose medium |
| G784 | 1187 | 1188 | | | |
| G786 | 1191 | 1192 | | | |
| G787 | 1194 | 1195 | | | |
| G788 | 1198 | 1199 | | | |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G791 | 1202 | 1203 | OE | Seed oil composition | Decreased decrease in 18:1 seed fatty acid |
| | | | OE | Leaf insoluble sugars | Altered leaf cell wall polysaccharide composition |
| | | | OE | Leaf fatty acid composition | Decreased 18:2 leaf fatty acid |
| G792 | 1206 | 1207 | | | |
| G793 | 1210 | 1211 | OE | Disease resistance | Increased resistance to *Sclerotinia* |
| G795 | 1214 | 1215 | | | |
| G798 | 1218 | 1219 | | | |
| G801 | 1221 | 1222 | OE | Salt tolerance | More tolerant to salt; seedlings were larger and greener in a germination assay on 150 mM NaCl |
| G802 | 1225 | 1226 | | | |
| G804 | 1228 | 1229 | | | |
| G811 | 1232 | 1233 | | | |
| G830 | 1235 | 1236 | | | |
| G832 | 1238 | | | | |
| G849 | 1239 | 1240 | KO | Seed protein content | Altered seed protein content |
| | | | KO | Seed oil content | Increased seed oil content |
| | | | KO | Seed sterols | Decease in β-sitosterol |
| G860 | 1242 | 1243 | | | |
| G864 | 1246 | 1247 | OE | Plant size | Small plant |
| | | | OE | Cold tolerance | Increased adult stage sensitivity to 8° C. |
| | | | OE | Heat tolerance | More tolerance to heat; seedlings were larger and greener in a germination assay at 32° C. |
| G865 | 13 | 1251 | OE | Disease resistance | Increased resistance to *Erysiphe* |
| | | | OE | Disease resistance | Increased susceptibility to *Botrytis* |
| | | | OE | Flowering time | Early flowering |
| | | | OE | Seed protein content | Increased seed protein |
| | | | OE | Altered morphology | Numerous secondary inflorescence meristems-bushy appearance |
| G866 | 1253 | 1254 | OE | Altered C/N sensing | Greater growth and/or vigor on media with low nitrogen or lacking nitrogen source |
| G867 | 69 | 1258 | OE | Sugar sensing/ sucrose tolerance | More tolerant to sucrose; better seedling vigor on 9.4% sucrose medium |
| | | | OE | Salt tolerance | More tolerant to salt; better seedling vigor in a germination assay on 150 mM NaCl |
| | | | OE | Water deprivation tolerance | Increased survival and recovery from drought |
| | | | OE | Hormone sensitivity | Less sensitive to ABA; seedlings were larger and greener in 0.5 μM ABA in a germination assay |
| | | | OE | Cold tolerance | Increased tolerance to cold; at 8° C. in germination and growth assays, some seedlings were larger and during germination and growth |
| G869 | 6 | 1262 | OE | Leaf insoluble sugars | Increase in fucose |
| | | | OE | Seed oil composition | Increased 18:1 seed fatty acids |
| | | | OE | Leaf fatty acids | 16:0 levels decreased and 16:3 levels increased |
| | | | OE | Disease resistance | Increased resistance to *Erysiphe* |
| | | | OE | Morphology: other | Small and spindly plant |
| | | | OE | Flower morphology | Abnormal anther development |
| G872 | 1265 | 1266 | KO | Developmental defects | Embryo lethal |
| | | | OE | Altered C/N sensing | Greater growth and/or vigor on media with low nitrogen or lacking nitrogen source |
| G877 | 1268 | 1269 | KO | Embryo lethal | Embryo lethal phenotype: potential herbicide target |
| G881 | 14 | 1273 | OE | Disease resistance | Increased susceptibility to *Botrytis* |
| | | | OE | Disease resistance | Increased susceptibility to *Erysiphe* |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G883 | 41 | 1277 | OE | Seed prenyl lipids | Decreased seed lutein |
| G886 | 1280 | 1281 | | | |
| G891 | 1284 | 1285 | | | |
| G896 | 15 | 110 | KO | Disease resistance | Increased susceptibility to Fusarium |
| | | | OE | Disease resistance | Increased resistance to Botrytis |
| G897 | 1292 | 1293 | | | |
| G899 | 1296 | 1297 | | | |
| G902 | 1299 | 1300 | | | |
| G908 | 1303 | 1304 | | | |
| G909 | 1307 | 1308 | | | |
| G911 | 31 | 1311 | OE | Low nutrient tolerance | Increased growth on potassium-free medium |
| | | | OE | Seed protein content | Increased seed protein content |
| | | | OE | Seed oil content | Decreased seed oil content |
| G912 | 70 | 1314 | OE | Freezing tolerance | Increased freezing tolerance |
| | | | OE | Altered morphology | Dark green color |
| | | | OE | Water deprivation tolerance | Increased survival and recovery from drought |
| | | | OE | Sugar sensing/ glucose tolerance | Reduced cotyledon expansion in 5% glucose |
| | | | OE | Plant size | Small plant |
| | | | OE | Flowering time | Late flowering |
| | | | OE | Altered C/N sensing | Greater growth and/or vigor on media with low nitrogen or lacking nitrogen source |
| G913 | 1317 | 1318 | OE | Flowering time | Late flowering |
| | | | OE | Freezing tolerance | Increased freezing tolerance |
| | | | OE | Water deprivation tolerance | Increased survival and recovery from drought |
| | | | OE | Cold tolerance | Increased tolerance to cold; more tolerant to 8° C. in a growth assay; some seedlings had less anthocyanin |
| G914 | 1321 | 1322 | | | |
| G915 | 1325 | 1326 | | | |
| G921 | 1329 | 1330 | OE | Hyperosmotic stress tolerance | Increased sensitivity to 10% polyethylene glycol or 150 mM salt |
| | | | OE | Leaf | Serrated leaves |
| G927 | 1333 | 1334 | | | |
| G928 | 1337 | 1338 | OE | Sugar sensing/sucrose tolerance | More tolerant to sucrose; better germination on 9.4% sucrose medium |
| | | | OE | Water deprivation tolerance | More tolerant to desiccation |
| | | | OE | Cold tolerance | More tolerant to cold; in an 8° C. germination assay, seedlings were larger and had less anthocyanin |
| G929 | 1341 | 1342 | | | |
| G932 | 1345 | 1346 | OE | Leaf morphology | Altered development, dark green color |
| | | | OE | Plant size | Reduced size |
| | | | OE | Altered C/N sensing | Greater growth and/or vigor on media with low nitrogen or lacking nitrogen source |
| G938 | 42 | 1350 | OE | Seed oil composition | Overexpressors had increased 16:0, 18:0, 20:0, and 18:3 fatty acids, decreased 18:2, 20:1, 22:1 fatty acids |
| G939 | 1353 | 1354 | | | |
| G941 | 1357 | 1358 | | | |
| G942 | 1363 | 1361 | | | |
| G960 | 1364 | 1365 | | | |
| G964 | 32 | 1369 | OE | Heat tolerance | More tolerance to heat; seedlings were larger and greener in a germination assay at 32° C. |
| | | | KO | Altered C/N sensing | Greater growth and/or vigor on media with low nitrogen or lacking nitrogen source |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G965 | 1371 | 1372 | OE | Seed oil composition | Increase in 18:1 fatty acid |
| G975 | 84 | 1376 | OE | Leaf fatty acids | Increased wax in leaves |
| | | | OE | Altered C/N sensing | Greater growth and/or vigor on media with low nitrogen or lacking nitrogen source |
| | | | OE | Water deprivation tolerance | Increased survival and recovery from drought |
| G976 | 1379 | 1380 | | | |
| G977 | 1383 | 1384 | OE | Plant size | Small plant |
| | | | OE | Morphology: color | Dark green |
| | | | OE | Leaf morphology | Altered leaf shape; generally wrinkled or curled |
| | | | OE | Fertility | Reduced fertility; underdeveloped flowers, abnormal inflorescences |
| G986 | 1387 | 1388 | | | |
| G987 | 1391 | 1392 | KO | Leaf fatty acids | Reduction in 16:3 fatty acid |
| | | | KO | Leaf prenyl lipids | Presence of two xanthophylls, tocopherol not normally found in leaves; reduced chlorophyll a and b |
| G994 | 95 | 1396 | OE | Flowering time | Late flowering |
| | | | OE | Plant size | Small plants |
| G996 | 71 | 1400 | OE | Sugar sensing/ glucose tolerance | Reduced germination on 5% glucose medium |
| G997 | 1403 | 1404 | | | |
| G998 | 1407 | 1408 | | | |
| G1000 | 1413 | 1411 | | | |
| G1004 | 1414 | 1415 | | | |
| G1005 | 1418 | 1419 | | | |
| G1006 | 1422 | 1423 | OE | Disease resistance | Increased resistance to *Erysiphe* |
| | | | OE | Disease resistance | Increased resistance to *Sclerotinia* |
| G1008 | 1426 | 1427 | OE | Plant morphology | Overexpressors were small and bushy |
| G1017 | 1430 | 1431 | | | |
| G1020 | 1434 | 1435 | OE | Plant size | Very small T1 plants |
| G1021 | 1438 | 1439 | | | |
| G1025 | 1442 | 1443 | | | |
| G1030 | 1445 | 1446 | | | |
| G1034 | 1448 | 1449 | | | |
| G1038 | 51 | 1452 | OE | Leaf morphology | Rounded leaves |
| | | | OE | Leaf insoluble sugars | Decreased insoluble sugars |
| G1039 | 1454 | 1455 | | | |
| G1040 | 1458 | 1459 | OE | Seed morphology | Smaller and more rounded seeds |
| G1045 | 1462 | 1463 | | | |
| G1048 | 1466 | 1467 | OE | *Erysiphe* | Increased tolerance to *Erysiphe orontii* |
| | | | OE | Seed protein content | Increased seed protein content |
| | | | OE | Altered light response and/or shade tolerance | Increased shade tolerance; lack of shade avoidance phenotype |
| G1052 | 1469 | 1470 | OE | Flowering time | Late flowering |
| | | | OE | Seed prenyl lipids | Decrease in lutein and increase in xanthophyll 1 |
| G1055 | 1473 | 1474 | | | |
| G1057 | 1476 | 1477 | | | |
| G1058 | 1480 | 1481 | | | |
| G1060 | 1484 | | | | |
| G1061 | 1487 | 1488 | | | |
| G1065 | 1491 | 1492 | | | |
| G1067 | 1494 | 1495 | OE | Leaf morphology | Upcurled rosette leaves |
| | | | OE | Plant size | Small plant |
| | | | OE | Fertility | Reduced fertility |
| | | | OE | Water deprivation tolerance | Increased survival and recovery from drought |
| | | | OE | Hormone sensitivity | Less sensitive to ABA; seedlings were larger and greener in 0.5 μM ABA in a germination assay |
| G1068 | 72 | 1499 | OE | Sugar sensing/glucose tolerance | Reduced cotyledon expansion in 5% glucose |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G1071 | 1502 | 1503 | | | |
| G1072 | 1506 | 1507 | | | |
| G1073 | 59 | 1511 | OE | Plant size | Increased plant size |
| | | | OE | Seed morphology | Larger seeds; increased seed yield |
| | | | OE | Leaf | Serrated leaves |
| | | | OE | Flowering time | Flowering slightly delayed |
| | | | OE | Salt tolerance | More tolerant to salt; seedlings were larger and greener in a germination assay on 150 mM NaCl |
| | | | OE | Sugar sensing/sucrose tolerance | More tolerant to sucrose; better germination on 9.4% sucrose medium |
| | | | OE | Hyperosmotic stress | More tolerant to mannitol; greater germination and growth on 300 mM mannitol medium |
| | | | OE | Water deprivation tolerance | More tolerant to desiccation and drought |
| G1075 | 1514 | 1515 | OE | Plant size | Small plant |
| | | | OE | Flower morphology | Reduced or absent petals, sepals and stamens |
| | | | OE | Fertility | Reduced fertility |
| | | | OE | Leaf morphology | Pointed leaves in some seedlings; twisted or curled leaves and serrations in rosette stage |
| G1078 | 1518 | 1519 | | | |
| G1082 | 1521 | 1522 | | | |
| G1083 | 1525 | 1526 | | | |
| G1090 | 1529 | 1530 | OE | Altered C/N sensing | Greater growth and/or vigor on media with low nitrogen or lacking nitrogen source |
| G1093 | 1532 | 1533 | | | |
| G1095 | 1536 | 1537 | | | |
| G1099 | 1540 | 1541 | | | |
| G1100 | 1544 | 1545 | OE | Altered light response and/or shade tolerance | Increased shade tolerance; lack of shade avoidance phenotype |
| G1107 | 1548 | 1549 | | | |
| G1109 | 1552 | 1553 | | | |
| G1130 | 1556 | 1557 | | | |
| G1131 | 1560 | 1561 | | | |
| G1133 | 81 | 1565 | OE | Leaf prenyl lipids | Decreased leaf lutein |
| G1134 | 1567 | 1568 | OE | Silique morphology | Siliques with altered shape |
| | | | OE | Hormone sensitivity | Altered response to ethylene: longer hypocotyls and lack of apical hook |
| | | | OE | Hormone sensitivity | Less sensitive to ABA; seedlings were larger and greener in 0.5 μM ABA in a germination assay |
| | | | OE | Root morphology | Several seedlings had more root growth |
| G1137 | 1571 | 1572 | | | |
| G1141 | 1575 | 1576 | | | |
| G1149 | 1578 | 1579 | | | |
| G1181 | 1582 | 1583 | OE | Plant size | Small T1 plants |
| G1196 | 1585 | 1586 | | | |
| G1197 | 1588 | 1589 | | | |
| G1202 | 1592 | 1593 | OE | Leaf fatty acids | Significant increase (>2 standard deviation) in 18:0 and 18:1 fatty acids; decrease in 18:3 saturated fatty acids in leaves |
| G1207 | 1595 | 1596 | | | |
| G1208 | 1600 | 1598 | | | |
| G1218 | 1601 | 1602 | | | |
| G1228 | 1606 | 1604 | OE | Plant size | Reduced size |
| G1232 | 1607 | 1608 | | | |
| G1233 | 1610 | 1611 | | | |
| G1240 | 1613 | 1614 | | | |
| G1241 | 1616 | 1617 | | | |
| G1249 | 1619 | 1620 | | | |
| G1258 | 1623 | 1624 | | | |
| G1261 | 1627 | 1628 | | | |
| G1266 | 82 | 1632 | OE | Leaf fatty acids | Decreased 16:0, 18:2, increased 18:3 |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| | | | OE | Disease resistance | Increased resistance to *Erysiphe* |
| | | | OE | Disease resistance | Increased resistance to *Botrytis* |
| | | | OE | Disease resistance | Increased resistance to *Sclerotinia* |
| | | | OE | Plant size | Small plant |
| | | | OE | Fertility | Reduced fertility |
| | | | OE | Leaf insoluble sugars | Alterations in xylose, and mannose, and galactose concentrations; decreased rhamnose, some lines had more arabinose |
| | | | OE | Altered C/N sensing | Greater growth and/or vigor on media with low nitrogen or lacking nitrogen source |
| | | | OE | Salt tolerance | More tolerant to salt; seedlings were larger and greener in a germination assay on 150 mM NaCl |
| | | | OE | Hyperosmotic stress | More tolerant to mannitol; greater germination and growth on 300 mM mannitol medium |
| | | | OE | Hormone sensitivity | Less sensitive to ABA; seedlings were larger and greener in 0.5 µM ABA in a germination assay |
| | | | OE | Cold tolerance | Increased tolerance to cold; in an 8° C. germination assay, seedlings were larger, greener and had less anthocyanin |
| G1269 | 50 | 1636 | OE | Leaf morphology | Long petioles, upturned leaves |
| G1275 | 1639 | 1640 | OE | Plant size | Small plant |
| | | | OE | Altered architecture | Reduced apical dominance |
| | | | OE | Heat tolerance | More tolerance to heat; seedlings were larger and greener in a germination assay at 32° C. |
| | | | OE | Cold tolerance | More tolerant to cold; in 8° C. germination and growth assays; some seedlings were larger and had less anthocyanin |
| | | | OE | Hormone sensitivity | Less sensitive to ABA; seedlings were larger and greener in 0.5 µM ABA in a germination assay |
| G1293 | 1643 | | | | |
| G1300 | 1644 | 1645 | OE | Seed fatty acids | One line had a reduction in 16:0, 18:0 and 20:0 seed fatty acids and an increase in the unsaturated 18:1 and 18:2 fatty acids; another line had significant increases in 16:0, 18:0 and 20:0 fatty acids and a reduction in 20:1 |
| G1309 | 1647 | 1648 | OE | Plant size | Small plant |
| | | | OE | Leaf insoluble sugars | Increased mannose |
| G1311 | 1651 | 1652 | OE | Fertility | Reduced fertility |
| | | | OE | Plant size | Small plant |
| G1315 | 1655 | 1656 | OE | Leaf chemistry | Increased leaf β-carotene |
| G1319 | 1659 | 1660 | | | |
| G1321 | 1663 | 1664 | | | |
| G1323 | 1667 | 1668 | OE | Seed oil content | Decreased seed oil |
| | | | OE | Seed protein content | Increased seed protein |
| | | | OE | Plant size | Small T1 plants |
| | | | OE | Morphology: color | Dark green |
| G1324 | 83 | 1672 | OE | Leaf prenyl lipids | Decreased leaf lutein, increased leaf xanthophyll |
| G1326 | 1675 | 1676 | OE | Flower morphology | Petals and sepals were smaller |
| | | | OE | Plant size | Small plant |
| | | | OE | Fertility | Reduced fertility |
| G1327 | 1679 | 1680 | OE | Leaf morphology | Dark green leaves |
| G1328 | 43 | 1684 | OE | Seed prenyl lipids | Decreased seed lutein |
| G1329 | 1687 | 1688 | | | |
| G1333 | 1691 | 1692 | | | |
| G1334 | 104 | 1696 | OE | Plant size | Some lines were small |
| | | | OE | Plant size | Larger seedlings |
| | | | OE | Leaf morphology | Dark green leaves |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G1335 | 96 | 1700 | OE | Flowering time | Late flowering |
|  |  |  | OE | Dev and morph | Slow growth |
| G1337 | 73 | 1704 | OE | Sugar sensing | Decreased germination on 9.4% sucrose medium |
|  |  |  | OE | Leaf fatty acids | Altered leaf fatty acid composition |
| G1338 | 1706 | 1707 |  |  |  |
| G1340 | 1710 | 1711 |  |  |  |
| G1349 | 1714 | 1715 |  |  |  |
| G1350 | 1718 | 1719 |  |  |  |
| G1351 | 1721 | 1722 |  |  |  |
| G1352 | 1725 | 1726 |  |  |  |
| G1355 | 1728 | 1729 | OE | Seed oil content | Reduced seed oil |
| G1363 | 1732 | 1733 | OE | Disease resistance | Increased resistance to *Fusarium* |
|  |  |  | OE | Water deprivation | Increased tolerance to desiccation |
| G1366 | 1736 | 1737 |  |  |  |
| G1367 | 1740 | 1741 |  |  |  |
| G1383 | 1744 | 1745 |  |  |  |
| G1385 | 1748 | 1749 |  |  |  |
| G1389 | 1752 | 1753 |  |  |  |
| G1390 | 1756 | 1757 |  |  |  |
| G1394 | 1760 | 1761 |  |  |  |
| G1395 | 1764 | 1765 |  |  |  |
| G1396 | 1768 | 1769 |  |  |  |
| G1398 | 1772 | 1773 |  |  |  |
| G1403 | 1776 | 1777 | KO | Seed fatty acids | Increased 16:0 and 18:0 and decreased 20:2 seed fatty acids |
| G1411 | 1780 | 1781 | OE | Altered architecture | Loss of apical dominance |
| G1416 | 1784 | 1785 |  |  |  |
| G1419 | 1788 | 1789 | OE | Altered seed protein | Increased seed protein |
| G1427 | 1792 | 1793 |  |  |  |
| G1435 | 99 | 1796 | OE | Flowering time | Late flowering |
|  |  |  | OE | Plant size | Increased plant size |
|  |  |  | OE | Leaf morphology | Dark green leaves |
| G1437 | 1799 | 1800 |  |  |  |
| G1438 | 1802 | 1803 |  |  |  |
| G1439 | 1805 | 1806 |  |  |  |
| G1443 | 1808 | 1809 |  |  |  |
| G1449 | 1811 | 1812 | OE | Seed protein content | Increased seed protein content |
|  |  |  | OE | Flower morphology | Larger flowers with more open petals; extra petals |
| G1456 | 1815 | 1816 |  |  |  |
| G1466 | 1819 | 1820 |  |  |  |
| G1489 | 1823 | 1824 |  |  |  |
| G1496 | 1826 | 1827 | OE | Altered seed oil | Increased seed oil content |
| G1499 | 1830 | 1831 | OE | Architecture | Bolts terminating without an inflorescence; in some lines, flowers replaced with filamentous structures or carpelloid structures; less severely affected lines produced flowers where sepals were converted to carpelloid tissue |
|  |  |  | OE | Flower morphology | Petals and stamens were absent or reduced in size and number |
|  |  |  | OE | Morphology: other | Dark green leaves |
| G1509 | 1834 | 1835 |  |  |  |
| G1514 | 1837 | 1838 | OE | Disease resistance | Increased susceptibility to *Botrytis* |
| G1518 | 1840 | 1841 |  |  |  |
| G1519 | 1843 | 1844 | KO | Embryo lethal | Embryo lethal phenotype: potential herbicide target |
| G1526 | 1848 | 1846 | KO | Altered seed oil | Increased seed oil content |
| G1528 | 1849 | 1850 |  |  |  |
| G1537 | 1852 | 1853 |  |  |  |
| G1538 | 1856 | 1857 |  |  |  |
| G1540 | 1860 | 1861 | OE | Cell differentiation | Reduced cell differentiation in meristem |
| G1541 | 1864 | 1865 |  |  |  |
| G1542 | 1868 | 1869 |  |  |  |

TABLE 5-continued

Sequences and traits observed when expression of the sequences was modified in plants

| GID | DNA SEQ ID NO: | PRT SEQ ID NO: | Overexpressor (OE) or Knockout (KO) | Trait Category | Experimental Observation |
|---|---|---|---|---|---|
| G1543 | 1872 | 1873 | OE | Altered architecture | Compact plant |
|  |  |  | OE | Morphology: color | Dark green color |
|  |  |  | OE | Seed oil content | Decreased seed oil |
|  |  |  | OE | Altered leaf prenyl lipids | Increase in chlorophyll a and b |
| G1550 | 1876 | 1877 |  |  |  |
| G1586 | 1880 | 1881 | OE | Leaf morphology | Narrow leaves |
| G1634 | 1884 | 1885 | OE | Seed protein content | Decreased seed protein content |
|  |  |  | OE | Seed oil content | Increased seed oil |
| G1635 | 1888 | 1889 | OE | Morphology | Primary transformant had reduced apical dominance, reduced bolt elongation, narrow rosette leaves, and poor fertility |
| G1636 | 1892 | 1893 |  |  |  |
| G1638 | 1896 | 1897 |  |  |  |
| G1640 | 1900 | 1901 | OE | Seed oil content | Increased seed oil |
| G1643 | 1906 | 1904 |  |  |  |
| G1646 | 1907 | 1908 | OE | Seed oil content | Increased seed oil |
|  |  |  | OE | Cold tolerance | More tolerant to cold; in an 8° C. germination assay, some seedlings were larger and had less anthocyanin |
|  |  |  | OE | Water deprivation | More tolerant to desiccation |
| G1650 | 1911 | 1912 |  |  |  |
| G1653 | 1915 | 1916 |  |  |  |
| G1655 | 1919 | 1920 |  |  |  |
| G1664 | 1923 | 1924 |  |  |  |
| G1667 | 1927 | 1928 | OE | Seed protein content | Increased seed protein content |
|  |  |  | OE | Seed oil content | Decreased seed oil |
|  |  |  | OE | Leaf prenyl lipids | Increased β-carotene |
| G1669 | 1931 | 1932 |  |  |  |
| G1699 | 1934 | 1935 |  |  |  |
| G1705 | 1938 | 1939 |  |  |  |
| G1742 | 1942 | 1943 |  |  |  |
| G1773 | 1947 |  | KO | Altered C/N sensing | Greater growth and/or vigor on media with low nitrogen or lacking nitrogen source |
| G1785 | 1948 | 1949 |  |  |  |
| G1787 | 1953 |  |  |  |  |
| G1807 | 1955 |  | OE | Oxidative stress | More sensitive to acifluorfen |
| G1836 | 1956 | 1957 | OE | Salt tolerance | More tolerant to salt; seedlings were larger and greener in a germination assay on 150 mM NaCl |
|  |  |  | OE | Sugar sensing/sucrose tolerance | More tolerant to sucrose; better germination on 9.4% sucrose medium |
|  |  |  | OE | Hormone sensitivity | Less sensitive to ABA; seedlings were larger and greener in 0.5 μM ABA in a germination assay |
|  |  |  | OE | Cold tolerance | More tolerant to cold; in an 8° C. germination assay; seedlings were larger, greener and had less anthocyanin |
|  |  |  | OE | Water deprivation tolerance | Increased survival and recovery from drought |
|  |  |  | OE | Flowering time | Some lines slightly early flowering |
| G1894 | 1960 | 1961 |  |  |  |
| G1900 | 1963 | 1964 | OE | Flowering time | Late flowering |
| G1901 | 1966 | 1967 |  |  |  |
| G1903 | 1969 | 1970 | OE | Seed protein content | Decreased seed protein content |
| G1911 | 1972 | 1973 |  |  |  |
| G1917 | 1976 | 1977 | KO | Seed glucosinolate | Significant increase in peak M39489 |
| G2019 | 1979 |  | KO | Leaf prenyl lipids | Significant (>2 standard deviation) increase in the leaf prenyl lipids, xanthophylls |
| G2484 | 1980 | 1981 |  |  |  |

Example X

Plants Overexpressing G1435 (SEQ ID NOs: 99 and 1796; a GARP Family Transcription Factor)

G1435 (SEQ ID NO: 99 and polypeptide SEQ ID NO: 1796) was isolated as a cDNA clone. G1435 was later identified in the sequence of BAC F2015, GenBank accession number AB025604, released by the *Arabidopsis* Genome Initiative.

Experimental observations. The complete sequence of G1435 was determined. The function of this gene was analyzed using transgenic plants in which G1435 was expressed under the control of the 35S promoter. Plants overexpressing G1435 were larger than wild-type controls, and had dark green leaves. Primary transformants were late flowering. G1435 was expressed throughout the plant, though at lower levels in roots and germinating seeds. It is not significantly induced or repressed by any condition tested.

A second experiment in which 35S::G1435 plants were grown confirmed the late flowering phenotype of three T2 lines. G1435 could thus be used to influence flowering time in crop plants. In species such as sugarbeet where the vegetative parts of the plants constitute the crop and the reproductive tissues are discarded, it would be advantageous to delay or prevent flowering. Extending vegetative development could bring about large increases in yields.

Another potential indicator of increased yield conferred by G1435 overexpression was the increased plant size and green color (suggesting increased photosynthetic capacity). It was thus expected that G1435 may be useful for increasing yield and/or crop quality in crops, including where the vegetative portion of the plant is harvested. A confirmation of an increase in yield in a commercially important plant species was provided when a field trial of corn plants overexpressing G1435 showed two lines with significantly increased broad acre yield relative to negative segregant controls (Table 6). These lines, 642 and 653, showed increased total kernel number and total kernel weight. Line 653 showed the higher percentage increase (a statistically significant increase) in photosynthesis compared to the negative segregant controls.

TABLE 6

Results in field trials comparing means of yield of transgenics to negative segregant controls

| Line | Mean yield, overexpressor | Mean yield, control | Difference | Percent difference | p value |
|---|---|---|---|---|---|
| 641 | 213.418 | 226.181 | −12.763 | −5.643 | 0.002 |
| 665 | 223.890 | 226.181 | −2.291 | −1.013 | 0.586 |
| 649 | 224.233 | 226.181 | −1.948 | −0.862 | 0.644 |
| 662 | 228.127 | 226.181 | 1.946 | 0.860 | 0.644 |
| 660 | 221.525 | 226.181 | −4.656 | −2.059 | 0.269 |
| 646 | 215.764 | 226.181 | −10.417 | −4.606 | 0.014 |
| 656 | 227.422 | 226.181 | 1.241 | 0.548 | 0.769 |
| 664 | 226.313 | 226.181 | 0.132 | 0.058 | 0.975 |
| 642* | 232.418 | 226.181 | 6.237 | 2.757 | 0.138 |
| 653* | 234.244 | 226.181 | 8.063 | 3.565 | 0.056 |
| 654 | 229.372 | 226.181 | 3.191 | 1.410 | 0.448 |
| 651 | 230.383 | 226.181 | 4.202 | 1.858 | 0.319 |

*Increased yield in these lines observed ($p < 0.15$)

Example XI

Utilities of G1435 (SEQ ID NOs: 99 and 1796) and its Phylogenetically-Related Sequences Based on the data obtained in the above-disclosed Example, the darker green color, increased photosynthesis, increased plant size and increased yield of G1435 overexpressors all indicate that G1435-related sequence overexpression can directly result in improved yield of crop plants, ornamental plants, and woody plants used in the food, ornamental, paper, pulp, lumber or other industries.

The invention thus includes G1435-overexpressing plants, and methods for producing G1435-overexpressing plants, or delaying flowering, increasing size, increasing photosynthesis, or increasing yield in a plant where the plant overexpresses G1435 or a phylogenetically and functionally-related sequence.

Example XII

Transformation of Dicots to Produce Increased Photosynthesis, Yield or Stress Tolerance Crop species that overexpress polypeptides of the invention may produce plants with increased photosynthetic capacity and/or yield, and/or increased tolerance to water deprivation, cold and/or nutrient tolerance in both stressed and non-stressed conditions. Thus, polynucleotide sequences listed in the Sequence Listing recombined into, for example, one of the expression vectors of the invention, or another suitable expression vector, may be transformed into a plant for the purpose of modifying plant traits for the purpose of improving yield and/or quality. The expression vector may contain a constitutive, tissue-specific or inducible promoter operably linked to the polynucleotide. The cloning vector may be introduced into a variety of plants by means well known in the art such as, for example, direct DNA transfer or *Agrobacterium tumefaciens*-mediated transformation. It is now routine to produce transgenic plants using most dicot plants (see Weissbach and Weissbach (1989) *Methods for Plant Molecular Biology*, Academic Press; Gelvin et al. (1990) *Plant Molecular Biology Manual*, Kluwer Academic Publishers; Herrera-Estrella et al. (1983) *Nature* 303: 209; Bevan (1984) *Nucleic Acids Res.* 12: 8711-8721; and Klee (1985) *Bio/Technology* 3: 637-642). Methods for analysis of traits are routine in the art and examples are disclosed above.

Numerous protocols for the transformation of tomato and soy plants have been previously described, and are well known in the art. Gruber et al. (1993), in Glick and Thompson (1993) *Methods in Plant Molecular Biology and Biotechnology*, eds., CRC Press, Inc., Boca Raton, describe several expression vectors and culture methods that may be used for cell or tissue transformation and subsequent regeneration. For soybean transformation, methods are described by Miki et al. (1993) in *Methods in Plant Molecular Biology and Biotechnology*, p. 67-88, Glick and Thompson, eds., CRC Press, Inc., Boca Raton; and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al. (1987) Part. Sci. Technol. 5:27-37; Sanford (1993) *Methods Enzymol.* 217: 483-509;

Christou et al. (1992) *Plant. J.* 2: 275-281; Klein et al. (1987) *Nature* 327: 70-73; U.S. Pat. No. 5,015,580 (Christou et al), issued May 14, 1991; and U.S. Pat. No. 5,322,783 (Tomes et al.), issued Jun. 21, 1994).

Alternatively, sonication methods (see, for example, Zhang et al. (1991) *Bio/Technology* 9: 996-997); direct uptake of DNA into protoplasts using $CaCl_2$ precipitation, polyvinyl alcohol or poly-L-ornithine (see, for example, Hain et al. (1985) *Mol. Gen. Genet.* 199: 161-168; Draper et al. (1982) *Plant Cell Physiol.* 23: 451-458); liposome or spheroplast fusion (see, for example, Deshayes et al. (1985) *EMBO J.*, 4: 2731-2737; Christou et al. (1987) *Proc. Natl. Acad. Sci. USA* 84: 3962-3966); and electroporation of protoplasts and whole cells and tissues (see, for example, Donn et al. (1990) in *Abstracts of VIIth International Congress on Plant Cell and Tissue Culture IAPTC*, A2-38: 53; D'Halluin et al. (1992) *Plant Cell* 4: 1495-1505; and Spencer et al. (1994) *Plant Mol. Biol.* 24: 51-61) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al (1986) In *Tomato Biotechnology*: Alan R. Liss, Inc., 169-178, and in U.S. Pat. No. 6,613,962, the latter method described in brief here. Eight day old cotyledon explants are precultured for 24 hours in Petri dishes containing a feeder layer of *Petunia hybrida* suspension cells plated on MS medium with 2% (w/v) sucrose and 0.8% agar supplemented with 10 µM α-naphthalene acetic acid and 4.4 µM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 µM zeatin, 67.3 µM vancomycin, 418.9 µM cefotaxime and 171.6 µM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example XIII

Transformation of Monocots to Produce Increased Photosynthesis Yield or Abiotic Stress Tolerance Cereal plants such as, but not limited to, corn, wheat, rice, sorghum, or barley, may be transformed with the present polynucleotide sequences, including monocot or dicot-derived sequences such as those presented in the present Tables, cloned into a vector such as pGA643 and containing a kanamycin-resistance marker, and expressed constitutively under, for example, the CaMV 35S or COR15 promoters, or with tissue-specific or inducible promoters. The expression vectors may be one found in the Sequence Listing, or any other suitable expression vector may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3\times10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil (1994) *Plant Mol. Biol.* 25: 925-937) such as corn, wheat, rice, sorghum (Cassas et al. (1993)), and barley (Wan and Lemeaux (1994)). DNA transfer methods such as the microprojectile method can be used for corn (Fromm et al. (1990); Gordon-Kamm et al. (1990); Ishida (1990)), wheat (Vasil et al. (1992) *Bio/Technol.* 10:667-674; Vasil et al. (1993) *Bio/Technol.* 11: 1553-1558; Weeks et al. (1993) *Plant Physiol.* 102: 1077-1084), and rice (Christou (1991) *Bio/Technol.* 9:957-962; Hiei et al. (1994) *Plant J.* 6:271-282; Aldemita and Hodges (1996) *Planta* 199: 612-617; and Hiei et al. (1997) *Plant Mol. Biol.* 35:205-218). For most cereal plants, embryogenic cells derived from immature scutellum tissues are the preferred cellular targets for transformation (Hiei et al. (1997) supra; Vasil (1994) supra). For transforming corn embryogenic cells derived from immature scutellar tissue using microprojectile bombardment, the A188XB73 genotype is the preferred genotype (Fromm et al. (1990) *Bio/Technol.* 8: 833-839; Gordon-Kamm et al. (1990) *Plant Cell* 2: 603-618). After microprojectile bombardment the tissues are selected on phosphinothricin to identify the transgenic embryogenic cells (Gordon-Kamm et al. (1990) supra). Transgenic plants are regenerated by standard corn regeneration techniques (Fromm et al. (1990) supra; Gordon-Kamm et al. (1990) supra).

Example XIV

Expression and Analysis of Increased Photosynthesis Yield or Abiotic Stress Tolerance in Non-*Arabidopsis* Species It is expected that structurally similar orthologs of the G1435 clade of polypeptide sequences, including those found in the Sequence Listing, can confer increased yield relative to control plants. As sequences of the invention have been shown to increase photosynthesis and/or yield in a variety of plant species, it is also expected that these sequences will increase yield of crop or other commercially important plant species.

Northern blot analysis, RT-PCR or microarray analysis of the regenerated, transformed plants may be used to show expression of a polypeptide or the invention and related genes that are capable of inducing abiotic stress tolerance, and/or larger size.

After a dicot plant, monocot plant or plant cell has been transformed (and the latter regenerated into a plant) and shown to have greater size, improved yield, or able to tolerate greater planting density with a coincident increase in yield, the transformed monocot plant may be crossed with itself or a plant from the same line, a non-transformed or wild-type monocot plant, or another transformed monocot plant from a different transgenic line of plants.

The function of specific polypeptides of the invention, including closely-related orthologs, have been analyzed and may be further characterized and incorporated into crop plants. The ectopic overexpression of these sequences may be regulated using constitutive, inducible, or tissue specific regulatory elements. Genes that have been examined and have been shown to modify plant traits (including increasing yield and/or abiotic stress tolerance) encode polypeptides found in the Sequence Listing. In addition to these sequences, it is expected that newly discovered polynucleotide and polypeptide sequences closely related to polynucleotide and polypeptide sequences found in the Sequence Listing can also confer alteration of traits in a similar manner to the sequences found in the Sequence Listing, when transformed into any of a considerable variety of plants of different species, and including dicots and monocots. The polynucleotide and polypeptide sequences derived from monocots (e.g., the rice sequences) may be used to transform both monocot and dicot plants, and those derived from dicots (e.g., the *Arabidopsis* and soy genes) may be used to transform either group, although it is expected that some of these sequences will function best if the gene is transformed into a plant from the same group as that from which the sequence is derived.

Sequences of the invention, that is, members of the G1435 clade, may also be used to generate transgenic plants that have increased photosynthetic capacity, produce larger plants and/ or greater yield than control plants.

It is expected that the same methods may be applied to identify other useful and valuable sequences of the present polypeptide clades, and the sequences may be derived from a diverse range of species.

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the appended claims. Modifications that become apparent from the foregoing description and accompanying figures fall within the scope of the claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07858848B2). An electronic copy of the "Sequence Listing" will also be available from the USPTO upon request and payment of the fee set forth in 37 CFR 1.19(b)(3).

What is claimed is:

1. A transgenic plant transformed with an expression vector comprising a polynucleotide sequence encoding a polypeptide having a conserved domain that has at least 85% sequence identity to amino acids 145-213 of SEQ ID NO: 163, wherein a plant transformed with the expression vector exhibits increased resistance to a fungal pathogen when compared to a control plant.

2. The transgenic plant of claim 1, wherein the conserved domain is at least 91% identical to the conserved domain of amino acids 145-213 of SEQ ID NO: 163.

3. The transgenic plant of claim 1, wherein the conserved domain is at least 95% identical to amino acids 145-213 of SEQ ID NO: 163.

4. The transgenic plant of claim 1, wherein the conserved domain is at least 97% identical to amino acids 145-213 of SEQ ID NO: 163.

5. The transgenic plant of claim 1, wherein expression of the polypeptide is regulated by a constitutive, inducible, or tissue-specific promoter.

6. The transgenic plant of claim 1, wherein the fungal pathogen is *Botrytis*.

7. The transgenic plant of claim 1, wherein the fungal pathogen is *Erysiphe*.

8. The transgenic plant of claim 1, wherein the fungal pathogen is *Sclerotinia*.

9. The transgenic plant of claim 1, wherein the transgenic plant is a transgenic seed comprising the expression vector of claim 1.

10. The transgenic plant of claim 1, wherein the transgenic plant produces a greater yield than the control plant.

11. A method for producing a transgenic plant having greater resistance to a fungal pathogen than a control plant comprising transforming a target plant with a recombinant construct encoding a polypeptide having a conserved domain at least 85% identical to amino acids 145-213 of SEQ ID NO: 163, wherein a plant transformed with the recombinant construct exhibits increased resistance to a fungal pathogen when compared to the control plant.

12. The method of claim 11, wherein the conserved domain is at least 91% identical to amino acids 145-213 of SEQ ID NO: 163.

13. The method of claim 11, wherein the conserved domain is at least 95% identical to amino acids 145-213 of SEQ ID NO: 163.

14. The method of claim 11, wherein the conserved domain is at least 97% identical to amino acids 145-213 of SEQ ID NO: 163.

15. The method of claim 11, wherein expression of the polypeptide is regulated by a constitutive, inducible, or tissue-specific promoter.

16. The method of claim 11, wherein the fungal pathogen is *Botrytis*.

17. The method of claim 11, wherein the fungal pathogen is *Erysiphe*.

18. The method of claim 11, wherein the fungal pathogen is *Sclerotinia*.

19. The method of claim 11, wherein the transgenic plant produces a greater yield than the control plant.

20. A transgenic plant comprising a recombinant polynucleotide encoding a polypeptide with at least 85% amino acid sequence identity to SEQ ID NO:163, and wherein a plant transformed with the recombinant polynucleotide exhibits increased resistance to a fungal pathogen when compared to a control plant.

21. The transgenic plant of claim 20, wherein the polypeptide is at least 90% identical to SEQ ID NO: 163.

22. The transgenic plant of claim 20, wherein the polypeptide is at least 95% identical to SEQ ID NO: 163.

23. A method for producing a transgenic plant having greater resistance to a disease than a control plant, the method comprising the step of transforming a target plant with a recombinant construct encoding a polypeptide that is at least 85% identical to SEQ ID NO: 163, wherein a plant transformed with the recombinant construct exhibits increased resistance to a fungal pathogen when compared to the control plant.

24. The method of claim 23, wherein the polypeptide is at least 90% identical to SEQ ID NO: 163.

25. The method of claim 23, wherein the polypeptide is at least 95% identical to SEQ ID NO: 163.

* * * * *